(12) United States Patent
DePaola et al.

(10) Patent No.: US 7,482,154 B2
(45) Date of Patent: Jan. 27, 2009

(54) DIAMAGNETIC FORCE FIELD BIOREACTOR

(75) Inventors: Natacha DePaola, Troy, NY (US); Aleksandar G. Ostrogorsky, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 726 days.

(21) Appl. No.: 10/845,856

(22) Filed: May 15, 2004

(65) Prior Publication Data

US 2005/0255583 A1    Nov. 17, 2005

(51) Int. Cl.
*C12M 1/00* (2006.01)
*C12M 3/00* (2006.01)
*B03C 1/00* (2006.01)
*B01D 11/04* (2006.01)
*B01D 17/06* (2006.01)

(52) U.S. Cl. .................... 435/289.1; 210/695; 210/748; 95/28; 204/557; 209/212; 435/299.2; 435/298.1; 335/209

(58) Field of Classification Search ................ 210/695, 210/748; 204/557; 209/212; 435/289.1, 435/299.2, 298.1; 335/209
See application file for complete search history.

(56) References Cited

U.S. PATENT DOCUMENTS

| | | |
|---|---|---|
| 5,081,035 A | 1/1992 | Halberstadt et al. |
| 5,155,034 A | 10/1992 | Wolf et al. |
| 5,396,136 A | 3/1995 | Pelrine |
| 5,496,722 A | 3/1996 | Goodwin et al. |
| 5,568,109 A | 10/1996 | Takayama |
| 5,846,817 A | 12/1998 | Mausli |
| 5,851,816 A | 12/1998 | Goodwin et al. |
| 5,858,783 A | 1/1999 | Goodwin et al. |
| 5,928,945 A | 7/1999 | Seliktar et al. |
| 6,117,674 A | 9/2000 | Goodwin et al. |
| 6,162,364 A * | 12/2000 | Tillotson et al. ............ 210/695 |
| 6,404,312 B1 | 6/2002 | Comtois et al. |
| 2005/0186669 A1* | 8/2005 | Ho et al. .................. 435/287.1 |
| 2006/0199170 A1* | 9/2006 | Becker .......................... 435/4 |

* cited by examiner

*Primary Examiner*—William H Beisner
*Assistant Examiner*—Nathan A Bowers
(74) *Attorney, Agent, or Firm*—Sander Rabin

(57) ABSTRACT

The invention is an apparatus comprising a magnet adapted to create a diamagnetic force field at all points in space at which a magnetic field-field gradient product of the magnet has a value greater than or equal to a threshold value. At or above the threshold value, the diamagnetic force field induces a diamagnetic body force within a biological specimen supported within a bioreactor chamber that is disposed within the diamagnetic force field. The apparatus may alter the magnitude of the induced diamagnetic body force and may alter the direction of the induced diamagnetic body with respect to a spatial coordinate system or with respect to the direction of a secondary body force acting upon or within the biological specimen, thereby altering the vector sum of the induced diamagnetic body force and the secondary body force acting on the biological specimen.

36 Claims, 37 Drawing Sheets

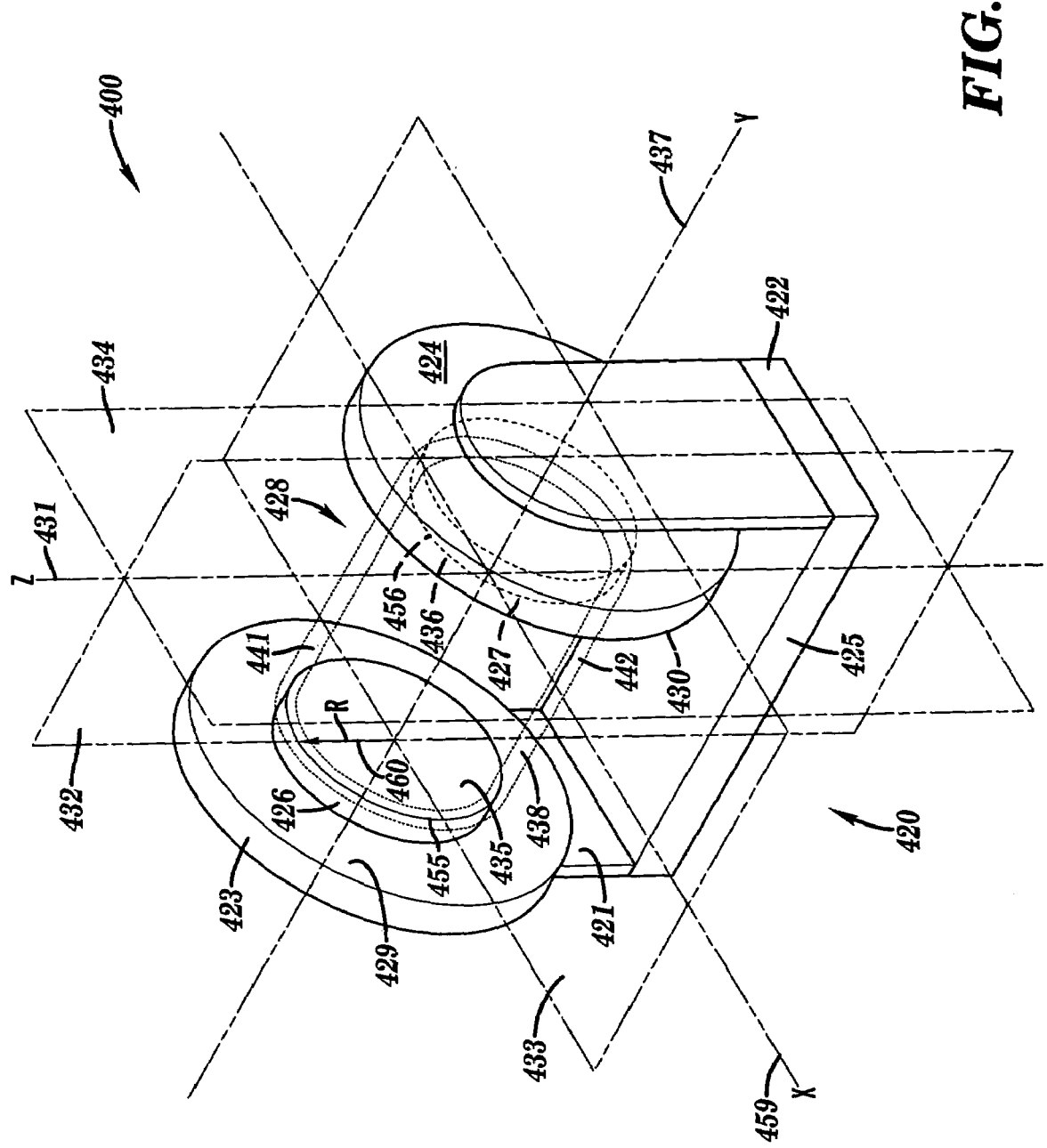

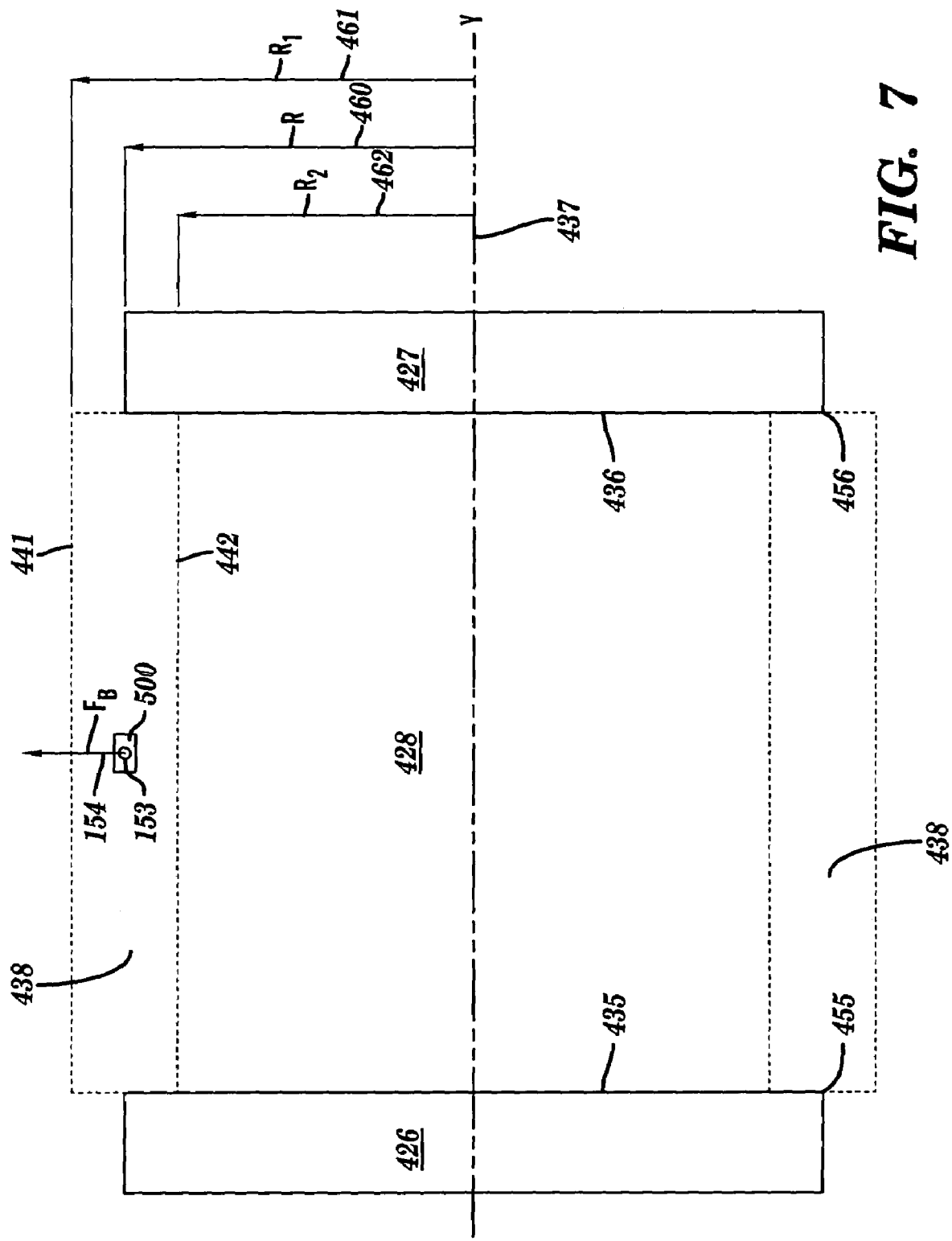

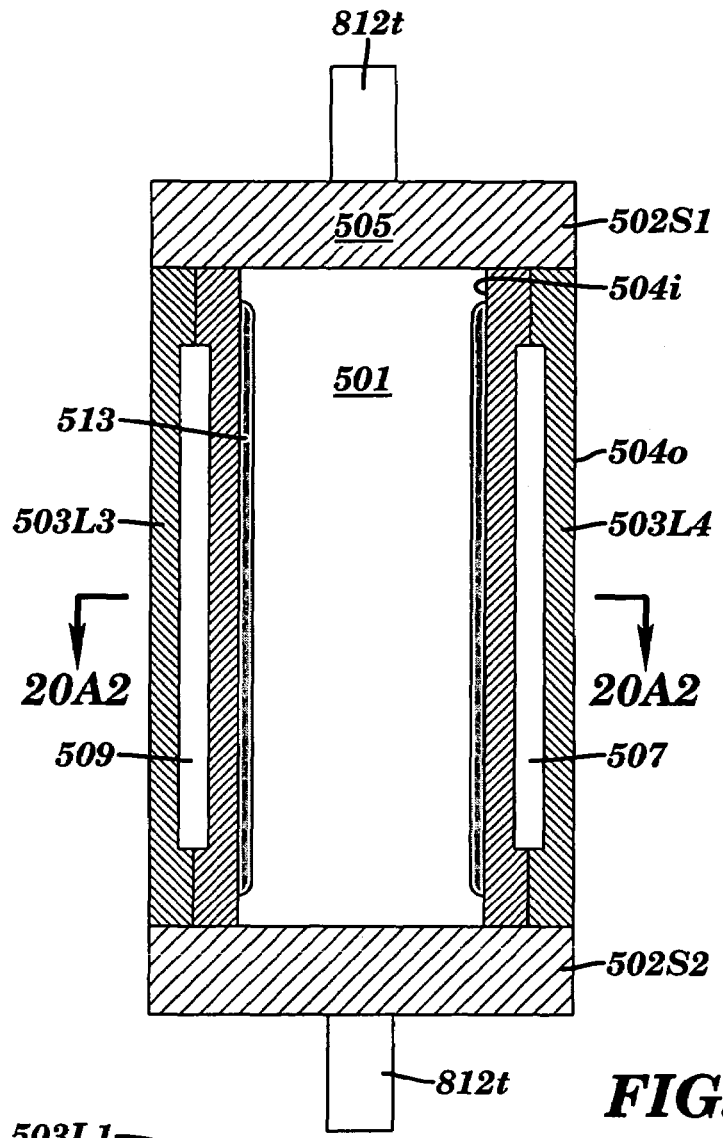
FIG. 20A1
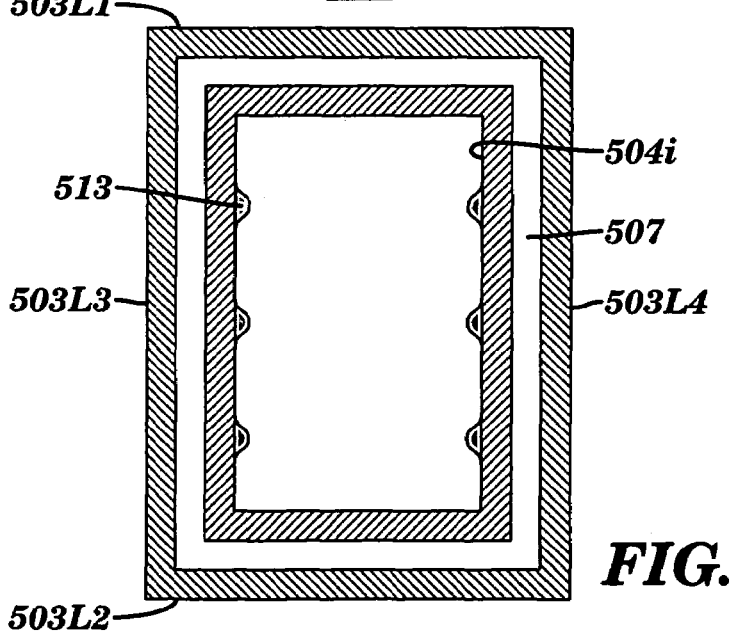
FIG. 20A2

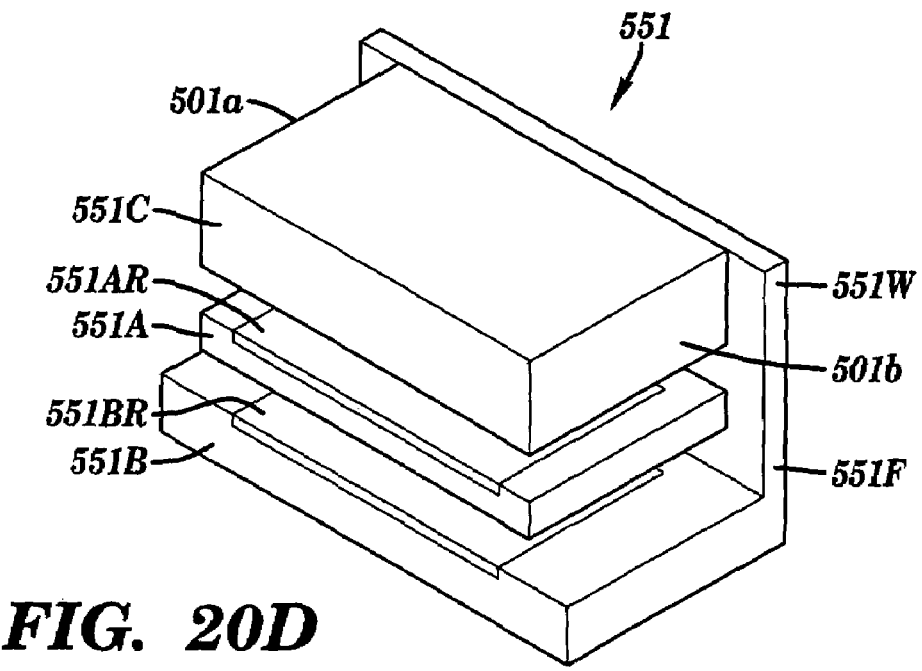
FIG. 20D
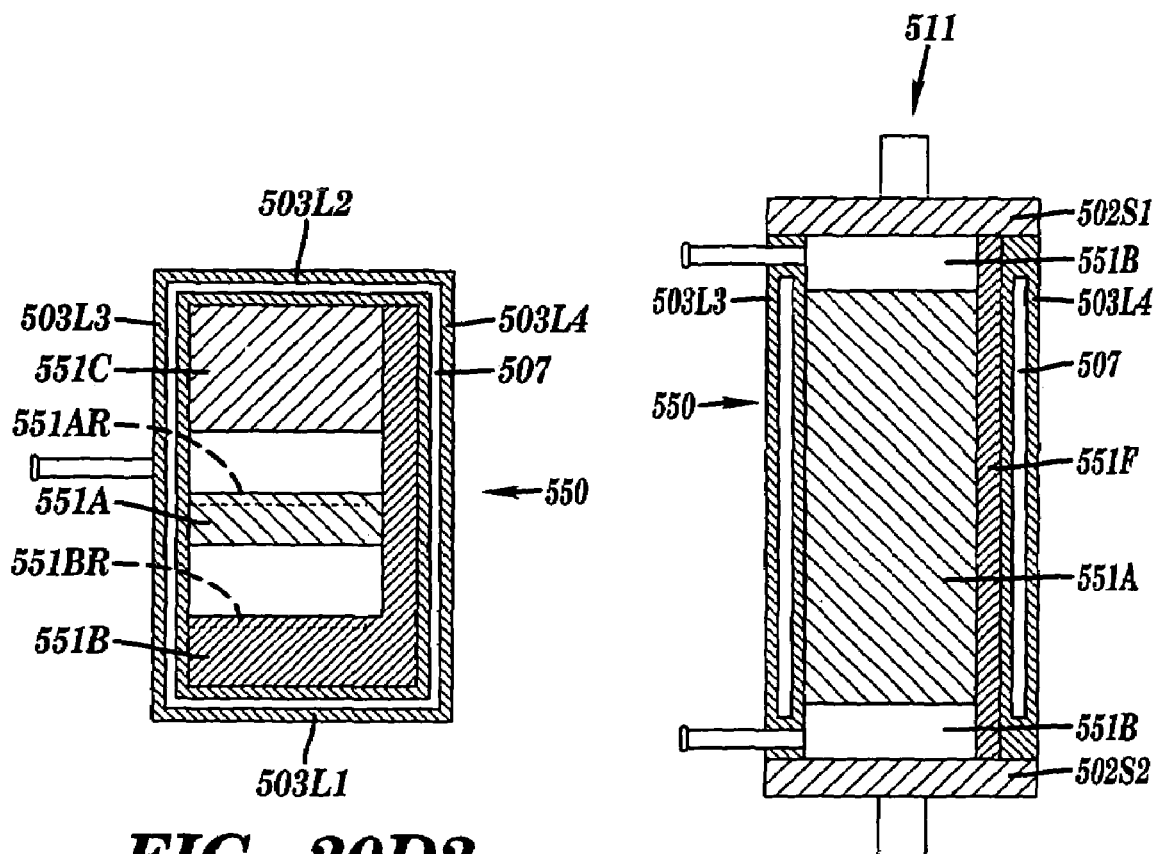
FIG. 20D2
FIG. 20D1

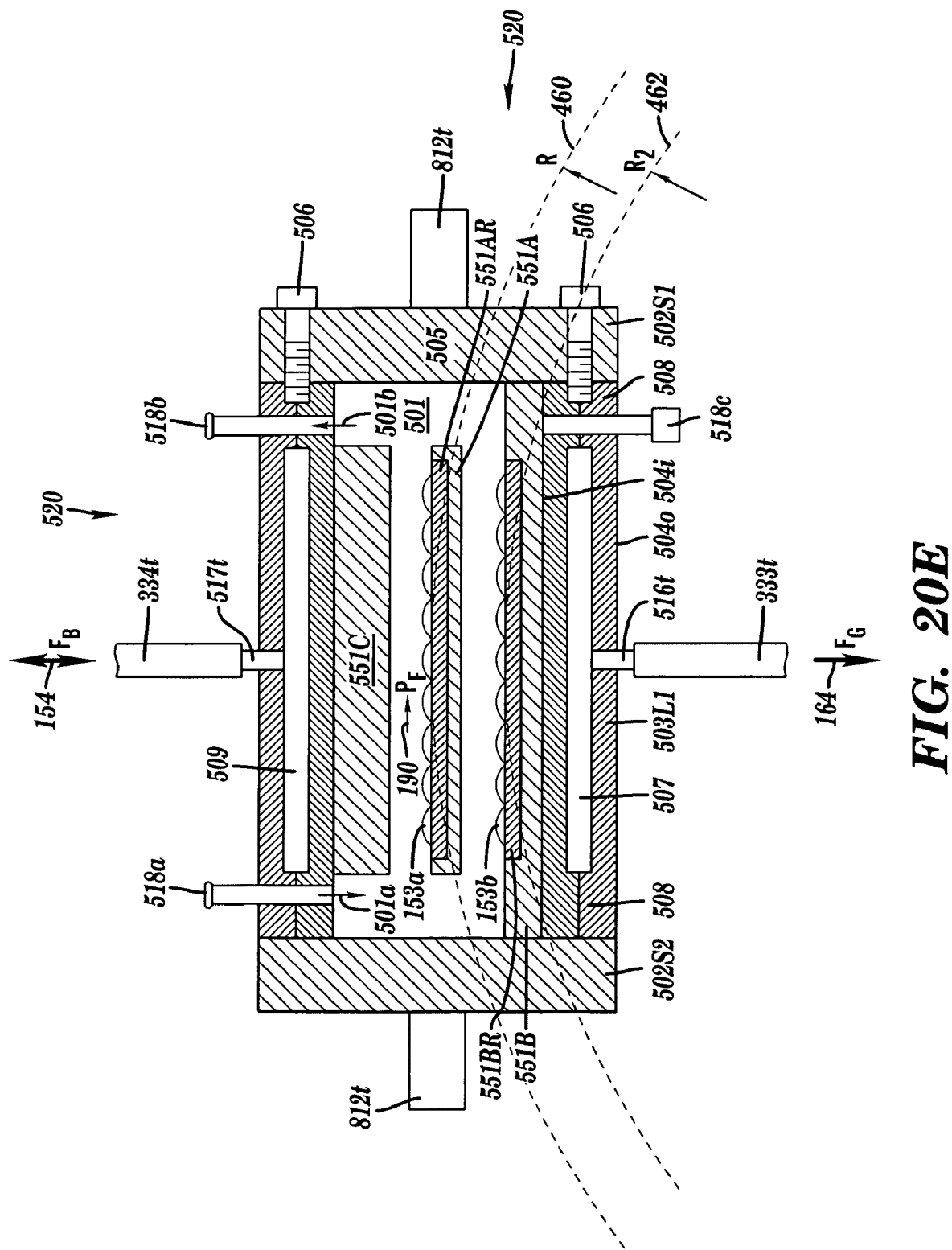

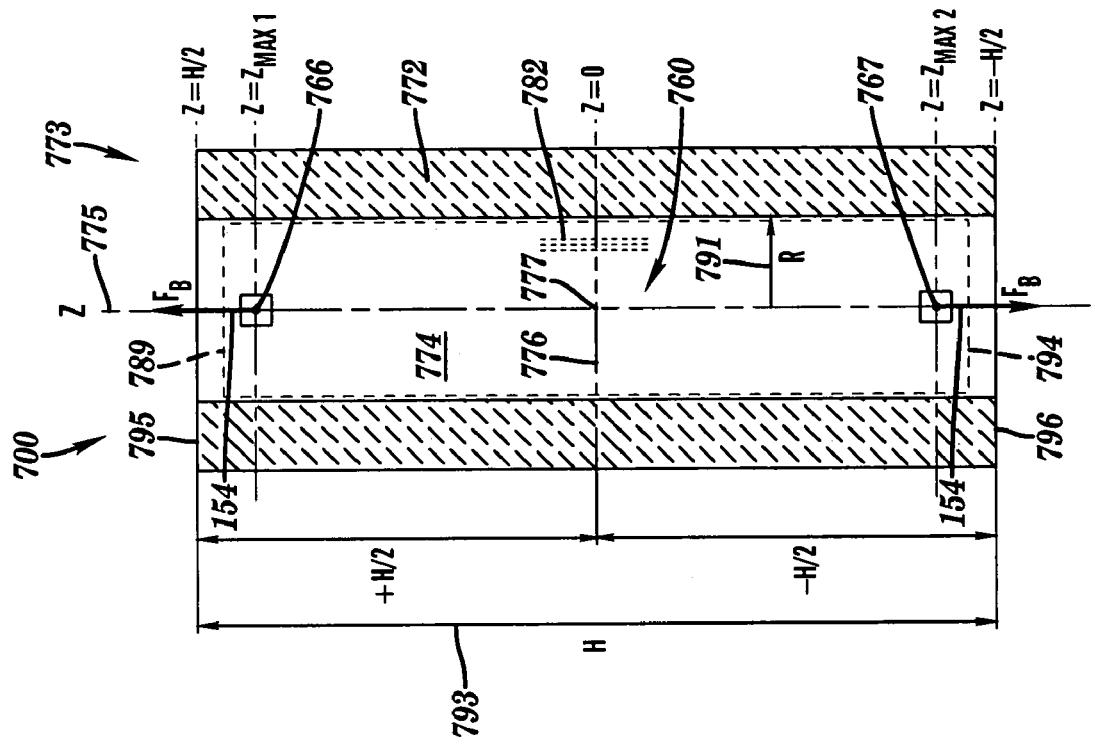
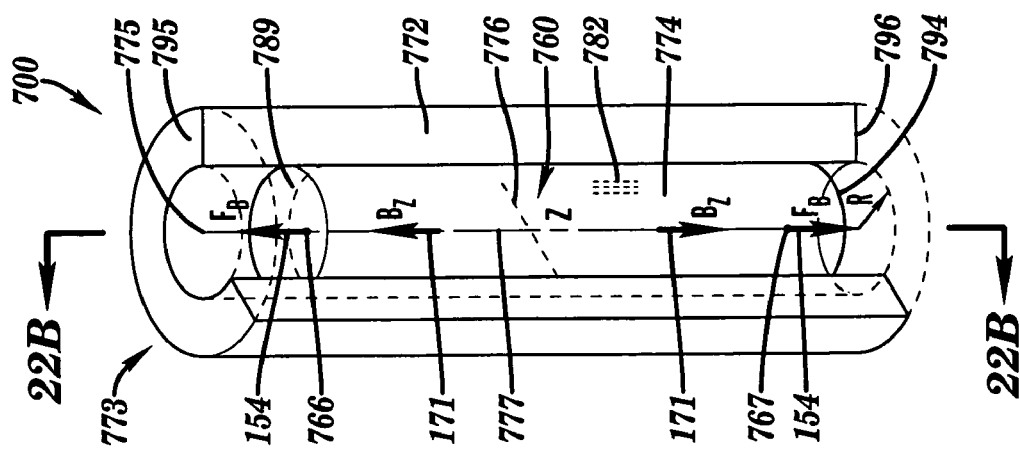

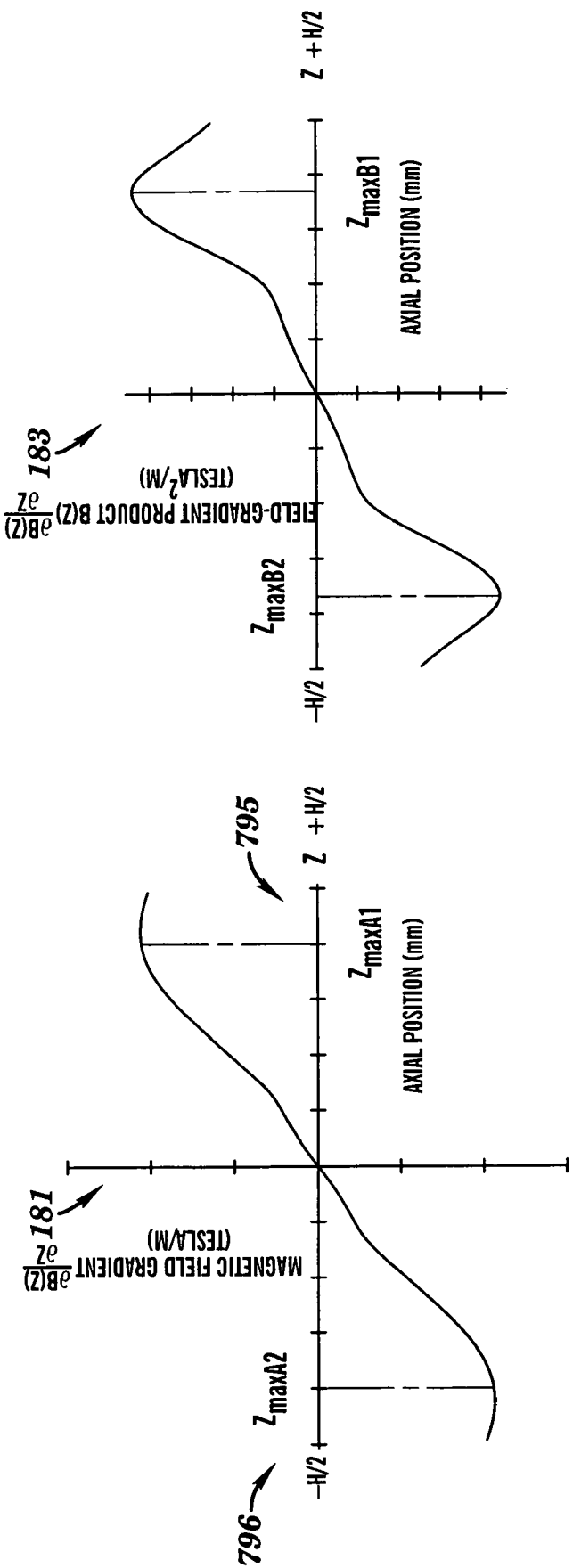

DIAMAGNETIC FORCE FIELD BIOREACTOR

BACKGROUND OF THE INVENTION

1. Technical Field

The present invention relates generally to an apparatus for generating a diamagnetic force field in one or more regions of space that is inductive of a diamagnetic body force within a biospecimen supported in vitro in the regions of space coincident with diamagnetic force field.

2. Related Art

The in vitro differentiation and self-organization of replicating mammalian cells into tissues and organs improves when they are cultured in vitro in a microgravitational environment such as that present in International Space Station. Mammalian cell bioreactors, operating in the unit-gravitational field present on the Earth's surface, cannot provide an environment conducive to the differentiation and self-organization of mammalian cells into tissues that, for example, are high-fidelity analogues of their three-dimensional counterparts in the intact organism; or, for example, that synthesize bioactive molecules of interest to basic biological research or of importance to the development of pharmaceutical agents. And, attempts to moderate or eliminate the adverse effect of unit gravity on in vitro mammalian cell differentiation and self-organization on the Earth's surface have failed to recreate an authentic microgravitational environment such as that existing, in the International Space Station.

The present invention makes a true microgravitational environment, such as that present in the International Space Station, available to researchers at any earthbound location, consequently making access to this microgravitational environment far more accessible and at an incomparably cheaper cost than the alternative of lofting a biological payload into orbit. The apparatus and methods disclosed and claimed herein are directed, inter alia, to cell and tissue engineering for organ and tissue replacement, the development of human support systems in space, and terrestrial applications in the pharmaceutical industry, medical diagnostics, and medical therapeutics.

3. BRIEF DESCRIPTION OF THE DRAWINGS

FIG. 2 is a perspective schematic illustration of a transverse electromagnet of a first exemplary embodiment of the invention.

Figure 1:
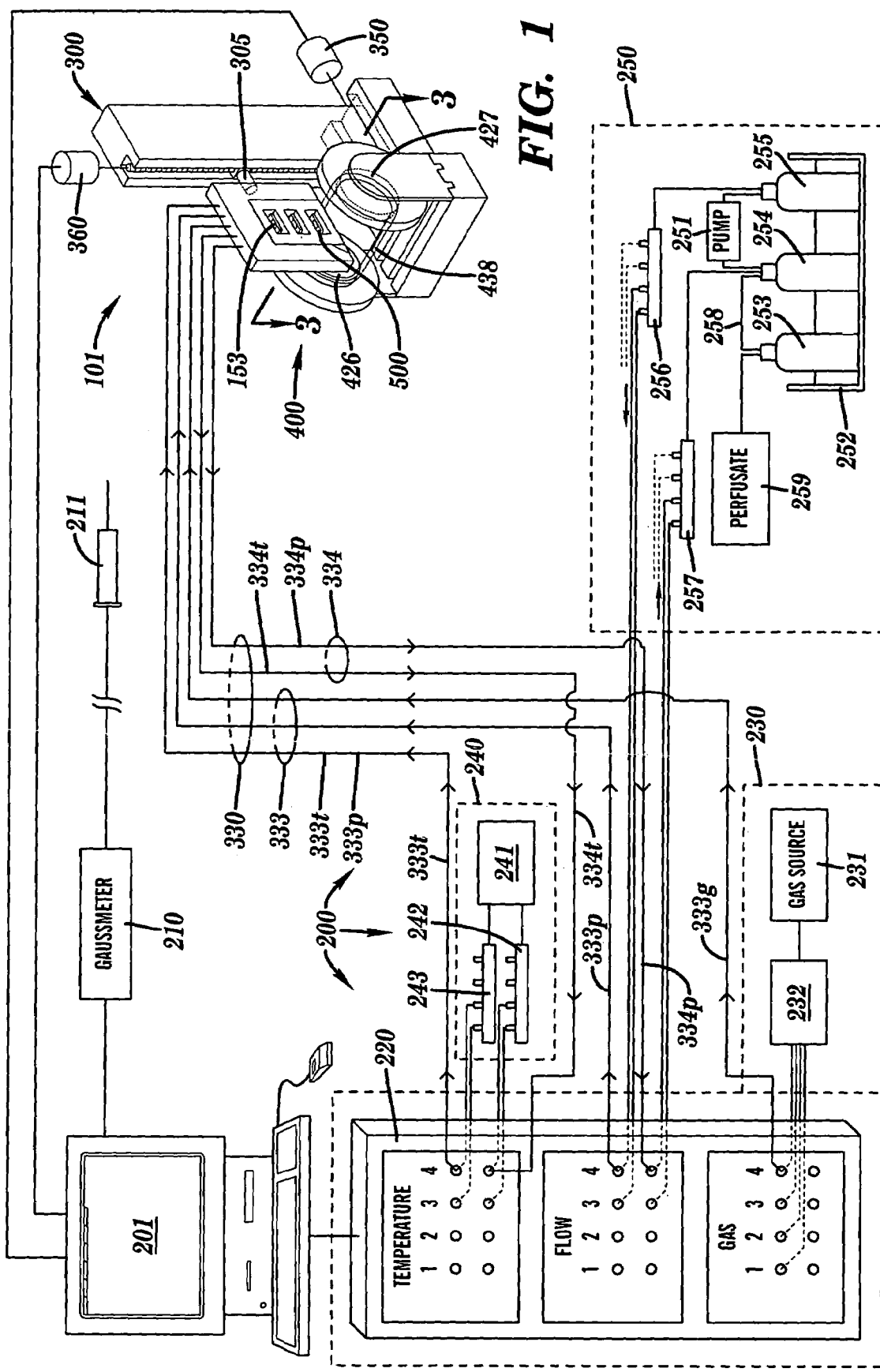
FIG. 1 is a perspective schematic view of a first exemplary embodiment of the invention.
Figure 3:
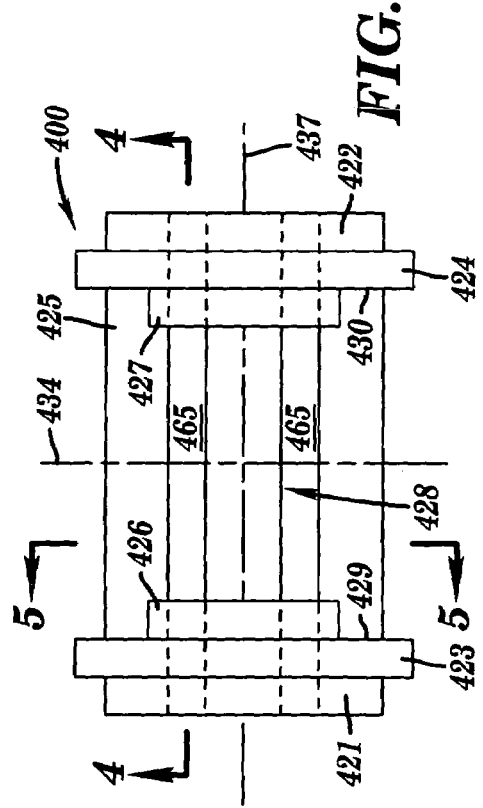
FIG. 3 is a cross-sectional view of a transverse electromagnet of a first exemplary embodiment of the invention taken along line 3-3 of FIG. 1.
Figure 6A:
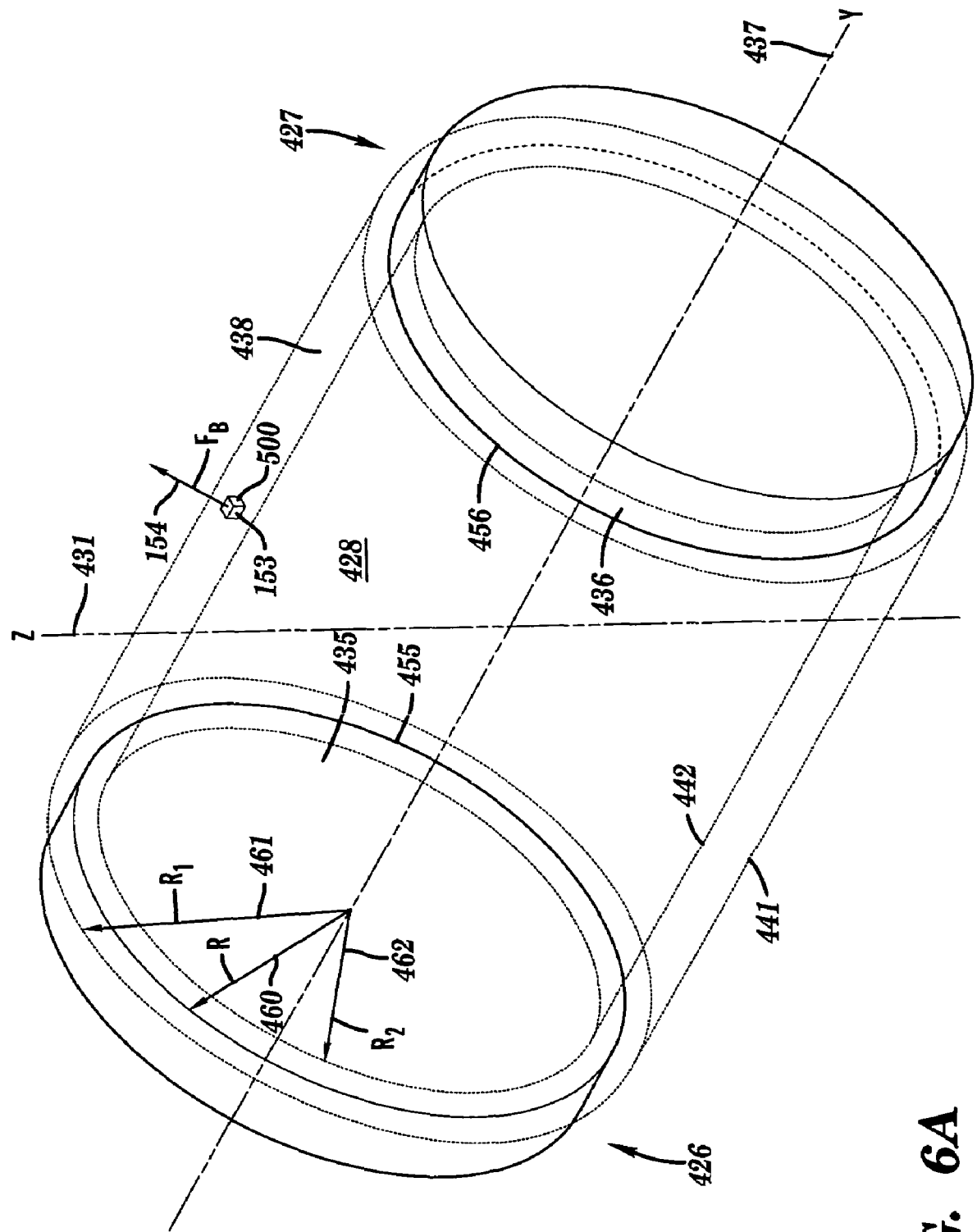

FIG. 6A is a perspective schematic illustration of a region of space between coaxial concentric right circular cylinders extending between circular pole faces and within an air gap of a transverse electromagnet of a first exemplary embodiment of the invention, in which, for the sake of clarity, all of the other elements of first exemplary embodiment of the invention appearing in FIG. 1 and FIG. 3 have been removed.

Figure 6B:
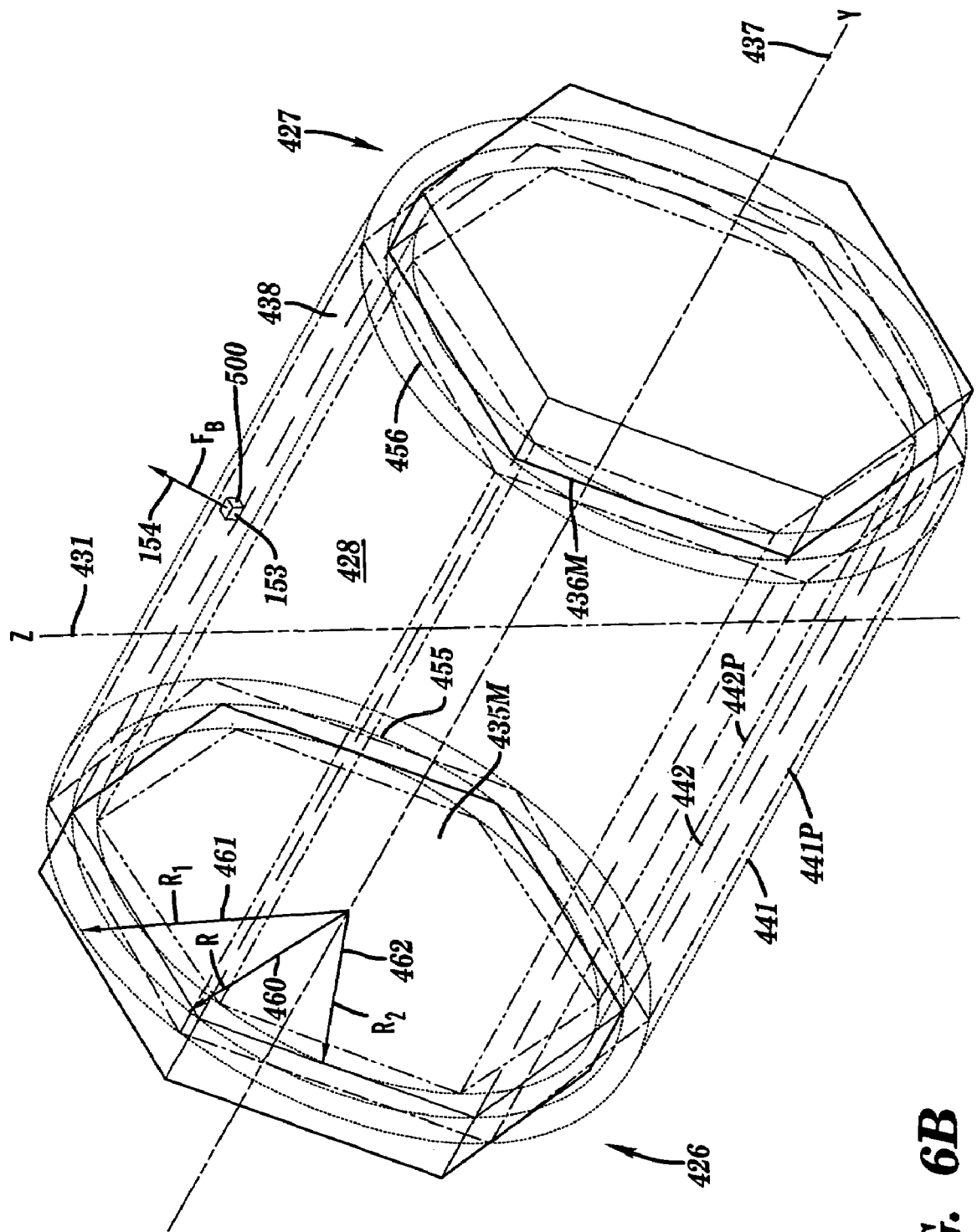

FIG. 6B is a perspective schematic illustration of a region of space between exemplary concentric hexagonal prismatic polyhedrons inscribed in concentric coaxial right circular cylinders extending between modified poles faces and within an air gap of a transverse electromagnet of a first exemplary embodiment of the invention, in which, for the sake of clarity, all of the other elements of first exemplary embodiment of the invention appearing in FIG. 1 and FIG. 3 have been removed.

FIG. 7 is a cross-sectional view of a region of space between coaxial concentric right circular cylinders extending between poles faces and within an air gap of a transverse electromagnet of a first exemplary embodiment of the invention, taken along line 4-4 of FIG. 3 and in which, for the sake of clarity, all of the other elements of first exemplary embodiment of the invention appearing in FIG. 1 and FIG. 3 have been removed.

Figure 8:
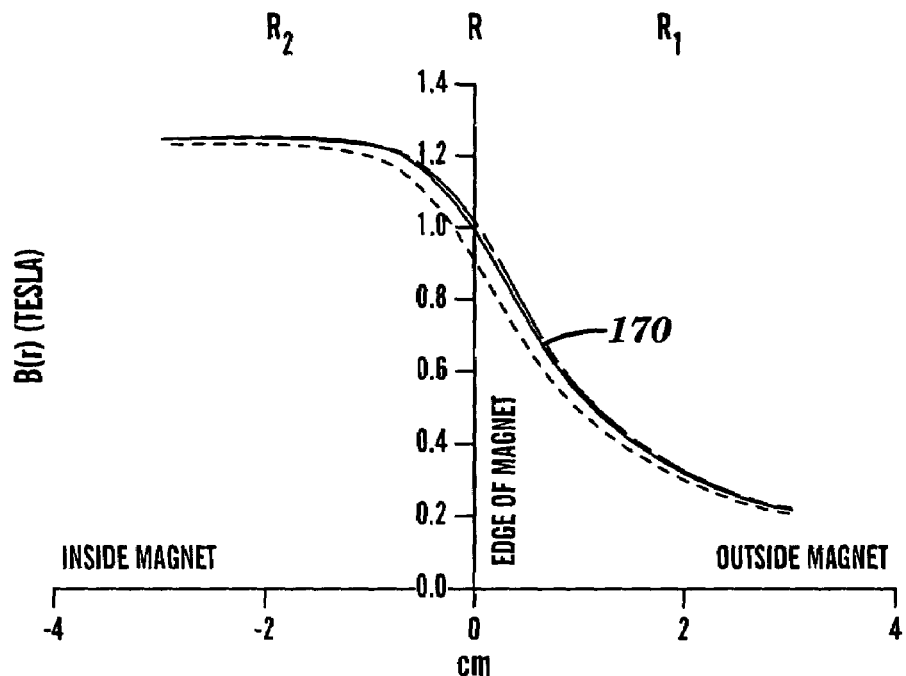

FIG. 8 is an illustrative graph of the radial variation of the magnitude of a magnetic field inductance the in a region of space in the vicinity of a circular margin of either magnetic pole face of a transverse electromagnet of a first exemplary embodiment of the invention.

Figure 9:
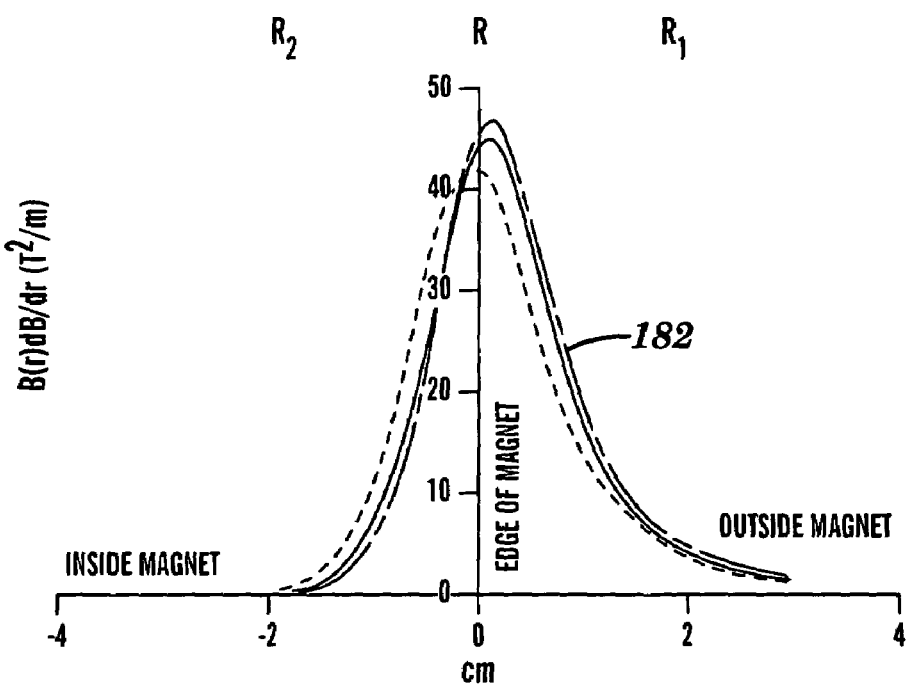

FIG. 9 is an illustrative graph of the radial variation of the magnitude of the magnetic field-field gradient product in a region of space in the vicinity of a circular margin of either magnetic pole face of a transverse electromagnet of a first exemplary embodiment of the invention.

Figure 10:
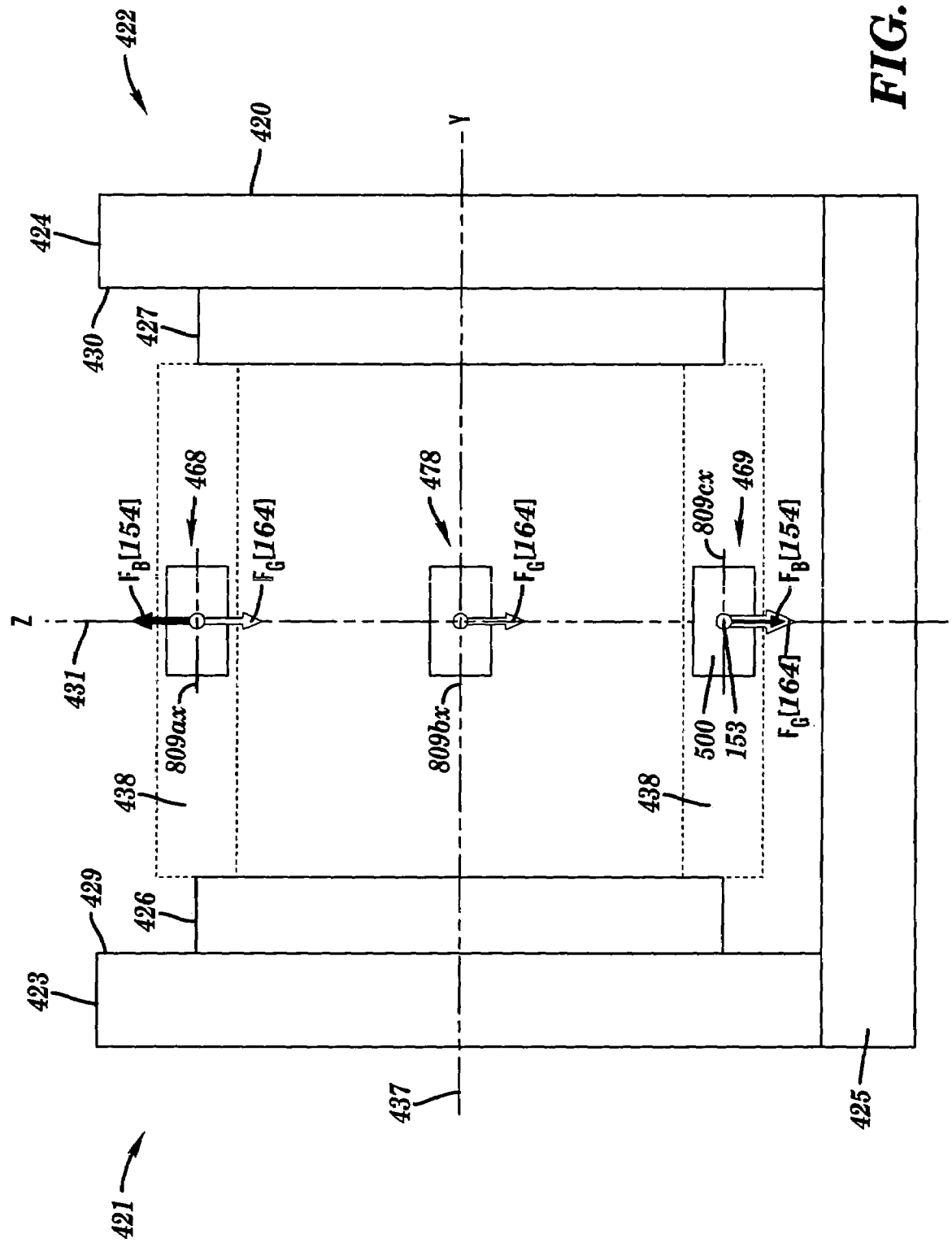

FIG. 10 is a cross-sectional view of a transverse electromagnet taken along line 4-4 of FIG. 3, illustrating the interaction of a diamagnetic body force with a force of gravity at different locations in a first exemplary embodiment of the invention.

Figure 11:
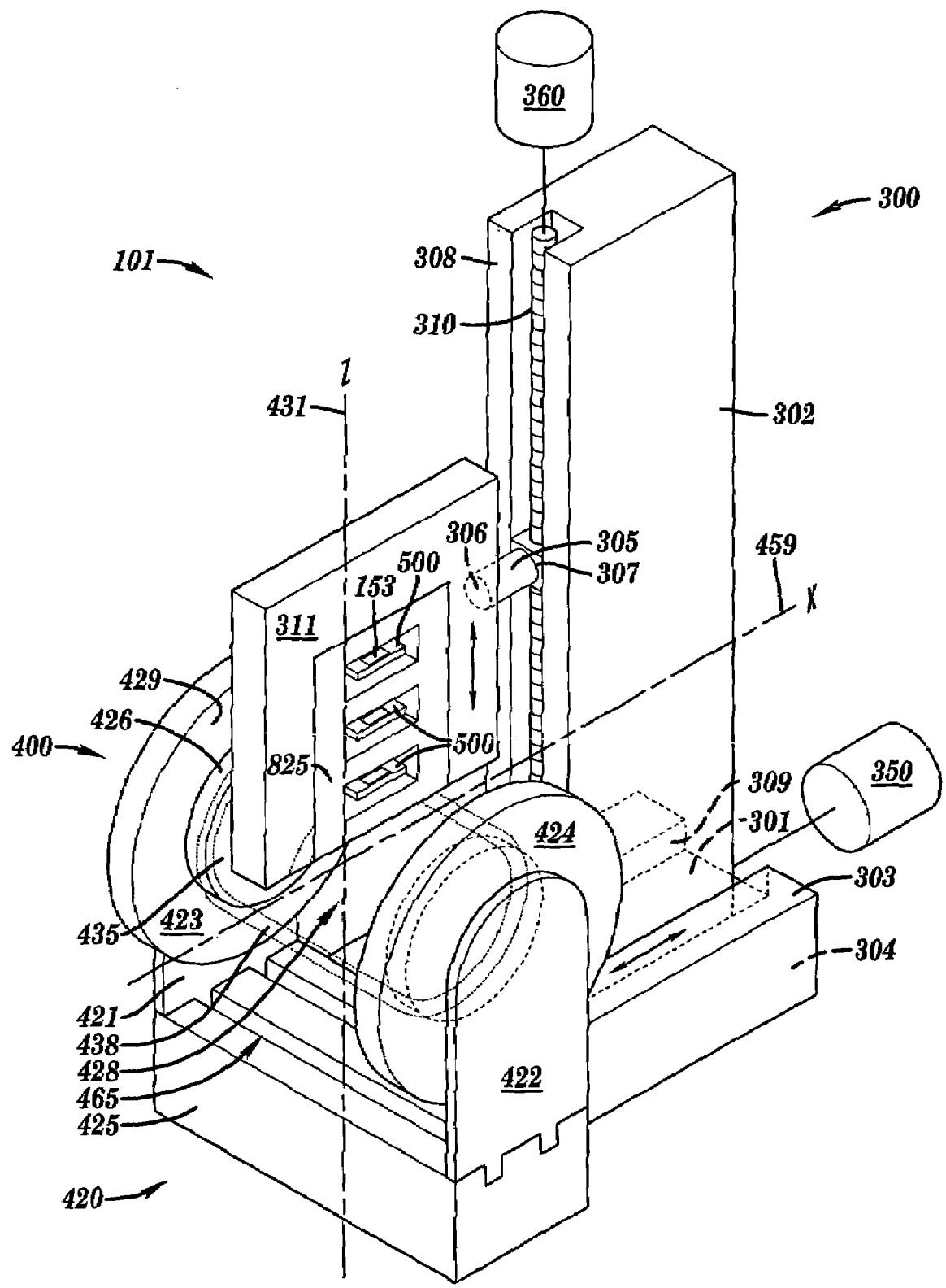

FIG. 11 is a more detailed perspective schematic view of a first exemplary embodiment of the invention, with its in vitro support systems interface and in vitro support system omitted.

Figure 12:
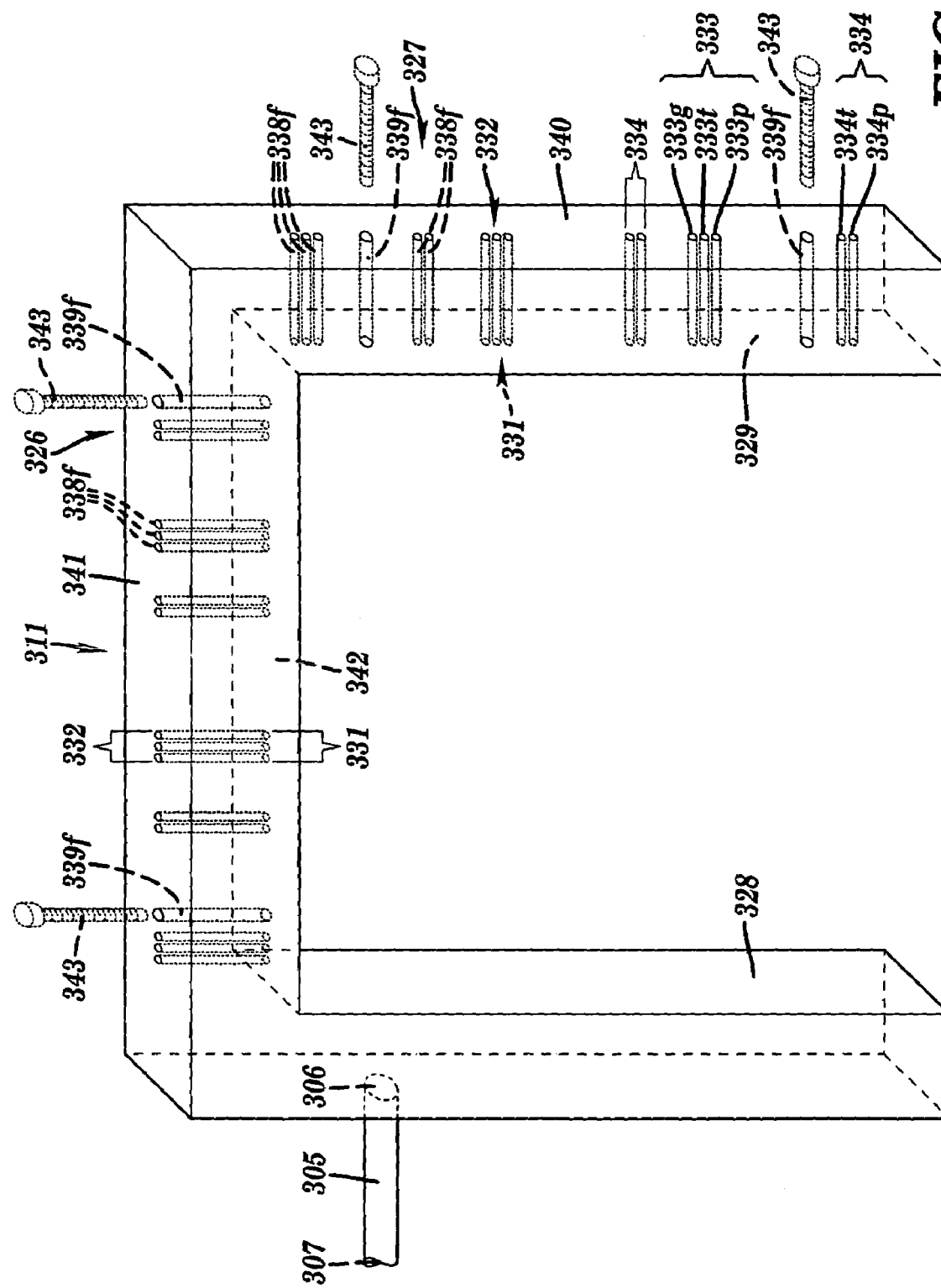

FIG. 12 is a schematic perspective illustration of an exemplary rectilinear frame of a first exemplary embodiment of a bioreactor chamber support system of a first exemplary embodiment of the invention.

Figure 13:
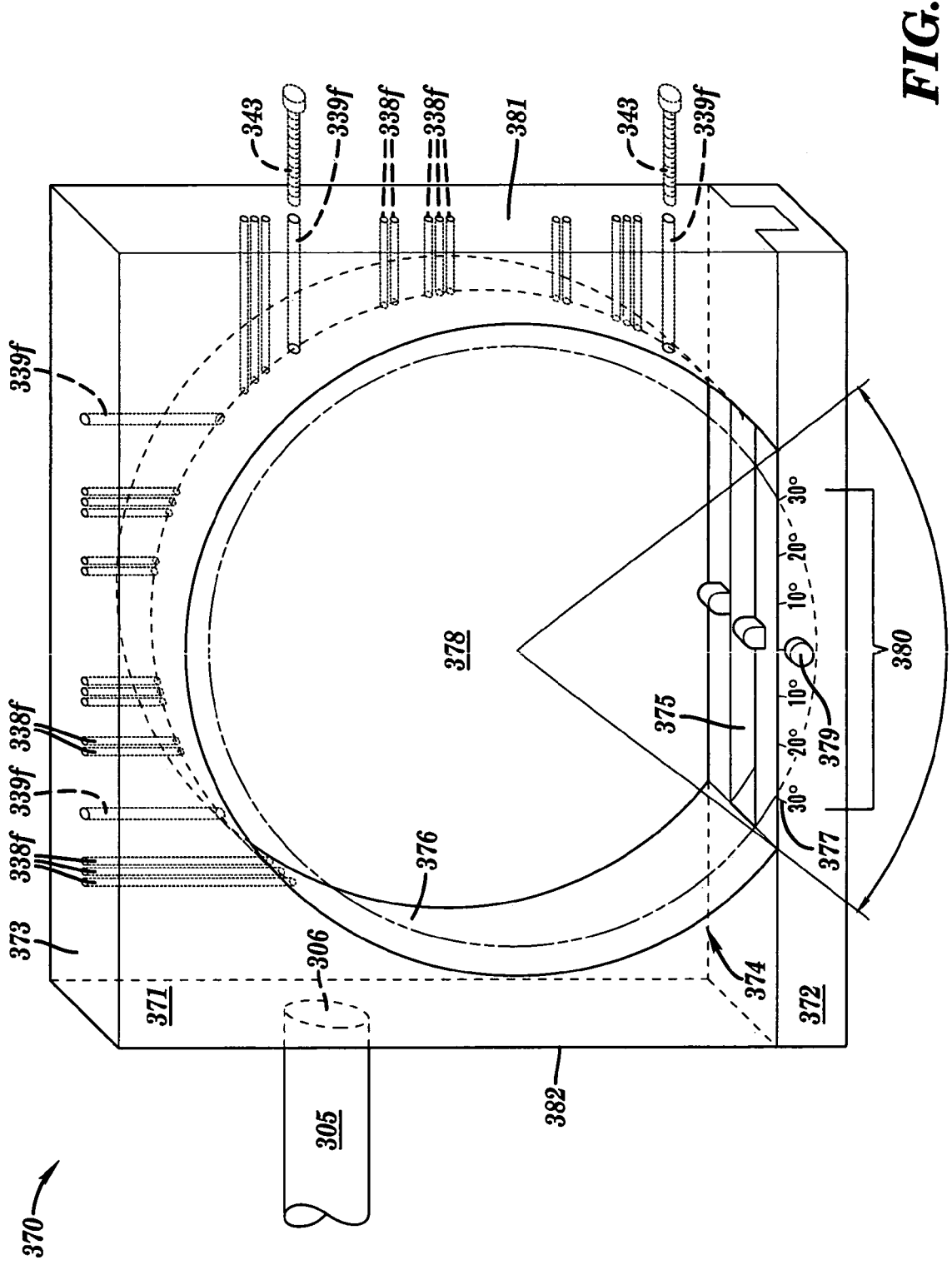

FIG. 13 is a schematic perspective illustration of an exemplary circular frame of a first exemplary embodiment of a bioreactor chamber support system of a first exemplary embodiment of the invention.

Figure 14:
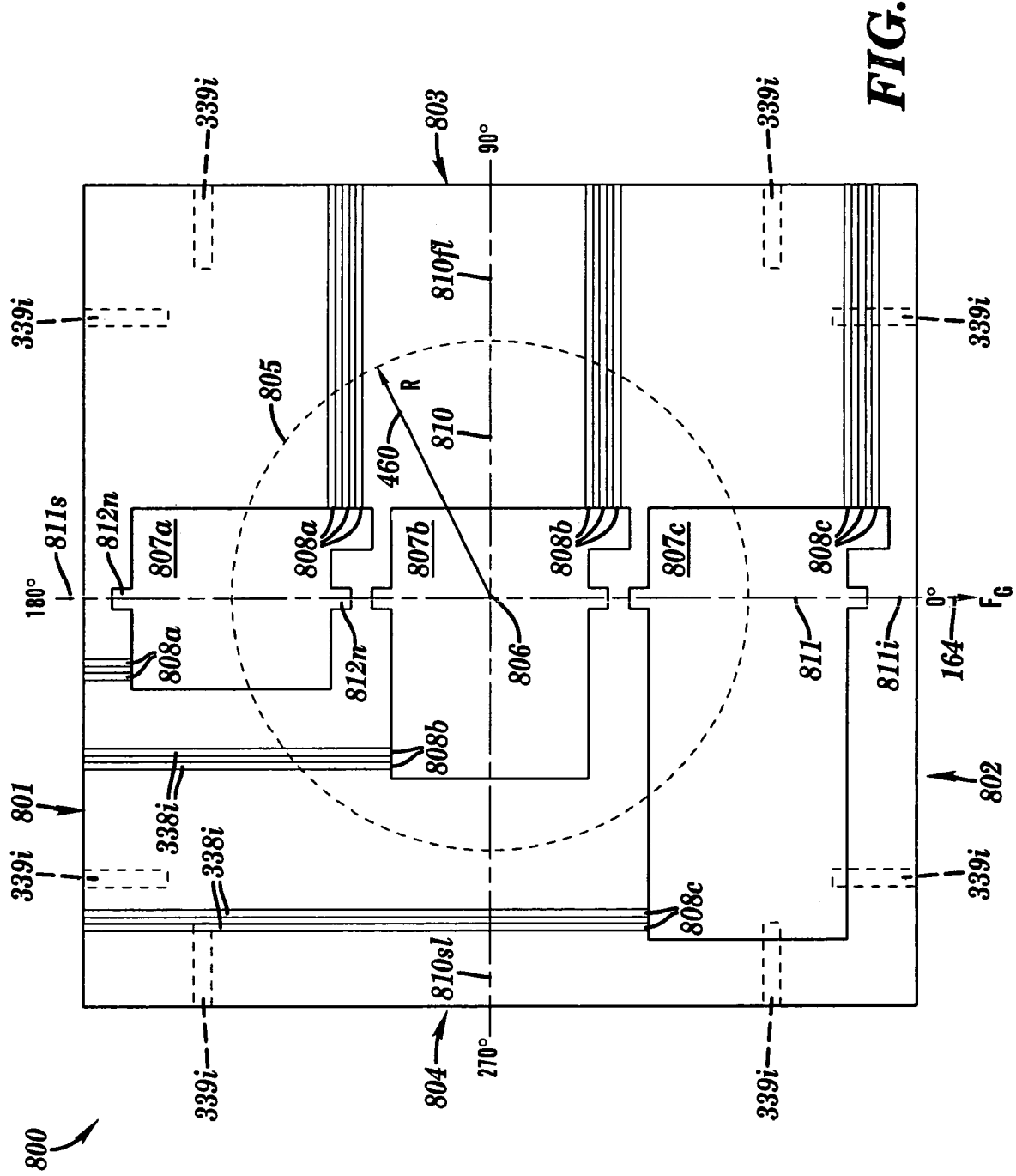

FIG. 14 is a schematic illustration of an exemplary radially slotted rectilinear insert for use with an exemplary rectilinear frame shown in FIG. 12.

Figure 15:
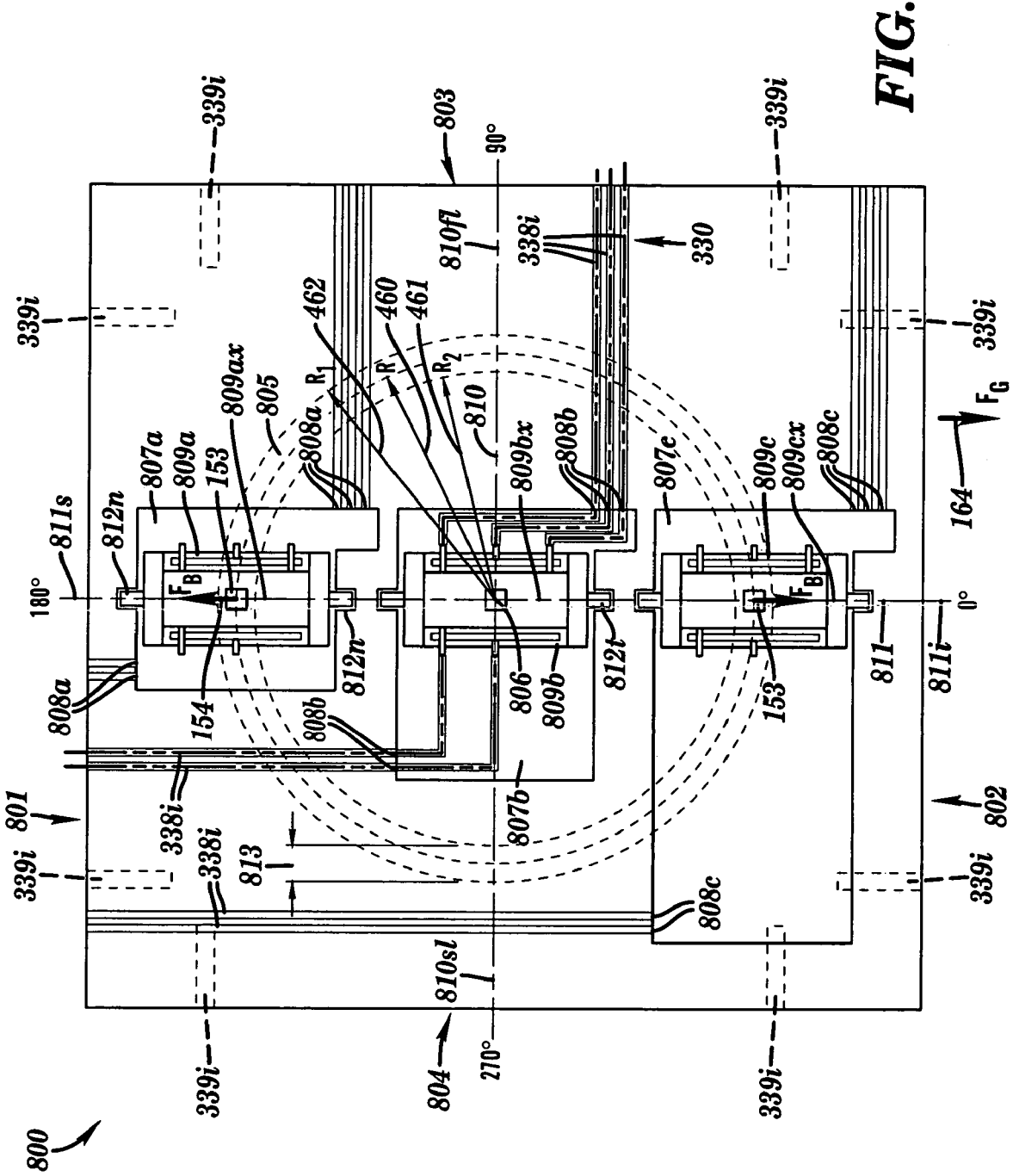

FIG. 15 is a schematic illustration of an exemplary radially slotted rectilinear insert with exemplary bioreactor chambers for use with an exemplary rectilinear frame shown in FIG. 12.

Figure 16:
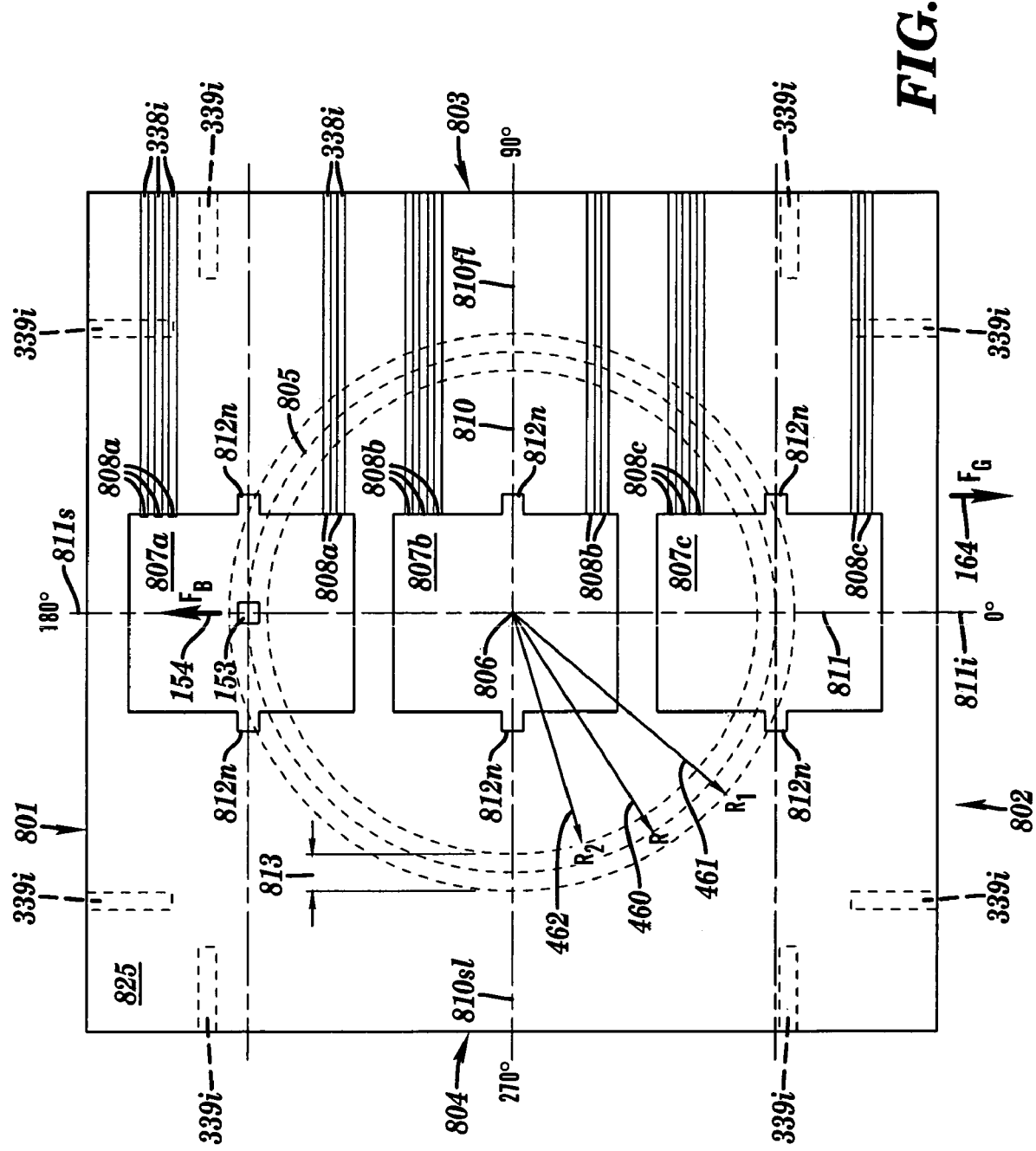

FIG. 16 is a schematic illustration of an exemplary tangentially slotted rectilinear insert for use with an exemplary rectilinear frame shown in FIG. 12.

Figure 17:
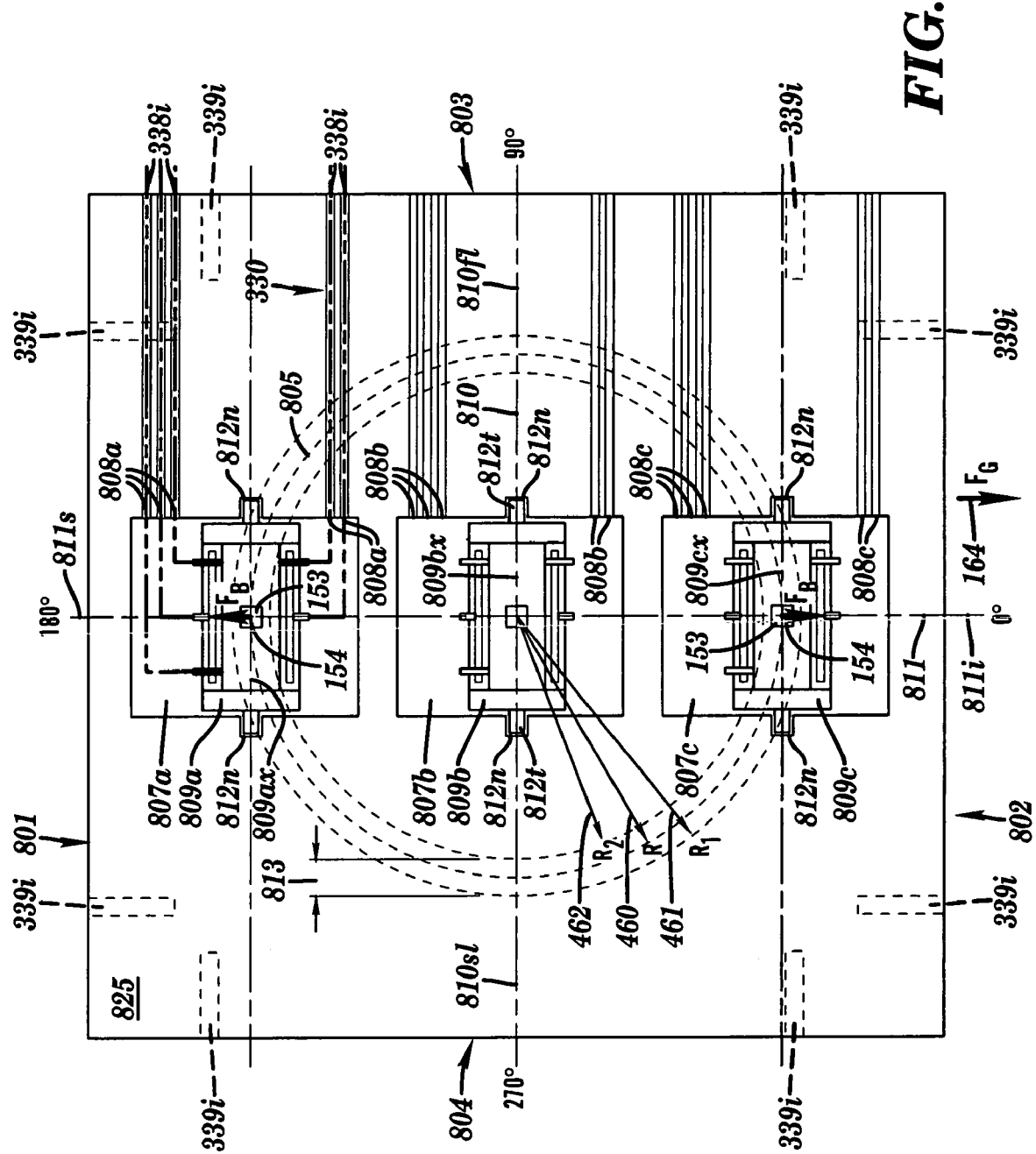

FIG. 17 is a schematic illustration of an exemplary tangentially slotted rectilinear insert with exemplary bioreactor chambers for use with an exemplary rectilinear frame shown in FIG. 12.

Figure 18:
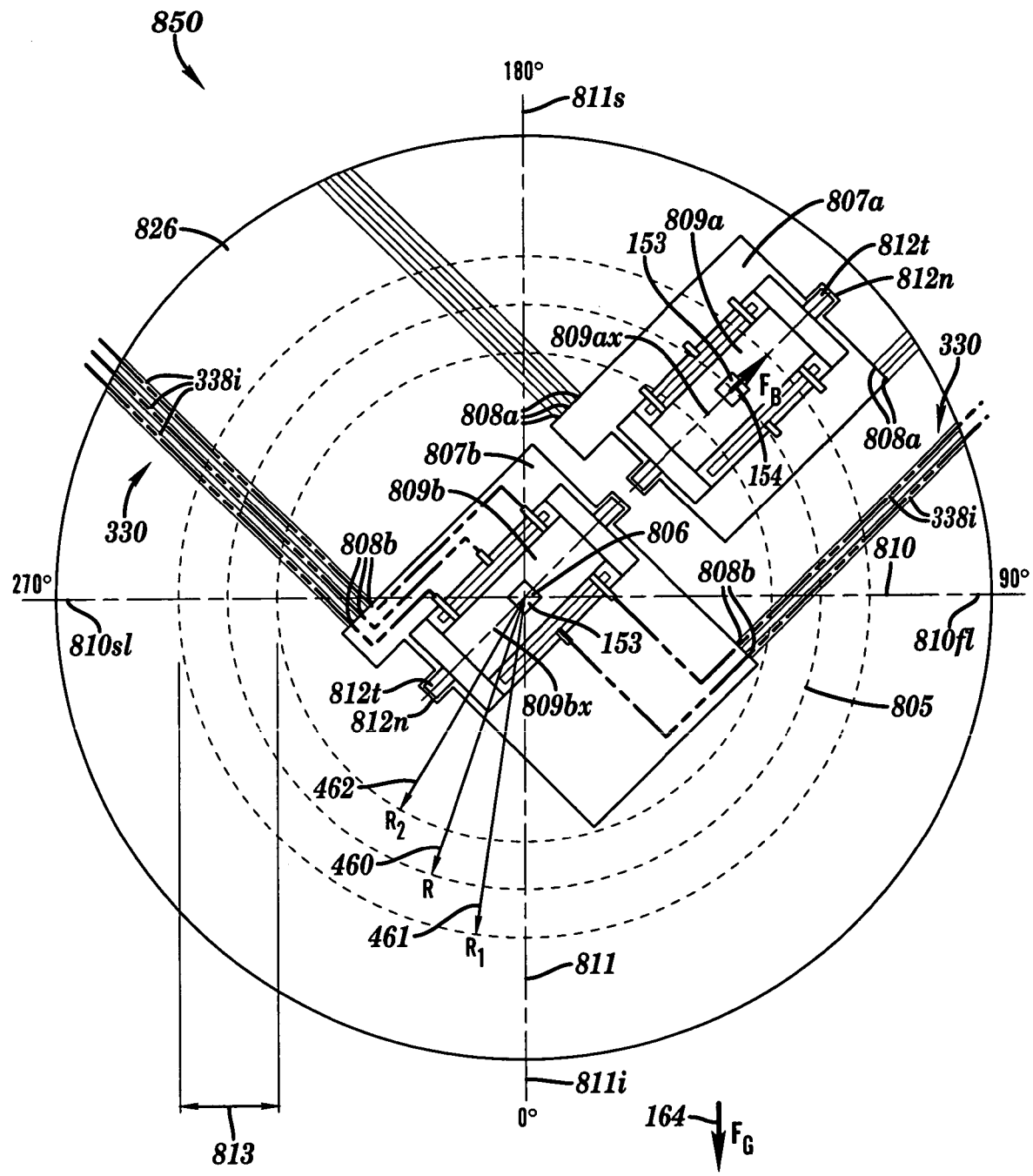

FIG. 18 is a schematic illustration of an exemplary radially slotted circular insert with exemplary bioreactor chambers for use with an exemplary circular frame shown in FIG. 13.

Figure 19:
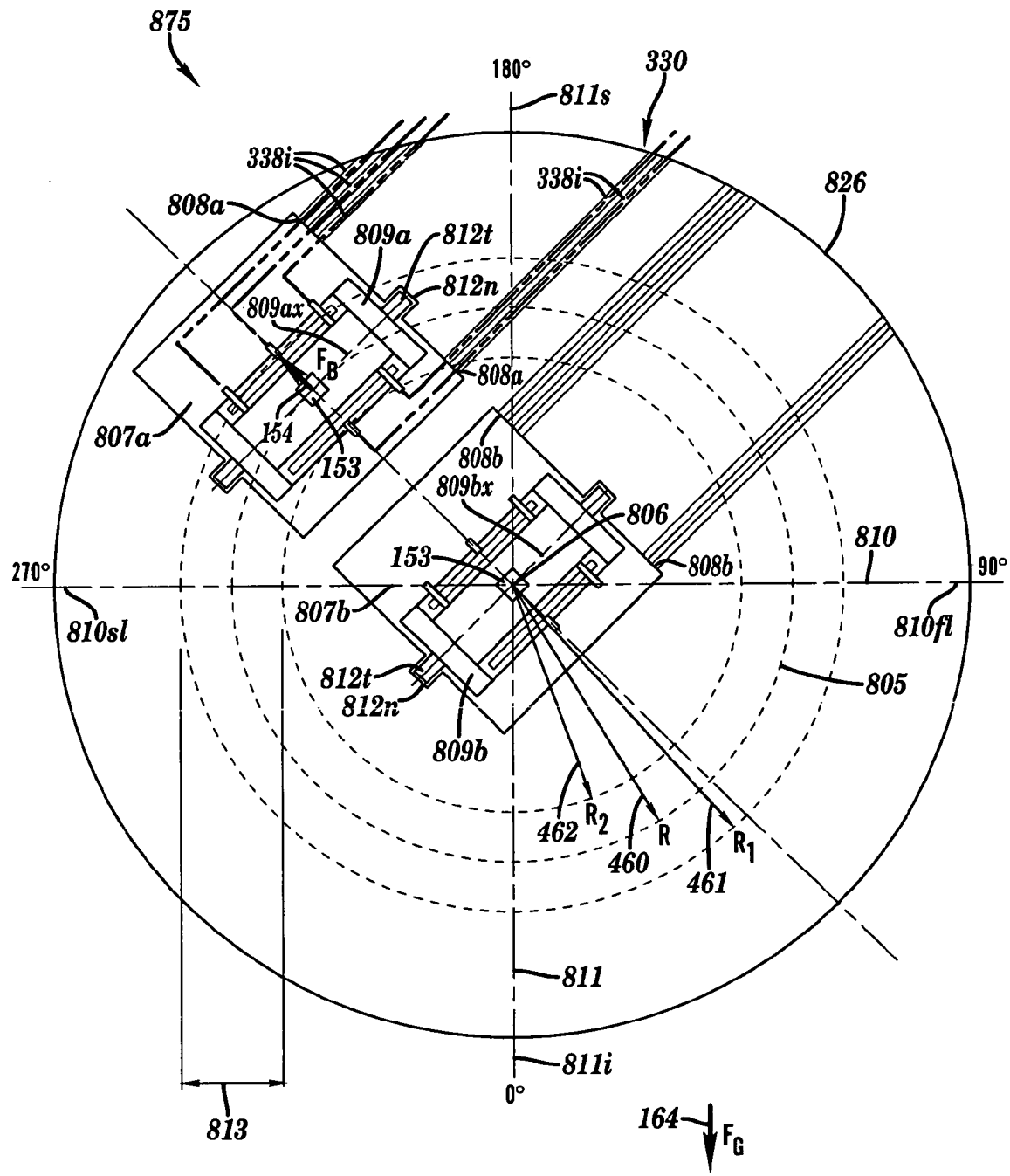

FIG. 19 is a schematic illustration of an exemplary tangentially slotted circular insert with exemplary bioreactor chambers for use with an exemplary circular frame shown in FIG. 13.

Figure 20A:
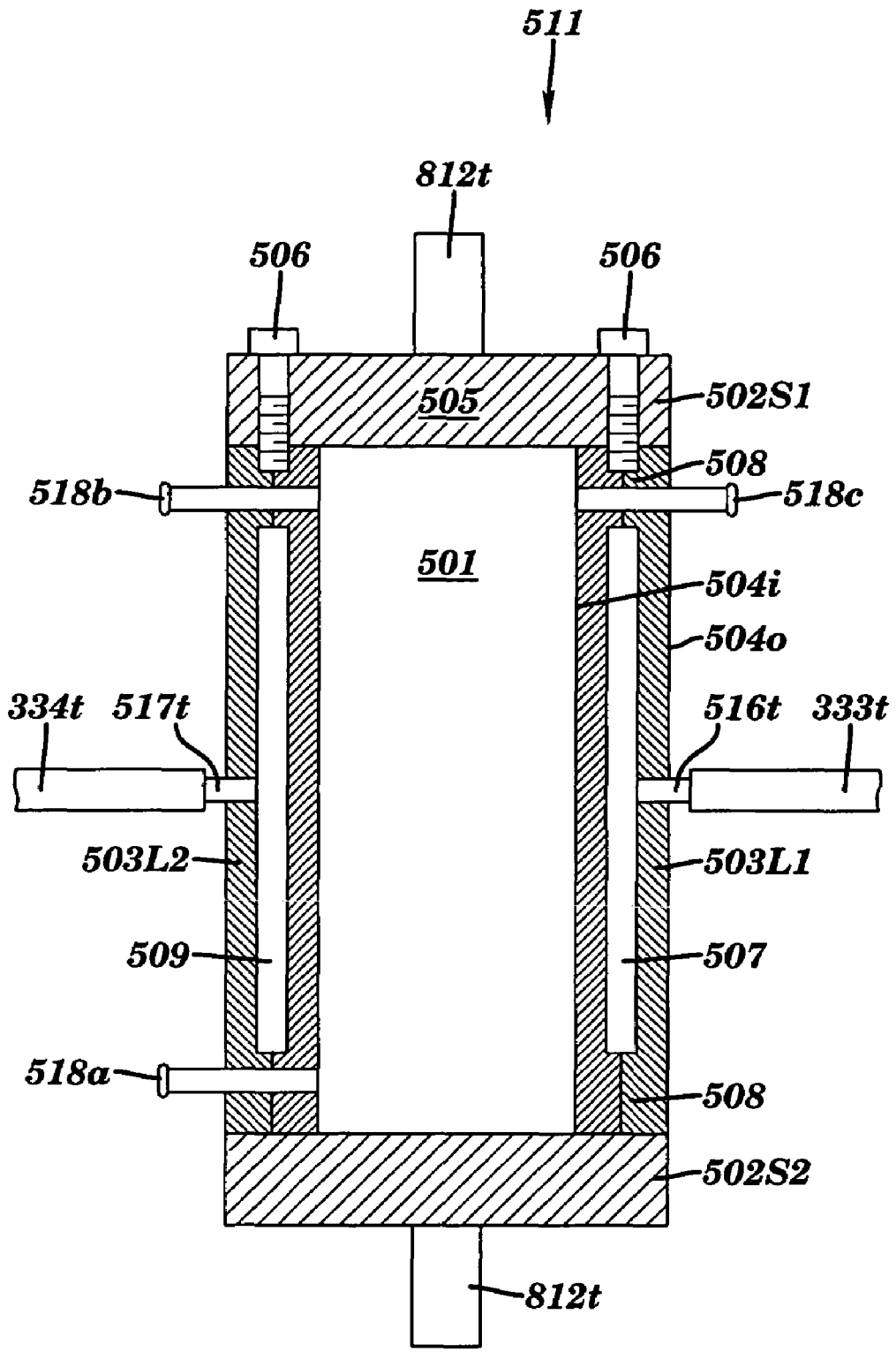

FIG. 20A is a schematic cross-sectional view of a body common to all exemplary bioreactor chambers.

FIG. 20A1 is a less detailed schematic cross-sectional view of exemplary common body of FIG. 20, showing a plurality of parallel inwardly projecting ledges for the carriage of biological specimens.

FIG. 20A2 is a less detailed schematic cross-sectional view of exemplary common body of FIG. 20, along line 20A2-20A2 of FIG. 20A1.

Figure 20B:
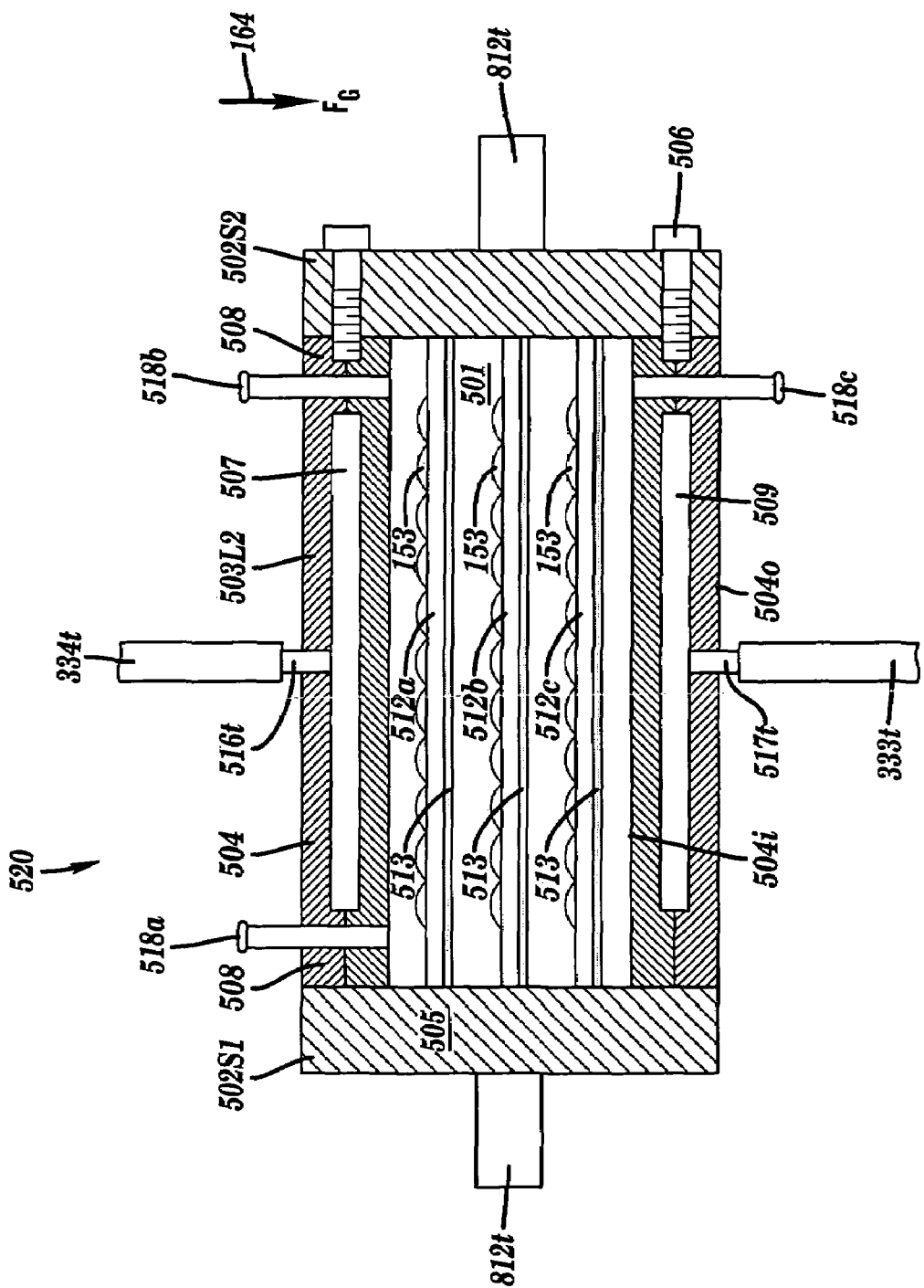

FIG. 20B is a schematic cross-sectional view of an exemplary tangential 2-D static bioreactor chamber.

Figure 20C:
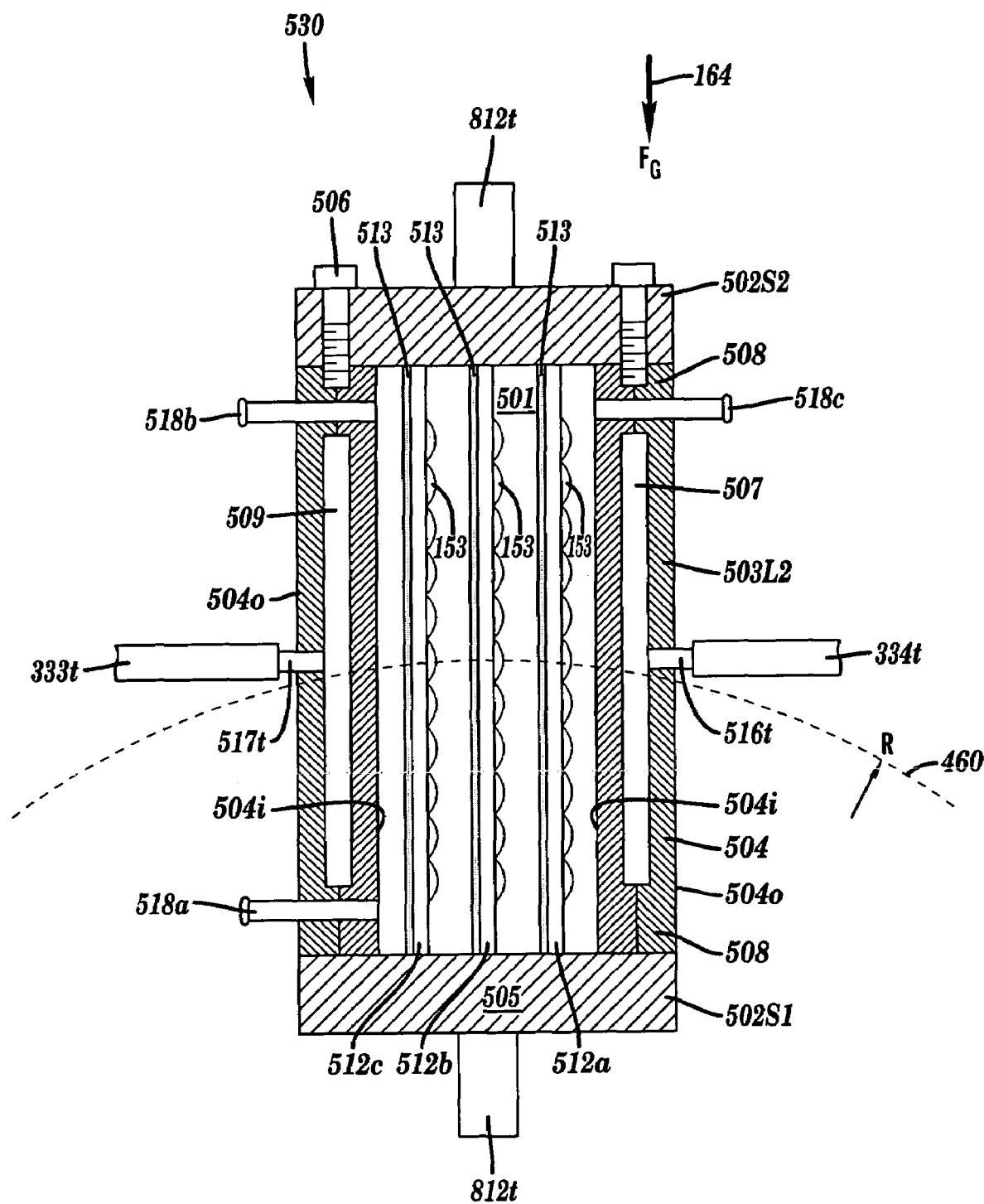

FIG. 20C is a schematic cross-sectional view of an exemplary radial 2-D static bioreactor chamber.

FIG. 20D is a perspective schematic view of a flow insert used to modify the internal volume of a common body shown in FIG. 20A.

FIG. 20D1 shows common body of FIG. 20A1 with plurality of parallel inwardly projecting ledges removed and replaced by the flow insert of FIG. 20D.

FIG. 20D2 shows common body of FIG. 20A2 with plurality of parallel inwardly projecting ledges removed and replaced by the flow insert of FIG. 20D.

FIG. 20E is a cross-sectional view of an exemplary 2-D normal-flow bioreactor chamber.

Figure 20F:
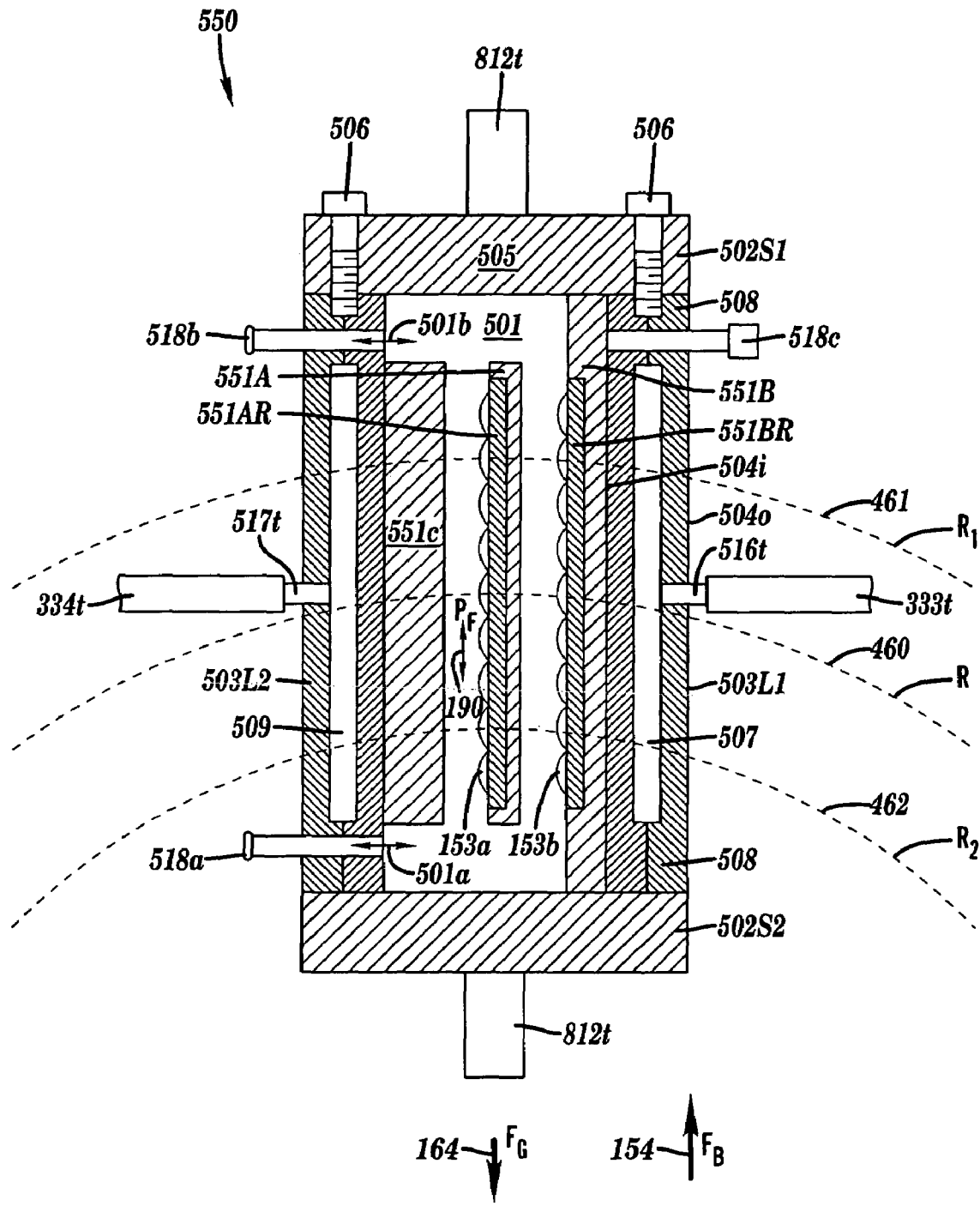

FIG. 20F is a cross-sectional view of an exemplary 2-D parallel-flow bioreactor chamber.

Figure 20G:
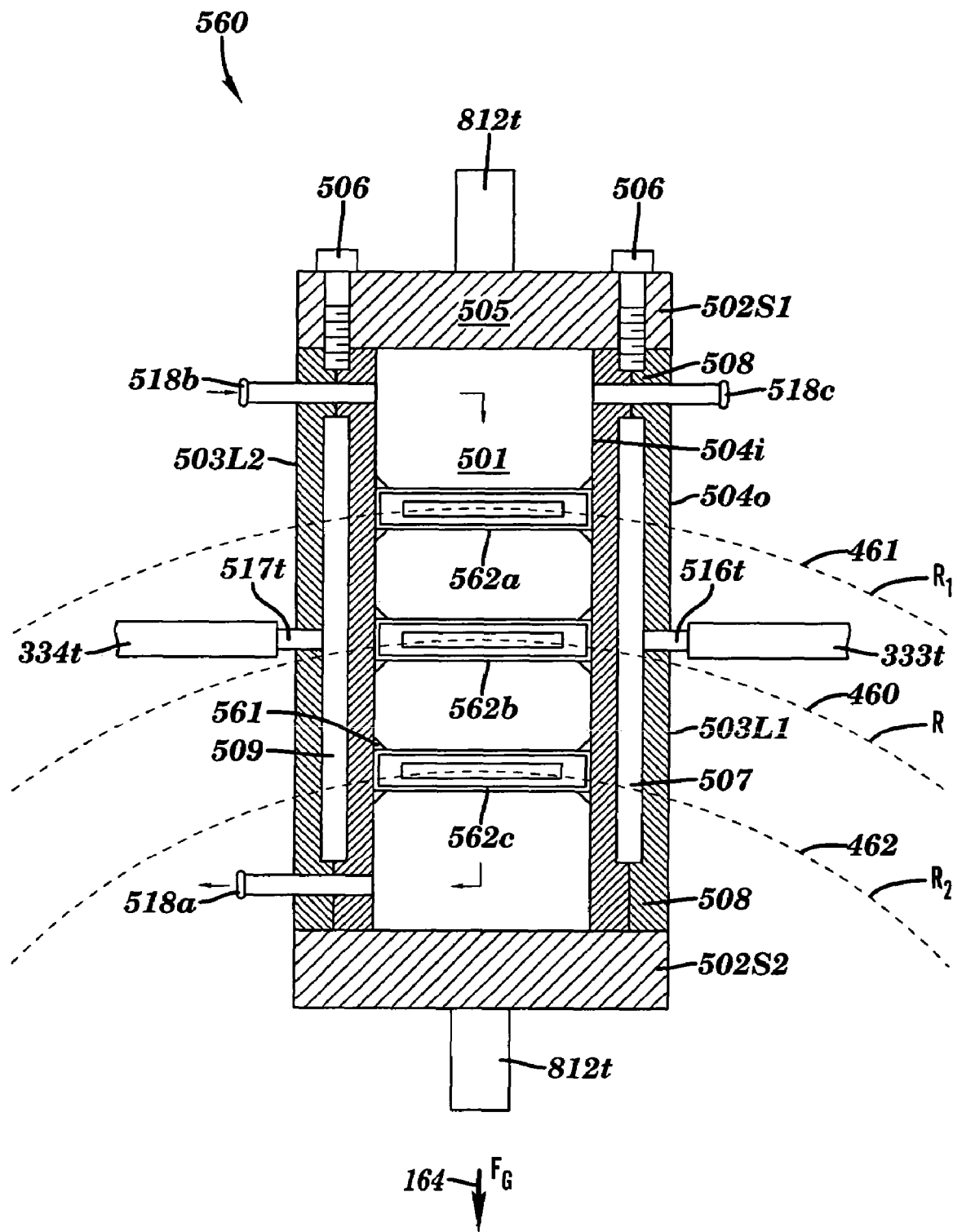

FIG. 20G is a cross-sectional view of an exemplary 3-D bioreactor chamber.

Figure 21:
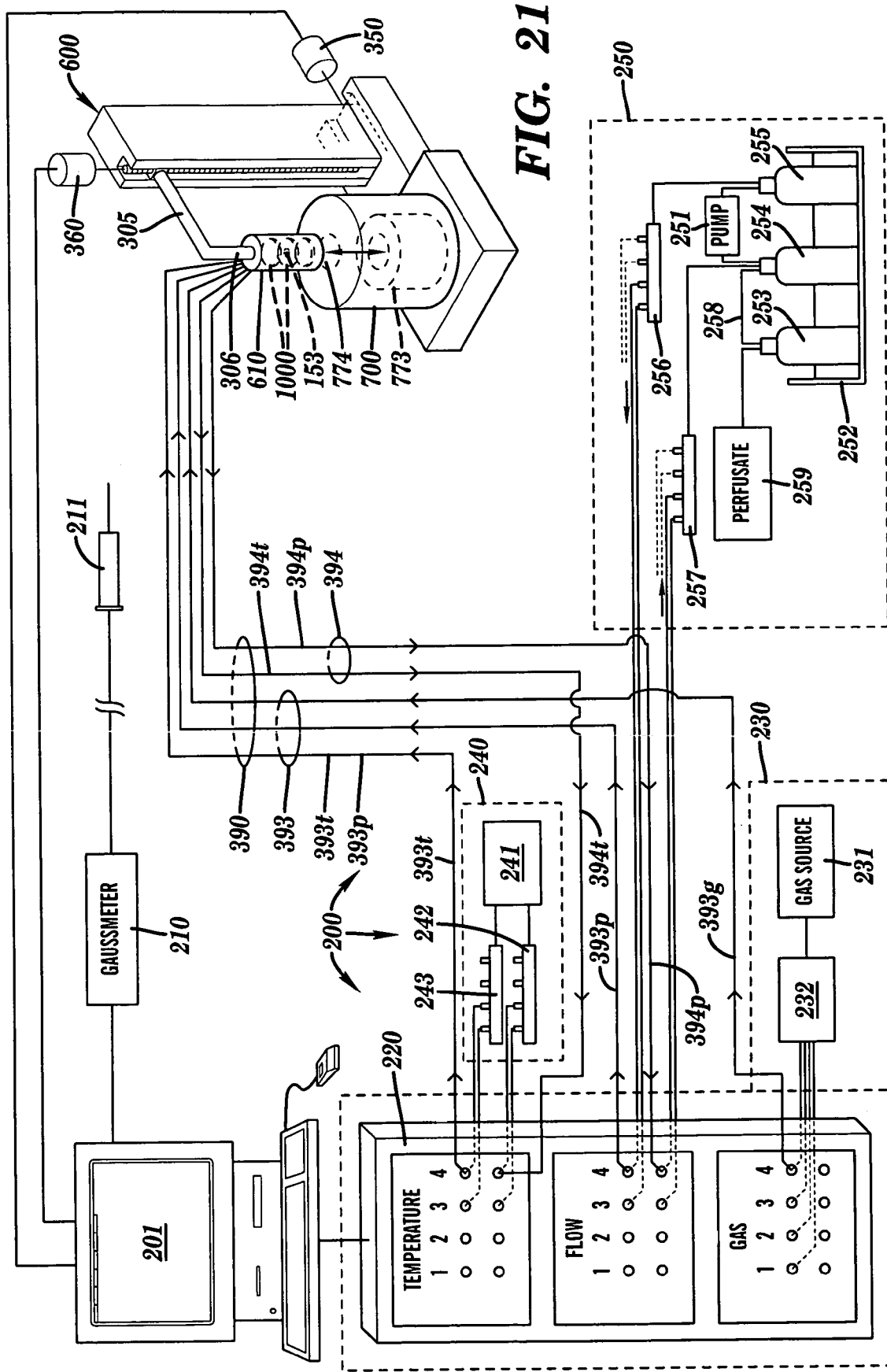

FIG. 21 is a perspective schematic view of a second exemplary embodiment of the invention.

FIG. 22A shows a schematic perspective illustration of a vertically oriented superconducting solenoid magnet in a cylindrical coordinate system in whose bore there is a core cylinder of space.

FIG. 22B shows a schematic cross sectional view of a superconducting solenoid magnet taken along line 22B-22B of FIG. 22A.

Figure 23B:
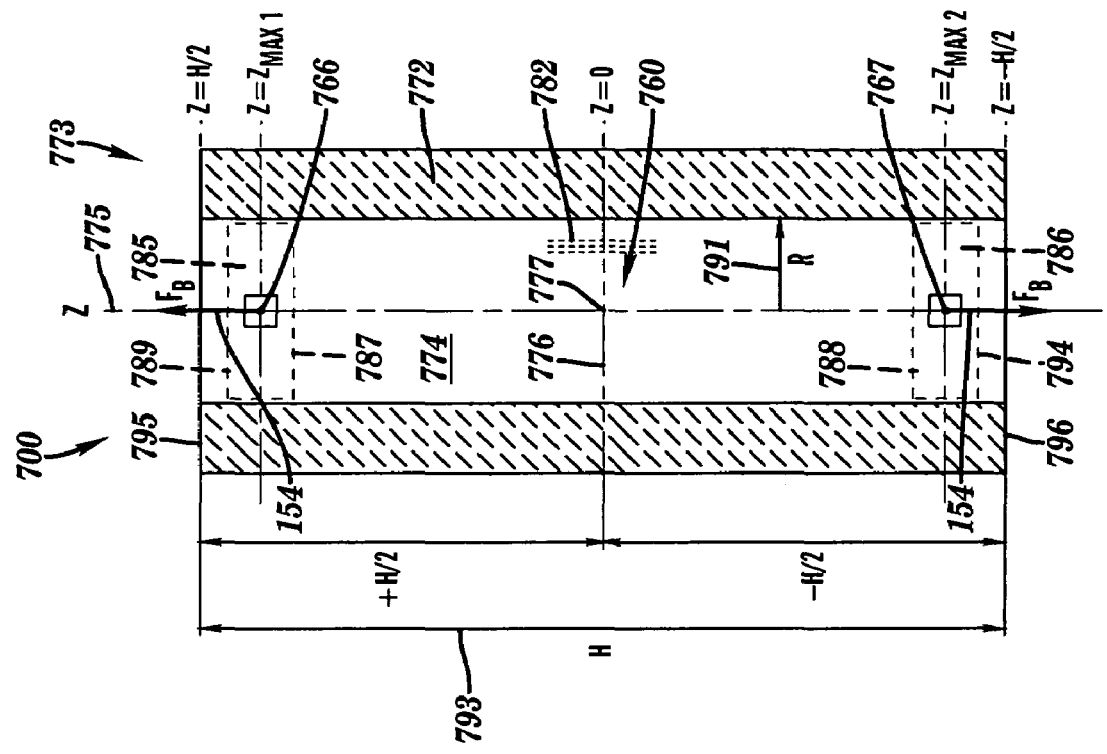
Figure 23A:
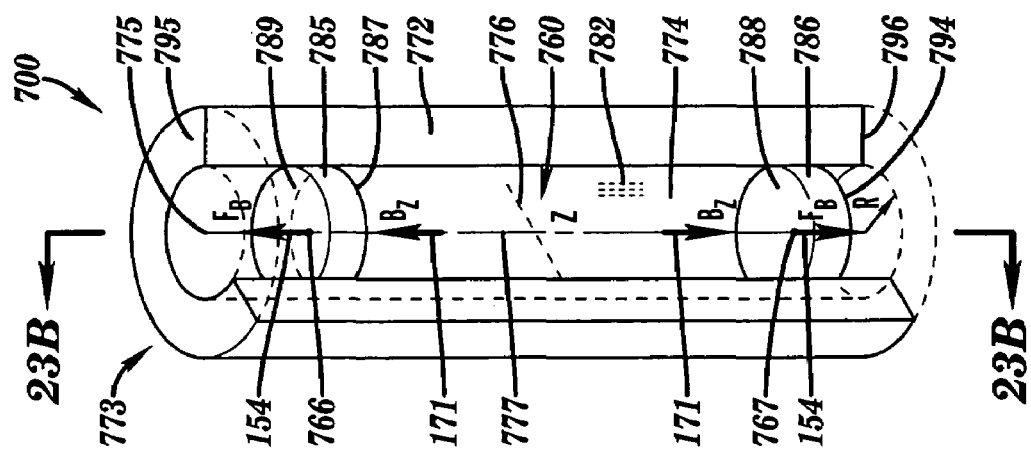

FIG. 23A shows a schematic perspective illustration of a vertically oriented superconducting solenoid magnet in a cylindrical coordinate system in whose bore there is a core cylinder of space containing cylindrical segments.

FIG. 23B shows a schematic cross sectional view of a superconducting solenoid magnet taken along line 23B-23B of FIG. 23A.

Figure 24A:
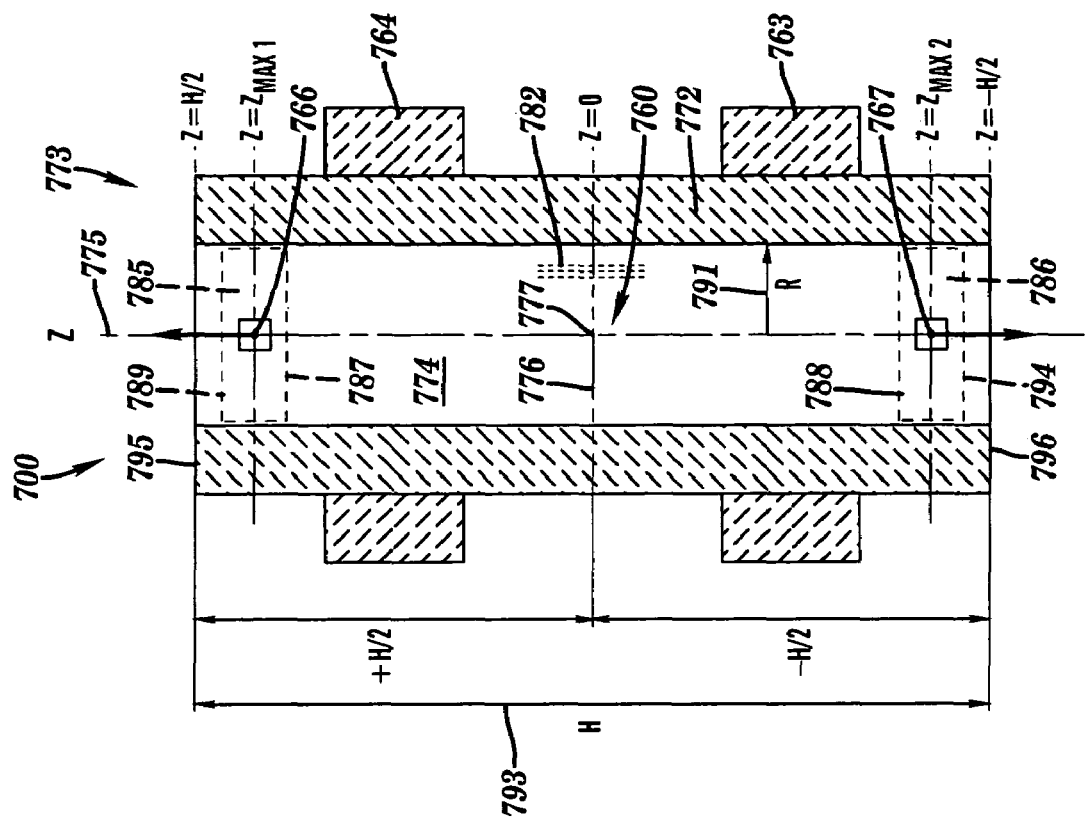

FIG. 24A is a schematic cross-sectional illustration of the vertically oriented superconducting solenoid magnet of FIG. 22B with the addition of exemplary first and second gradient coils.

Figure 24B:
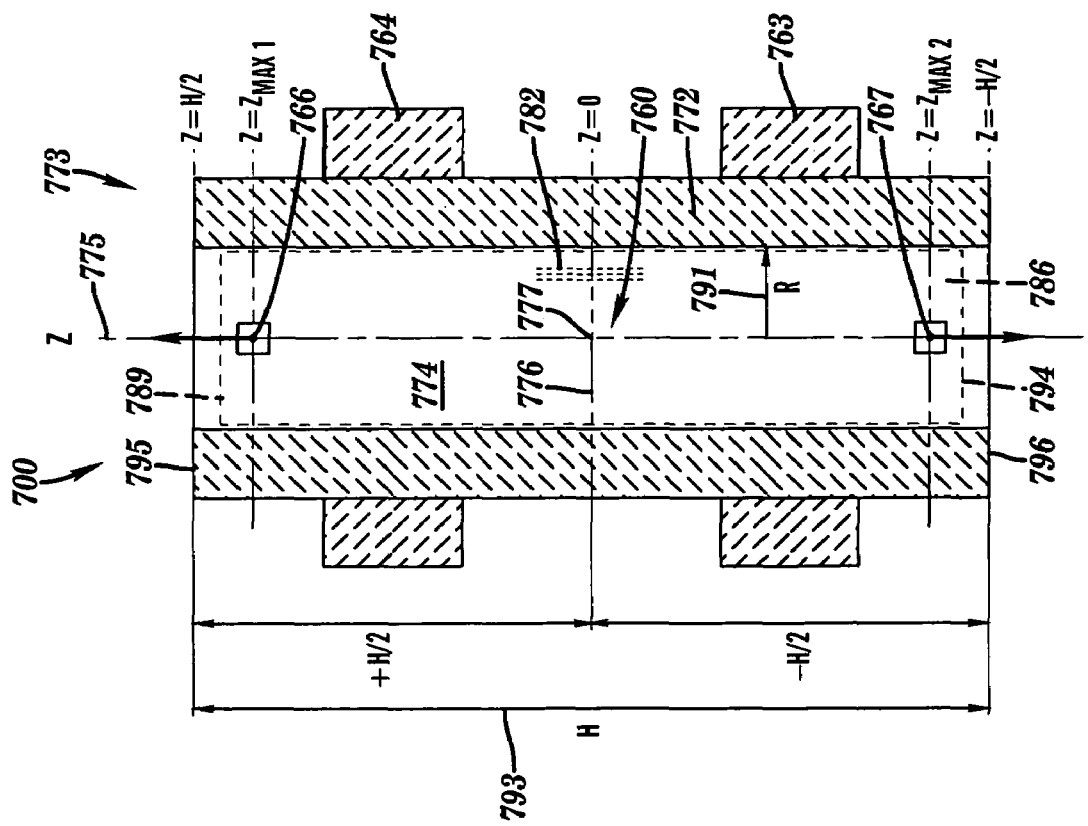

FIG. 24B is a schematic cross-sectional illustration of the vertically oriented superconducting solenoid magnet of FIG. 23B with the addition of exemplary first and second gradient coils.

Figure 25:
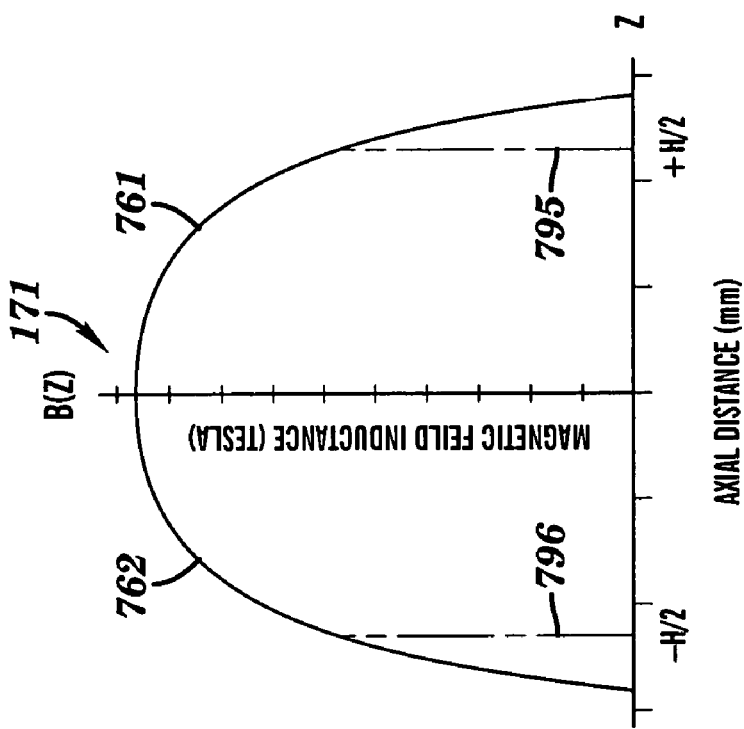

FIG. 25 is a graph of an axial profile of an exemplary magnetic field inductance B(z) in a right circular cylindrical superconducting solenoid.

Figure 26:
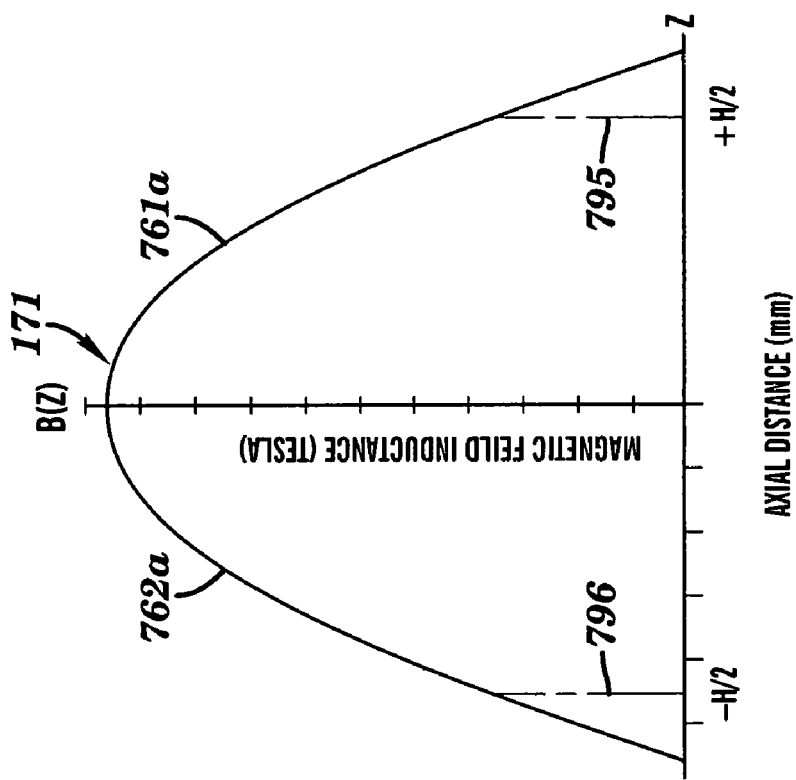

FIG. 26 is a graph of an axial profile of an exemplary gradient coil-enhanced magnetic field inductance B(z) in a right circular cylindrical superconducting solenoid.

FIG. 27 is a graph of an exemplary magnetic field gradient $\partial B(z)/\partial z$ in a right circular cylindrical superconducting solenoid.

FIG. 28 is a graph of an exemplary magnetic field-field gradient product $B(z)\partial B/\partial z$ in a right circular cylindrical superconducting solenoid.

Figure 29:
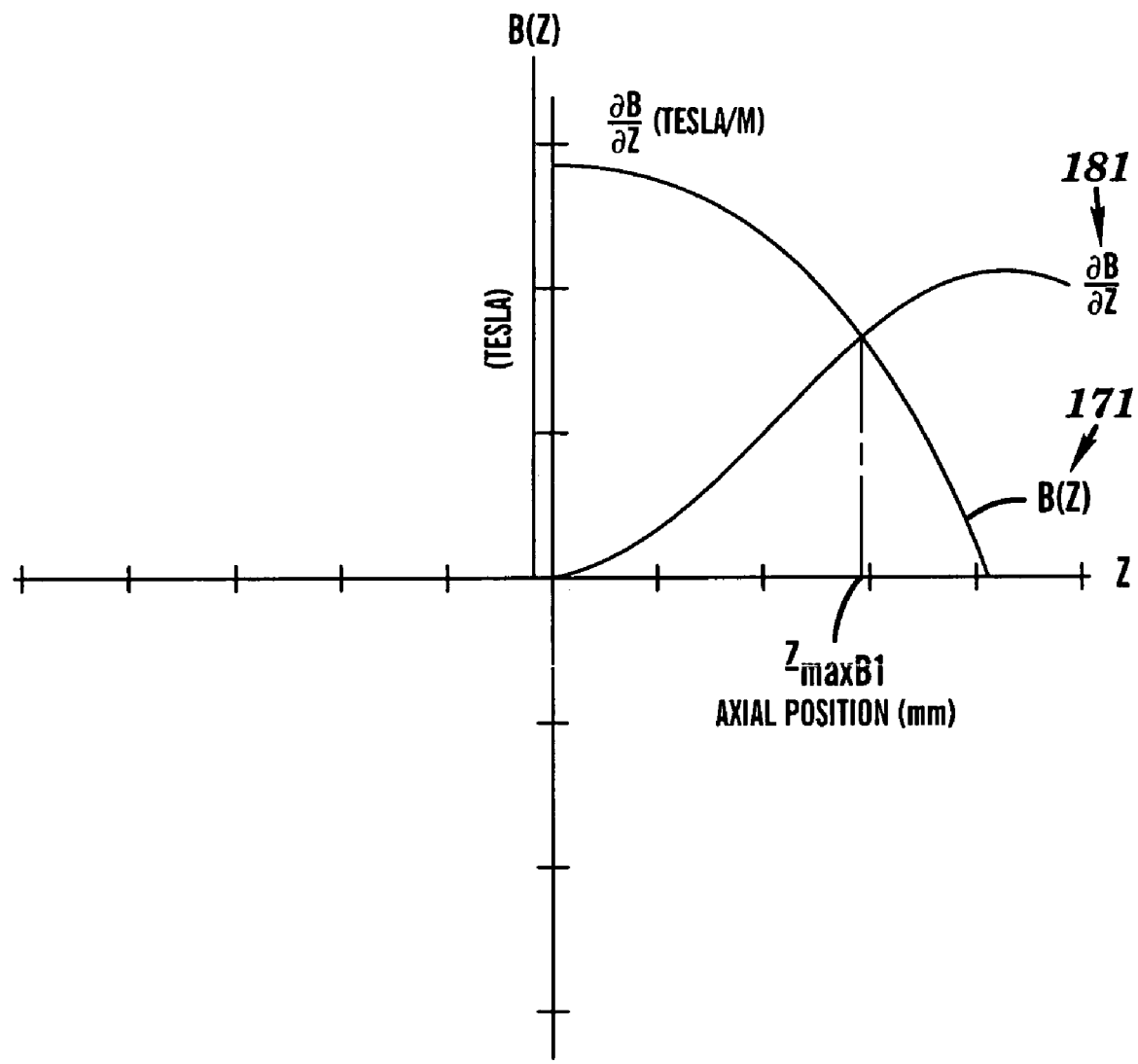

FIG. 29 is a graph showing an exemplary point of intersection of an exemplary magnetic field inductance B(z) with an exemplary magnetic field gradient $\partial B(z)/\partial z$ in a right circular cylindrical superconducting solenoid.

Figure 30:
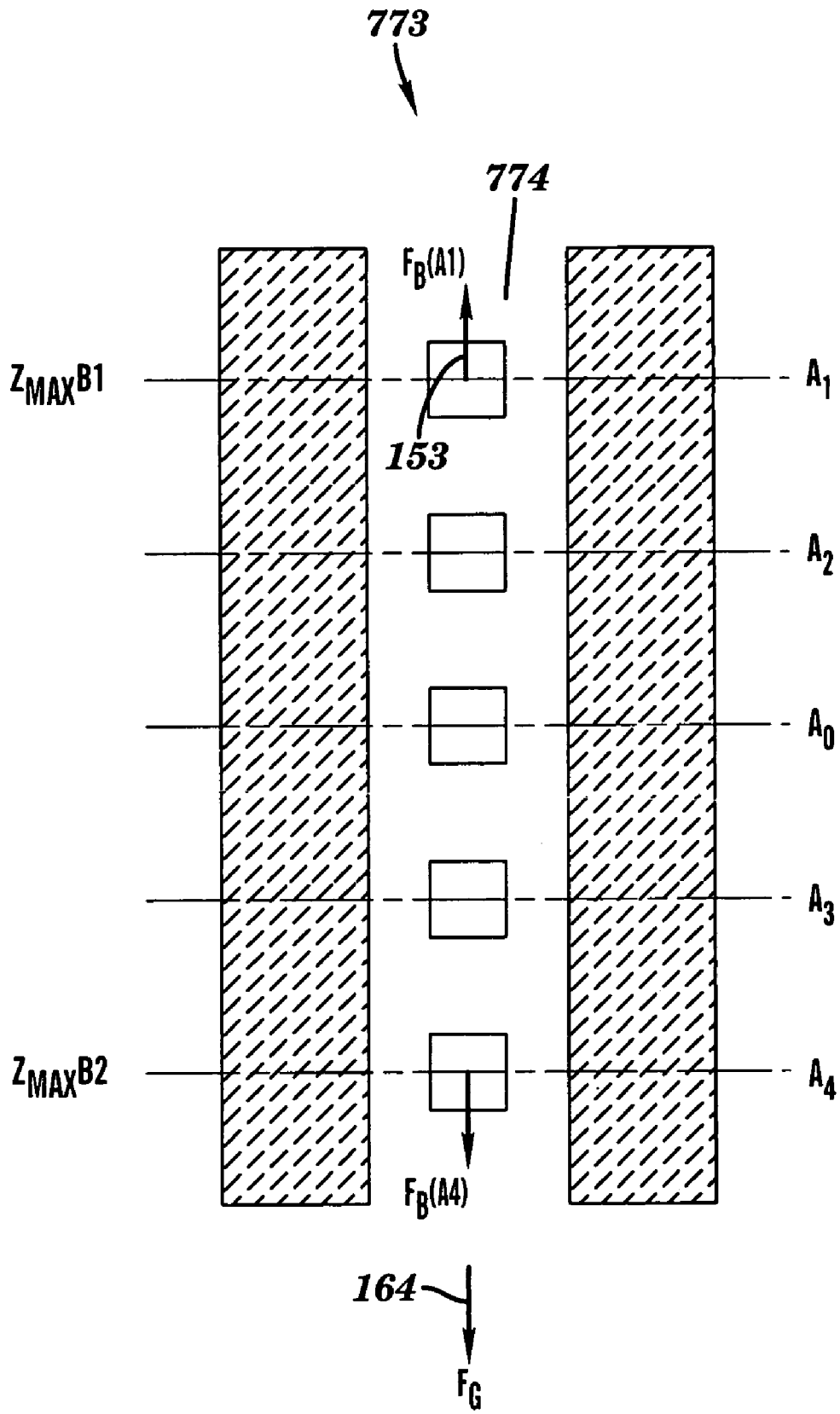

FIG. 30 is a schematic cross-sectional illustration of a vertically oriented solenoid superconducting magnet and several exemplary of locations for disposing one or more biospecimens in a diamagnetic force field.

Figure 31:
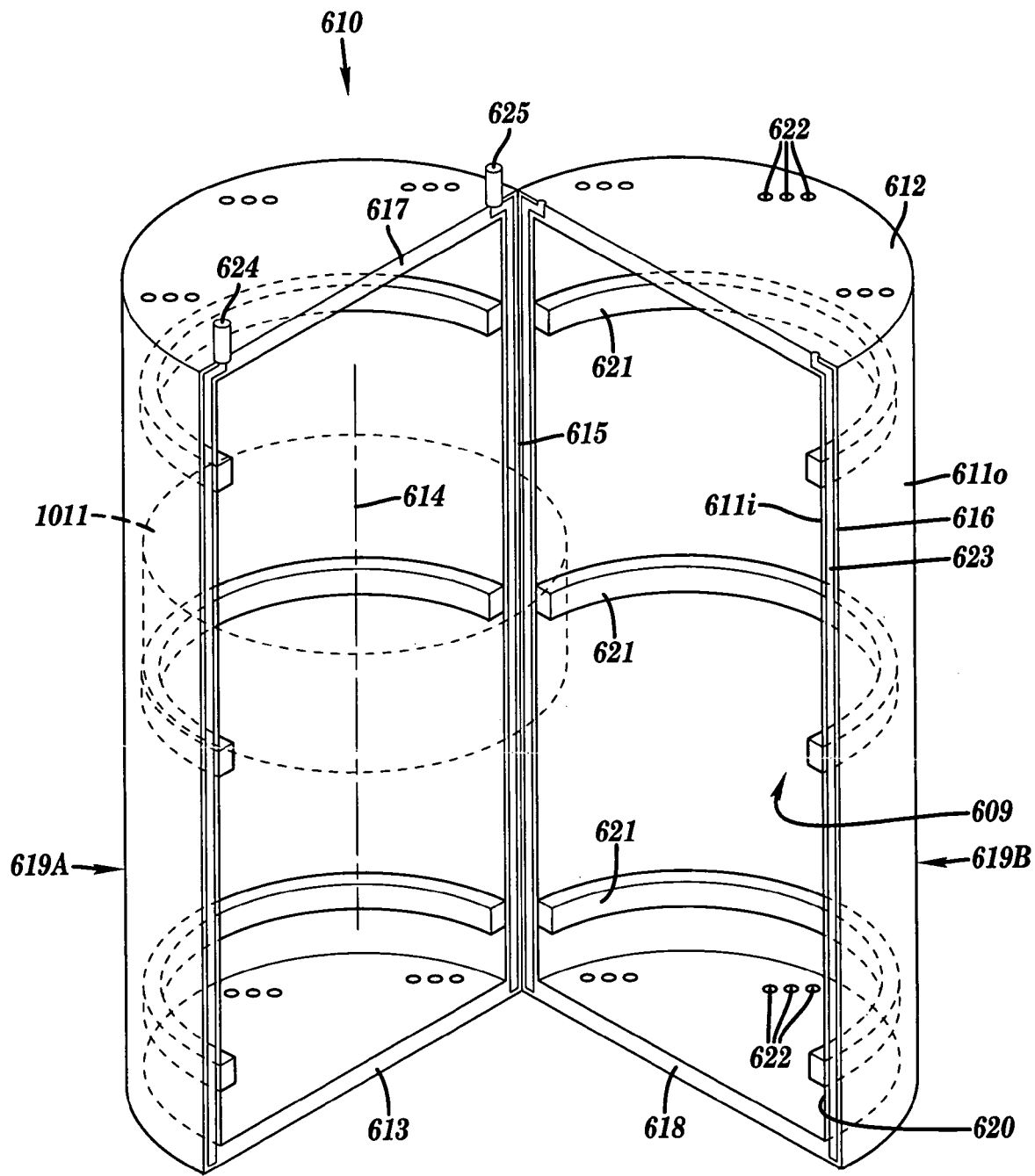

FIG. 31 is a perspective schematic illustration of an exemplary cylindrical housing of a second exemplary embodiment of the invention.

Figure 32:
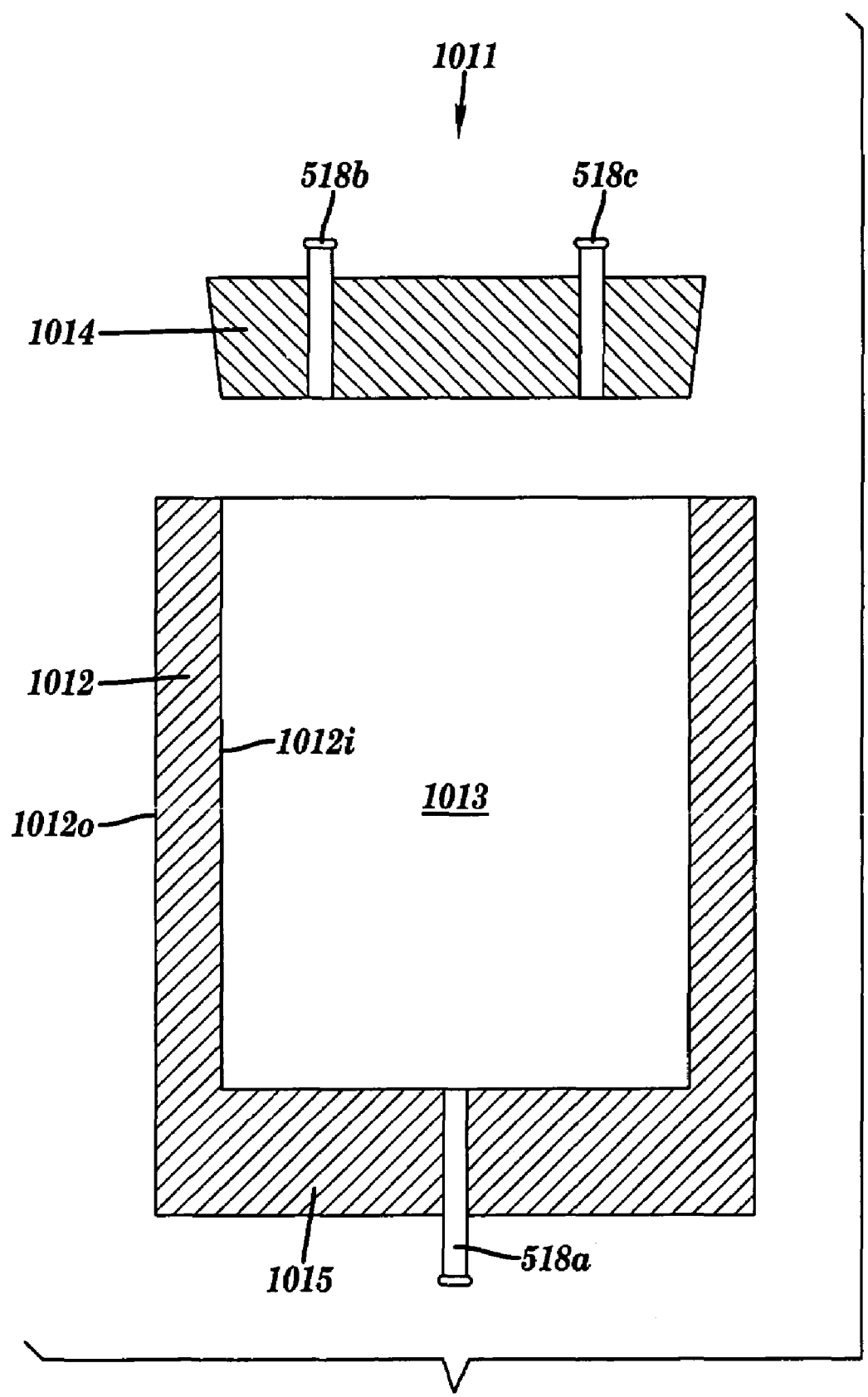

FIG. 32 shows a schematic cross-sectional view of an exemplary water-tight nonmagnetic cylindrical body common to a plurality of exemplary bioreactor chamber embodiments forming second set of bioreactor chamber embodiments.

Figure 33:
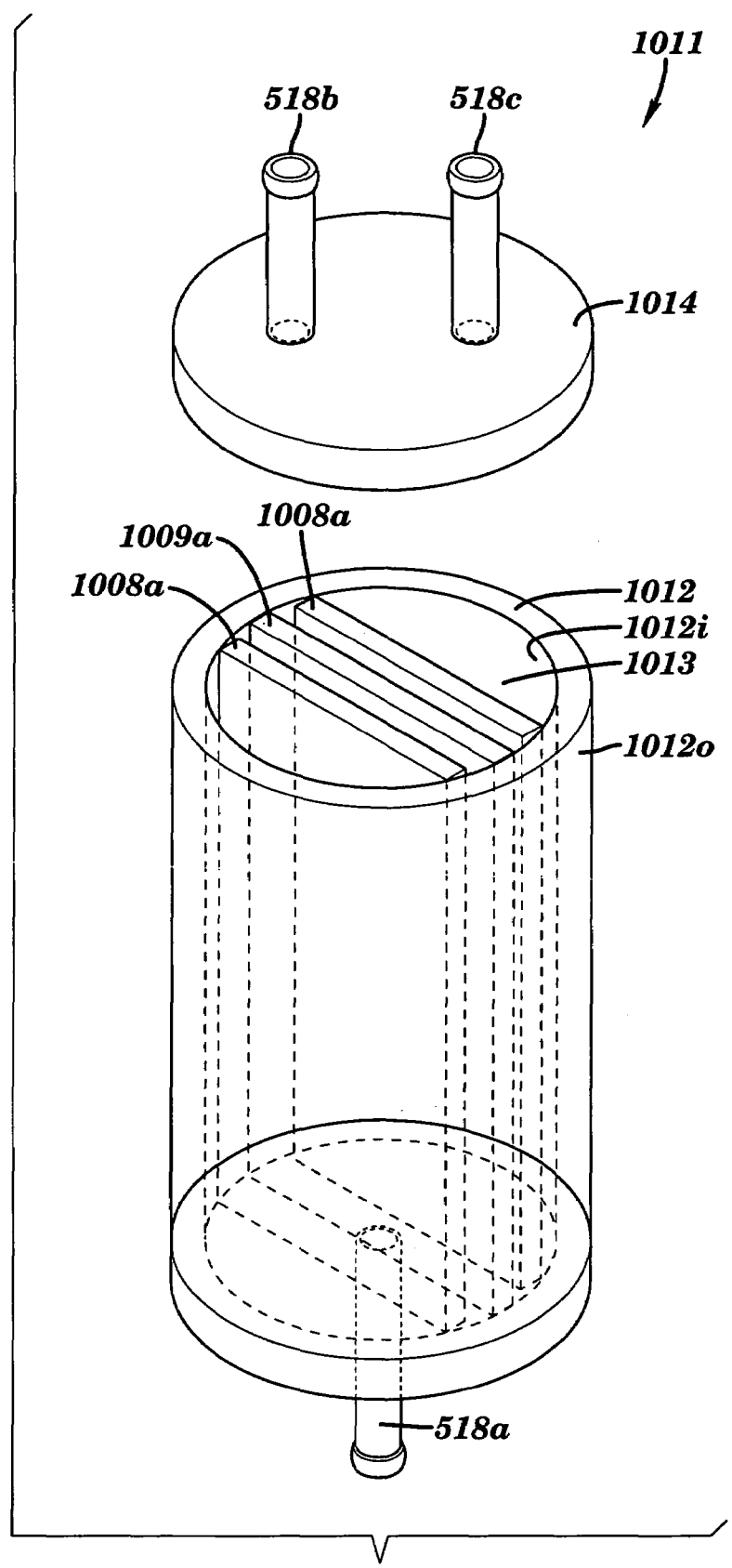

FIG. 33 is a schematic perspective view of an exemplary water-tight nonmagnetic common cylindrical body with an axial spacer and axial plates.

Figure 34:
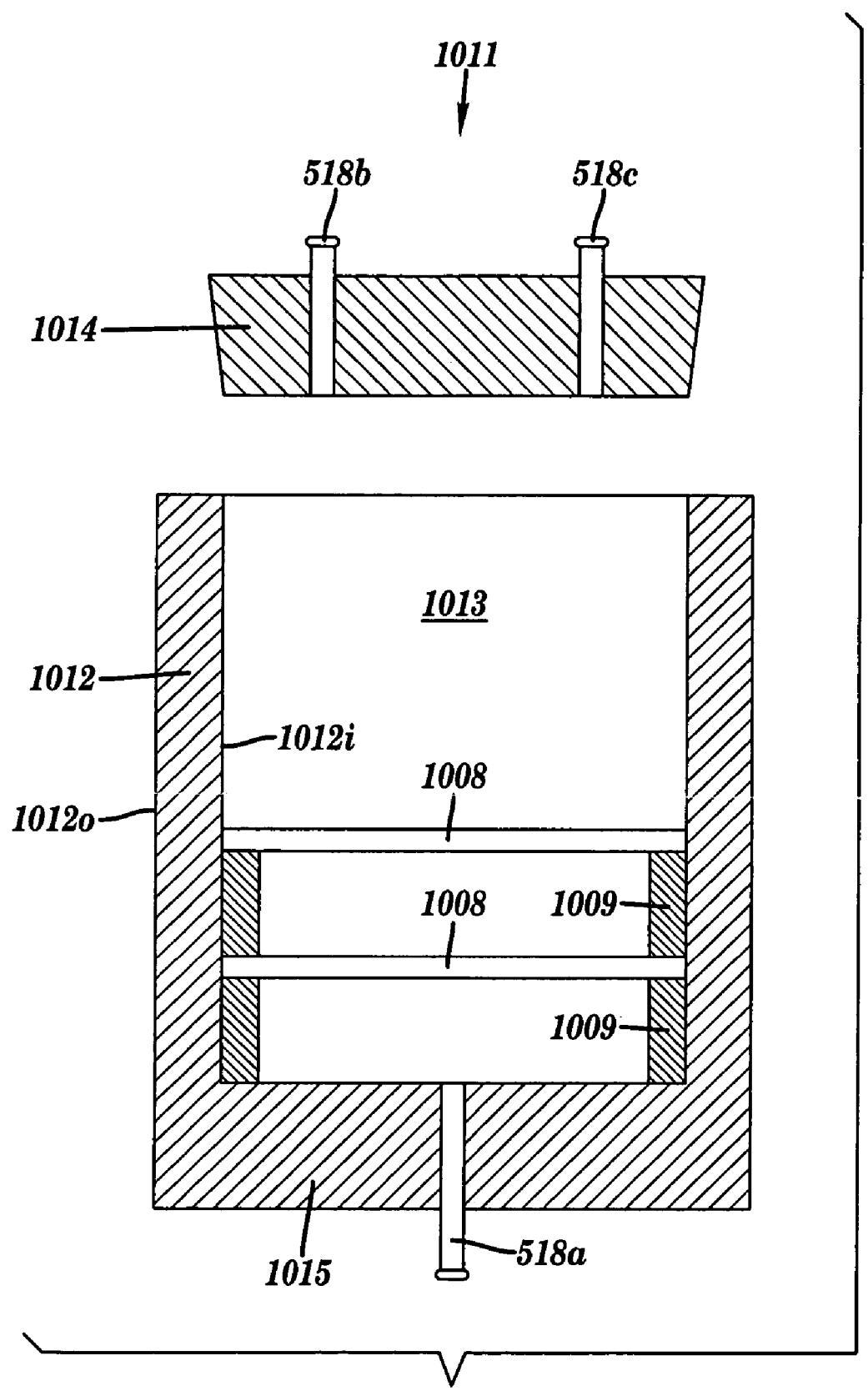

FIG. 34 is a schematic cross-sectional view of an exemplary water-tight nonmagnetic common cylindrical body with annular trans-axial spacers supporting trans-axial plates

4. SUMMARY OF THE INVENTION

The present invention is an apparatus comprising a magnet, at least one region of space, a bioreactor positioning system, and at least one bioreactor chamber disposed in the region of space by the bioreactor positioning system and operationally connected to a biological in vitro support system, wherein the region of space contains all points at which a magnetic field-field gradient product of the magnet equals or exceeds a threshold value.

5. DETAILED DESCRIPTION OF THE INVENTION

As used herein the term biospecimen (hereinafter "biospecimen") includes, but is not limited to: cells; three-dimensional cellular aggregates; two-dimensional cellular monolayers, including endothelial or epithelial cell monolayers having a luminal surface and a basal surface; two-dimensional cellular monolayers, including endothelial or epithelial cell monolayers, having a luminal surface and a basal surface, wherein the basal surface generally anchors the cellular monolayer to a substrate on which the cellular monolayer is grown, which anchorage has a spatially orienting effect on the endothelial or epithelial cells of the monolayer known as anchor-dependence; two-dimensional cellular monolayers, including endothelial or epithelial cell monolayers, maintained in contact with a fluid, such as, for example, the cellular monolayers and fluids paired in TABLE 1.

TABLE 1

Table of Exemplary Cellular Monolayers Maintained in Contact with Exemplary Fluids

| Fluid | Corresponding cell monolayer |
|---|---|
| blood, serum, plasma, saline, | cardiovascular epithelium |
| Physiologic fluid | any epithelium |
| Saliva | Stenson's duct or oropharyngeal epithelium |
| Bile | common hepatic duct epithelium |
| Insulin | pancreatic duct epithelium |
| cerebrospinal fluid | neuroendothelium or cerebral aqueduct epithelium |
| cerebrospinal fluid | leptomeningeal tissue (dura, arachnoid, pia) |
| gastric acid | stomach or esophageal epithelium |
| Urine | ureteral or urethral epithelium |
| Semen | epidydimal epithelium |
| Lymph | lymphatic epithelium |
| Air | respiratory epithelium |
| Oxygen | respiratory epithelium |
| Sebum | sebaceous epithelium |
| Tears | lacrimal epithelium |
| Mucous | mucosal epithelium, e.g., vaginal epithelium |
| Aqueous | trabecular meshwork epithelium |
| Vitreous | neuroretinal cells |

TABLE 1-continued

Table of Exemplary Cellular Monolayers Maintained in Contact with Exemplary Fluids

| Fluid | Corresponding cell monolayer |
|---|---|
| Sweat | apocrine or eccrine sweat gland epithelium |
| pleural fluid | pleural cells, pleural epithelium |
| pericardial fluid | pericardial cells, pericardium |
| Ascites | periotoneal cells, peritoneum |
| Suppurative fluid | abscess epithelial cells; inflammatory cells |

As used herein the term "bioreactor chamber" means an apparatus adapted to operationally connect with a biological in vitro support system, as described hereinafter, to provide an in vitro environment in a diamagnetic force field, as described hereinafter, that, inter alia, satisfies the metabolic requirements of any one or all of the physiological processes of a biospecimen, such as, for example, homeostasis, growth, replication, differentiation and self-organization.

5.1 Mammalian Cell Culture

The culture of mammalian cells in vitro presents formidable technological challenges not present in the culturing of bacterial cells. Bacterial cells have rigid outer cell walls in addition to a cell membrane, making them more resistant than mammalian cells to the stresses of laboratory manipulation and culture in vitro. Mammalian cells present only delicate cell membranes to their environment and cannot withstand such stresses. Moreover, bacterial cells are unicellular organisms that do not undergo differentiation and self-organization into specialized tissues such as organ tissues, structural tissues, and hematopoeitic tissues that are present in mammals.

Mere replication of mammalian cells in vitro may occur if they are exposed to a proper nutrient medium and often only if they are additionally supported by complex structural substrates. However, the in vitro differentiation and self-organization of replicating mammalian cells into tissues and organs has been limited by the inability to provide a spatial and mechanical environment in vitro similar to that present in vivo, upon which environment differentiation and self-organization depend.

The mechanisms of the in vitro differentiation and self-organization of mammalian cells into tissue and organs that are high-fidelity analogues of their in vivo counterparts are complex, and include interactions in which, inter alia, cells, cell membrane junctions, basement membrane, ground substances, and soluble molecular signals participate. These interactions are in turn dependent upon the spatial orientation of the foregoing entities with respect to each other. Accordingly, while the in vitro culture of isolated mammalian cells requires a technology for the support of mammalian cell metabolic processes, the in vitro growth of mammalian cells into tissues and organs further requires the creation of a mechanical and spatial environment conducive to cellular differentiation and self-organization.

5.2 Effect of Gravity on Mammalian Cell Culture

The gravitational field in which mammalian cells are replicating plays an important role in modulating growth through the more complex processes of differentiation and self-organization into tissues and organs that are high-fidelity analogues of their in vivo counterparts. For example, most conventional mammalian cell bioreactors, operating in the unit-gravitational field present on the Earth's surface, cannot provide an environment conducive to the differentiation and self-organization of mammalian cells into tissues that are high-fidelity analogues of their three-dimensional counterparts in the intact organism. Consequently the cells cannot evolve into functionally specialized phenotypes that synthesize bioactive molecules of interest to basic biological research and pharmaceutical development. The prevention of three-dimensional differentiation and self-organization in vitro is due in part to the adverse mechanical environment arising within most conventional bioreactors, and in part, to the presence of a unit gravitational field at the Earth's surface.

The adverse mechanical environment internal to most conventional bioreactors rises from the need to agitate the liquid nutrient medium in which mammalians cells are suspended in order to distribute nutrients to the cells and to disperse their metabolic wastes. Agitation of the nutrient medium subjects the cells to fluid-derived shear stresses to which they are poorly resistant, thereby limiting their replication. Agitation additionally interferes with cell-to-cell freedom of spatial orientation and association, as well as upon the cell-to-cell exchange of soluble chemical signals, intercellular mechanical signals, cellular to insoluble substrate interactions, and other interactions inductive of differentiation and self-organization.

The unit gravitational field at the Earth's surface exacerbates the problems introduced by mechanical agitation by forcing cells suspended in close proximity to one another to precipitate from suspension by sedimentation. One way of alleviating the adverse effect of sedimentation on the desired differentiation and self-organization of mammalian cells cultured in vitro is to loft the cells into orbit, an enterprise that is expensive, dangerous, and still ineffective in moderating the adverse effect of agitation-induced fluid shear stresses.

5.3 Limitations of NASA's RWV Bioreactor

NASA has developed an earthbound bioreactor for the culture of mammalian cells in an environment that simulates, but does not reproduce, a reduced gravitational state. Known as NASA's rotating wall vessel ("RWV") bioreactor, this device is designed to use fluid shear stresses that arise from spinning a culture medium, in which mammalian cells are suspended, to impede the gravitationally-induced sedimentation of the cells, thereby partially offsetting the influence of the force of terrestrial gravity.

However, the resultant state of microgravity is only a crude approximation of the microgravitational state that obtains in an extraterrestrial environment such as that found in the International Space Station or on the surface of the Moon. A pseudo-microgravitational state is created rather than a true microgravitational state, because the force of mechanical shear, a surface (or contact) force, whose action requires the physical contact of objects, (e.g., contact of cell and fluid) is used with the expectation that it will offset the force of terrestrial gravity, a body (or field) force, whose action, by contrast, does not depend on the physical contact of objects.

In a true microgravitational state, such as, for example, that which is present in the International Space Station, the Space Station's centrifugal force, a body force, counterbalances the body force of gravity exerted by the Earth. Alternatively stated, physically authentic states of weightlessness can only arise by counterbalancing the body force of gravity acting on an object with another opposing body force. This is because surface forces cannot counterbalance gravitationally-induced stresses arising internal to an object. On the other hand, body forces are distinguished from surface forces by their ability to induce internal stresses.

The foregoing physical distinction is significant at the molecular biological level, where the determinants of mammalian cell differentiation and self-organization operate. For example, the number and kinds of genes expressed during mammalian cell replication in a true (body force v. gravitational force) microgravity environment is different from the number and kinds of genes expressed during cell replication in a pseudo-microgravity environment (surface force v. gravitational force), such as that created within NASA's RWV bioreactor. Moreover, mammalian cells grown in vitro in true microgravity much more closely resemble those found growing within living organisms at the surface of the earth.

5.4 Advantages of Present Invention

The present invention is an apparatus comprising a magnet adapted to create a diamagnetic force field at all points in space at which a magnetic field-field gradient product of the magnet has a value greater than or equal to a threshold value. At or above the threshold value, the diamagnetic force field induces a diamagnetic body force within a biospecimen supported within a bioreactor chamber that is disposed within the diamagnetic force field. The apparatus may alter the magnitude of the induced diamagnetic body force and may alter the direction of the induced diamagnetic body force with respect to a spatial coordinate system, such as, for example, a Cartesian, polar, cylindrical or spherical coordinate system. The apparatus may further alter the direction of the induced diamagnetic body force with respect to the direction of a secondary body force acting upon or within the biospecimen, thereby altering the vector sum of the induced diamagnetic body force and the secondary body force acting on the biospecimen.

5.5 Secondary Body Forces

The secondary body force acting on the biospecimen may, for example, be a gravitational force, such as, for example, the gravitational force exerted by the Earth at its surface, or the gravitational force operative at the International Space Station, or on the surface of the Moon. The secondary body force acting on the biospecimen may, for example, also be a centrifugal or centripetal force; or it may additionally be, for example, another diamagnetic body force induced by another diamagnetic force field. The secondary body force acting on the biospecimen may, for example, further be an electric force or a magnetic force.

In the case where the secondary body force is a gravitational force, the present invention generates a diamagnetic force field about a biospecimen within which there is induced a diamagnetic body force, whose magnitude and direction may be controlled to, inter alia, variably counterbalance the force of gravity acting upon the biospecimen, thereby altering the net gravitational force acting on the biospecimen.

In the case where the secondary body force is a gravitational force, such as, for example, the force of gravity at the Earth's surface, the present invention generates a diamagnetic force field about a biospecimen within which there is induced a diamagnetic body force, whose magnitude and direction may be controlled to, inter alia, variably counterbalance the force of the Earth's gravity acting upon the biospecimen, thereby altering its weight.

5.6 The Magnetic Field Induction

The magnetic field, magnetic induction, or magnetic flux density that is generated in the space about a magnet is inferred from the action of a magnetic force on a charged particle moving with velocity v in the locality of the magnet. The charged particle is acted upon by a force F given by the equation $$F = q_0 v \times B \quad (1)$$

where $q_0$ is the charge of the particle moving with respect to the magnetic field vector B. Equation (1) inferentially defines the magnetic field vector B, measured in units of Tesla (T). B is the primary physical characterization of a magnetic field.

The orbital motion of the electrons in all materials, including biospecimens, may be regarded as microscopic current loops that function as microscopic magnetic dipoles. If a material is placed in an externally applied magnetic field, the material's microscopic magnetic dipoles will establish an induced magnetic field of their own, that will modify the externally applied magnetic field. The external magnetic field and the magnetic field induced internal to the material are related by a constant of proportionality that varies from material to material, and is referred to as the magnetic permeability $\mu$ of the material.

The magnetic permeability of most materials differs very little from the magnetic permeability of free space, a constant assigned the symbol $\mu_0$. The magnetic permeability $\mu$ of a material is related to the magnetic permeability of free space $\mu_0$ by the relative permeability $K_m$ of the material through the equation $$\mu = K_m \mu_0 \quad (2)$$

If a material does not respond to an external magnetic field, producing no induced magnetism, then its relative permeability $K_m = 0$.

The magnitude and the sign of the magnetic permeability $\mu$ of a material are indicative of the magnitude and orientation of the magnetic field induced in the material by an externally applied magnetic field, and may be used to classify materials by their response to externally applied magnetic fields as being diamagnetic, paramagnetic, or ferromagnetic.

When an external magnetic field is applied to a material, its microscopic current loops tend to align in such a way as to generate a weak internal magnetic field that opposes the externally applied magnetic field. Materials in which this effect is the sole magnetic response are called diamagnetic materials, and all materials are inherently diamagnetic.

5.7 Paramagnetism, Ferromagnetism and Diamagnetism

Paramagnetism, when present in a material, produces an internal magnetization having the same direction as the externally applied magnetic field, and is proportional to the externally applied magnetic field. Ferromagnetism, when present in a material, also produces an internal magnetization having the same direction as the externally applied magnetic field. However, the induced internal magnetization may be orders of magnitude greater than the externally applied magnetic field, and may persist after the removal of the externally applied magnetic field.

The magnitude of the diamagnetic response is far weaker than the magnitude of either the paramagnetic or the ferromagnetic response. The diamagnetic response is overwhelmed in materials having a paramagnetic or ferromagnetic response. Accordingly, diamagnetism is the residual magnetic behavior of materials that are neither paramagnetic nor ferromagnetic.

Another commonly used index of induced magnetization is the magnetic susceptibility $\chi_m$, which specifies how much the relative magnetic permeability of a material differs from unity, and is given by the equation $$\chi_m = K_m - 1. \quad (3)$$

For diamagnetic materials, the relative permeability $K_m$ is very close to 1 and the magnetic susceptibility $\chi_m$ is very close to zero. The magnetic susceptibilities of water and mammalian cells and tissues are nearly identical, being on the order of $10^{-5}$

5.8 The Diamagnetic Body Force

Owing to its diamagnetic response, when placed in a region of space in which a magnetic field B has a gradient $\nabla B$, a diamagnetic material is subjected to an induced diamagnetic body force $F_B$ that is proportional to the vector dot product of the magnetic field and its gradient, i.e., $$F_B \propto B \circ \nabla B \quad (4)$$

The direction of $F_B$ is given by direction of $\nabla B$.

5.9 The Magnetic Field-Field Gradient Product

The scalar quantity $B \circ \nabla B$ is called the magnetic field-field gradient product, and, with respect to any device that generates a magnetic field B that has a gradient $\nabla B$, it is the key determinant of the diamagnetic body force $F_B$ that is induced in a diamagnetic material.

By way of example, in the specific case of a magnetic field having a gradient that is a function of only one spatial variable z, the magnitude of the diamagnetic body force induced in a diamagnetic material is given by $$|F_B| = (\chi/\mu_0) \, V B(z) \partial B/\partial z \quad (5)$$

where:
$\chi$ is the magnetic susceptibility of the material, dimensionless in the MKS system;
$\mu_0$ is magnetic permeability of free space, given by $4\pi \times 10^{-7}$ T meter/Ampere;
V is the volume of the diamagnetic material in cubic meters;
B(z) is the magnetic field in Tesla;
$\partial B/\partial z$ is the gradient of the magnetic field in the z direction; and
$B(z)\partial B/\partial z$ is the magnetic field-field gradient product.

In physics, the space in the vicinity of an object capable of exerting a body force is said to be altered by the presence of such an object, and the alteration of the space in the vicinity of the object is referred to as a the field created by that object. For example, a mass particle generates a gravitational field in its vicinity and a charged particle generates an electric field in its vicinity. The gravitational field is quantitatively defined as the gravitational force per unit mass and the electric field is quantitatively defined as the electric force per unit charge.

5.10 Diamagnetic Force Field

In light of equation (5), and by analogy with the definition of a field in physics and the foregoing examples thereof, as used herein, a diamagnetic force field $D_B$ is qualitatively defined herein as an alteration present at all points in space in the vicinity of a magnet, at which a magnetic field-field gradient product of the magnet, has a predetermined nonzero threshold value. Quantitatively, the magnitude of the diamagnetic force field $D_B$ is defined herein as the measured diamagnetic body force $F_B$ induced per measured unit mass of diamagnetic material, when it is placed within the space of the diamagnetic force field $D_B$.

Defined this way, a diamagnetic force field $D_B$ of a magnet can induce a diamagnetic body force $F_B$ within a biospecimen disposed within it, that, inter alia, can act to oppose and counteract a secondary body force, such as, for example, a gravitational force, acting upon the biospecimen, for example, on the Earth's surface; or, the diamagnetic body force $F_B$ induced by the diamagnetic force field $D_B$ can act as an artificial force of gravity upon the biospecimen in an environment where the Earth's force of gravity has already been counterbalanced by a centrifugal force, such as, for example, aboard the International Space Station.

At the surface of the Earth, the magnitude of the gravitational force G acting on a biospecimen having a mass m in kilograms that is being sustained in vitro is given by $$|G| = m \, |g| \quad (6)$$

where the vector g is the acceleration of gravity, having a magnitude of about 9.81 m/sec$^2$. Equation (6) may be equivalently written in terms of the mass density of a biospecimen as $$|G| = \rho V g \quad (7)$$

where:
$\rho$ is the mass density of a biospecimen sustained in vitro, measured in kilograms per cubic meter;
V is the volume of the biospecimen sustained in vitro in cubic meters; and, $g = |g|$.

If the diamagnetic body force $F_B$ is to completely counterbalance the force of gravity exerted on a biospecimen sustained in vitro at or near the surface of the Earth, then $$|F_B| = |G|. \quad (8)$$

Substituting, through the use of equation (7) for G and through the use equation (5) for $F_B$, yields $$(\chi/\mu_0) \, V B(z) \partial B/\partial z = \rho V g \quad (9)$$

or equivalently, $$(\chi/\mu_0) B(z) \partial B/\partial z = \rho g \quad (10)$$

For a biospecimen sustained in vitro having a density and a magnetic susceptibility approximately equal to that of water, i.e., $\chi = -9.03 \times 10^{-6}$, $\rho = 993$ kg/m$^3$ at 37° C., and with $g = 9.81$ m/sec$^2$, equation (10) may be solved for the magnitude of the magnetic field-field gradient product required to completely counterbalance the force of gravity acting upon a biospecimen sustained in vitro, yielding the value, $$B(z) \partial B/\partial z \approx 1356 \, T^2/m \quad (11)$$

This turns out to be a very large magnitude for the magnetic field-field gradient product. Because of geometrical constraints on the spatial extent and magnitude of the magnetic field gradient ($\partial B/\partial z$) that a magnet may generate, the magnitude of magnetic field inductance B that a magnet may generate must in general be very large to counterbalance the force of the Earth's gravity.

Summarizing, a magnet productive of a magnetic field B that has a magnetic field gradient $\nabla B$, whose magnetic field-field gradient product $B \circ \nabla B$ is at least about 1356 T$^2$/m can create a diamagnetic force field $D_B$, coincident with the space of all points about the magnet at which the magnetic field-field gradient product $B \circ \nabla B$ is at least about 1356 T$^2$/m, which diamagnetic force field $D_B$ is inductive of a diamagnetic body force $F_B$ within a biospecimen sustained in vitro in the space. The induced diamagnetic body force $F_B$ may have a direction opposite to the direction of a secondary body force, such as, for example, the force of gravity $F_G$ near the Earth's surface, and may have a magnitude that partially or completely counterbalances the force of gravity $F_G$.

5.11 Maximum Value

As used herein, the term "maximum value of a magnetic field-field gradient product" (hereinafter "maximum value") refers to the maximum measured value of a magnetic field-field gradient product of a magnet and includes in its meaning the following kinds of maximum values.

5.12 Maximum Radial Value

As used herein, the term "maximum radial value of a magnetic field-field gradient product" (hereinafter "maximum radial value") refers to the value of a magnetic field-field gradient product of a transverse electromagnet magnet measured at a radius about equal to a pole radius of the modified transverse electromagnet.

5.13 First and Second Maximum Axial Values

As used herein, the term "first maximum axial value of a magnetic field-field gradient product" (hereinafter "first maximum axial value") refers to a maximum value of a magnetic field-field gradient product measured at a first point along an axis of a bore of a superconducting solenoid magnet; and, the term "second maximum axial value of a magnetic field-field gradient product" (hereinafter "second maximum axial value") refers to a maximum value of a magnetic field-field gradient product measured at a second point along-the axis of the bore of the superconducting solenoid magnet.

5.14 Threshold Value

As used herein, the term "threshold value of a magnetic field-field gradient product" (hereinafter "value") refers to a predetermined percentage of a maximum value and includes in its meaning the following kinds of threshold values.

5.15 First Threshold Radial Value

As used herein the term "first threshold radial value of a magnetic field-field gradient product" (hereinafter "first threshold radial value") refers to a value of a magnetic field-field gradient product corresponding to 5% of the maximum radial value, which first threshold radial value is measured at a radius greater than a pole radius of a modified transverse electromagnet.

5.16 Second Threshold Radial Value

As used herein the term "second threshold radial value of a magnetic field-field gradient product" (hereinafter "second threshold radial value") refers to a value of a magnetic field-field gradient product corresponding to 5% of the maximum radial value which second threshold radial value is measured at a radius less than a pole radius of a modified transverse electromagnet.

5.17 First Outer Threshold Axial Value

As used herein the term "first outer threshold axial value of a magnetic field-field gradient product" (hereinafter "first outer threshold axial value") refers to a value corresponding to 20% of the first maximum axial value.

5.18 Second Outer Threshold Axial Value

As used herein the term "second outer threshold axial value of a magnetic field-field gradient product" (hereinafter "second outer threshold axial value") refers to a value corresponding to 20% of the second maximum axial value.

5.19 First Inner Threshold Axial Value

As used herein the term "first inner threshold axial value of a magnetic field-field gradient product" (hereinafter "first inner threshold axial value") refers to a value corresponding to 80% of the first maximum axial value.

5.20 Second Inner Threshold Axial Value

As used herein the term "second inner threshold axial value of a magnetic field-field gradient product" (hereinafter "second inner threshold axial value") refers to a value corresponding to 80% of the second maximum axial value.

5.21 Spatial Envelope of a Diamagnetic Force Field

The points in space at which the magnitude of a magnetic field-field gradient product of a transverse electromagnet equal the first and second threshold radial values define the spatial envelope of the space within which a diamagnetic force field $D_B$ is effectively present. The points in space at which the magnitude of a magnetic field-field gradient product of a superconducting solenoid magnet equal the first and second outer threshold axial values define the spatial envelope of the space within which a diamagnetic force field $D_B$ is effectively present.

5.22 Space of a Diamagnetic Force Field

In the case of a transverse electromagnet, the term "space of a diamagnetic force field" $D_B(r)$ refers to a region of space generally comprising the set of all points at which the magnetic field-field gradient product of the transverse electromagnet $B(r)\partial B/\partial r$ equals or exceeds the lesser of either the first or the second threshold radial value, and includes all points at which the magnitude of the magnetic field-field gradient product $B(r)\partial B/\partial r$ of the transverse electromagnet equals the maximum radial value.

In the case of a superconducting solenoid magnet, the term "space of a diamagnetic force field" $D_B(z)$ refers to the set of all points generally comprising a cylindrical region of space within the bore of the superconducting solenoid magnet at which the magnetic field-field gradient product $B(z)\partial B/\partial z$ of the superconducting solenoid magnet equals or exceeds the lesser of the first or the second outer threshold axial values, and includes the points at which the magnitude of the magnetic field-field gradient product $B(z)\partial B/\partial z$ of the superconducting solenoid magnet equals both the first and second maximum axial values.

5.23 First Exemplary Embodiment

Referring now to the drawings in which like parts are designated by like numerals in the various views, FIG. 1 shows a perspective schematic view of a first exemplary embodiment of the invention 101, comprising a transverse electromagnet 400, adjacently disposed to a first exemplary embodiment of a bioreactor chamber positioning system (hereinafter, "first bioreactor positioning system") 300, supporting at least one of a plurality of exemplary bioreactor chamber embodiments, forming a first set of bioreactor chamber embodiments 500, each of which houses at least one exemplary biospecimen 153, and each of which sustains at least one exemplary biospecimen 153 in vitro by operational connections to a biological in vitro support system 200, all being under the control of a computer 201.

Unless otherwise indicated, reference numeral 500 is generally intended to refer either to an individual exemplary bioreactor chamber embodiment of the first set of bioreactor chamber embodiments or to the first set of bioreactor chamber embodiments, with the appropriate reference being made apparent by the pertinent portion of the detailed description of the invention. Unless otherwise indicated, reference numeral 1000 is generally intended to refer either to an individual exemplary bioreactor chamber embodiment of a second set of bioreactor chamber embodiments or to the second set of bioreactor chamber embodiments, with the appropriate reference also being made apparent by the pertinent portion of the detailed description of the invention.

5.24 Transverse Electromagnet

Transverse electromagnet 400 is adapted to generate a diamagnetic force field (not shown in FIG. 1), as described supra., in a region of space within which first bioreactor chamber positioning system 300 disposes at least one exemplary biospecimen 153 in at least one of the plurality of exemplary bioreactor chamber embodiments, forming first set of bioreactor chamber embodiments 500, so that a diamagnetic body force (not shown in FIG. 1) as described supra., is induced in each exemplary biospecimen 153.

5.25 Precision Gauss Meter

A precision gauss meter 210, detachably connected to computer 201, has a probe 211 for measuring a magnetic field (not shown in FIG. 1), established between a first magnetic pole piece 426 and a second magnetic pole piece 427 of transverse electromagnet 400. The term "magnetic field" is used herein synonymously with the term "magnetic induction" or the term "magnetic flux density." Gauss meter probe 211 may conveniently be detachably connected to a nonmagnetic positioning arm 305 of first bioreactor positioning system 300 for measuring the magnitude of the magnetic field.

5.26 Biological In vitro Support System

Biological in vitro support system 200, under the operational control of computer 201, is comprised of a support system interface 220, a gas flow control subsystem 230, a temperature control subsystem 240, and a perfusion control subsystem 250.

5.27 First Tubing Set

In the first exemplary embodiment of the invention 101 (FIG. 1), in vitro support system interface 220 is configurable to independently route a first set of tubes 330 (alternatively referred to as "first tubing set 330" or "first tubing sets 330" in the plural form) from biological in vitro support system 200 to each of the plurality of exemplary bioreactor chamber embodiments forming first set of bioreactor chamber embodiments 500, and to return the first set of tubes 330 from each of these bioreactor chamber embodiments to biological in vitro support system 200, thereby completing a closed tubing circuit between biological in vitro support system 200 and each of the plurality of exemplary bioreactor chamber embodiments 500.

As shown in FIG. 1 each first set of tubes 330 is comprised of a first afferent tube bundle 333 and a first efferent tube bundle 334. Each first afferent tube bundle 333 is a triplet of tubes comprised of a first afferent gas tube 333$g$, a first afferent temperature tube 333$t$, and a first afferent perfusion tube 333$p$, respectively elaborated from gas flow control subsystem 230, temperature control subsystem 240, and perfusion control subsystem 250 of biological in vitro support system 200. Each first efferent tube bundle 334 is a doublet of tubes comprised of a first efferent temperature tube 334$t$, and a first efferent perfusion tube 334$p$, respectively returning to temperature control subsystem 240, and perfusion control subsystem 250 of biological in vitro support system 200. There is no tubing for the return of gas provided to first set of bioreactor chamber embodiments 500 or to second set of bioreactor chamber embodiments 1000 because gas from these bioreactor chamber embodiments is vented to the environment directly from an efferent gas port built into each bioreactor chamber embodiment, as more fully described, infra.

5.28 Water-tight Jackets of First Set of Bioreactor Chamber Embodiments

As shown in FIGS. 20A-20G, each exemplary bioreactor chamber embodiment of first set of bioreactor chamber embodiments 500 is enveloped in a water-tight jacket 509 having an afferent temperature port 516$t$ for detachably connecting first afferent temperature tube 333$t$ and an efferent temperature port 517$t$ for detachably connecting first efferent temperature tube 334$t$.

5.29 General Purpose Ports of First Set of Bioreactor Chamber Embodiments

As shown in FIGS. 20A-20G, each exemplary bioreactor chamber embodiment of first set of bioreactor chamber embodiments 500 also has three general purpose ports 518$a$, 518$b$, and 518$c$ for venting gas and/or detachably and exchangeably connecting, in appropriate combinations that depend on the desired in vitro environment, first afferent gas tube 333$g$, first afferent perfusion tube, 333$p$, and first efferent perfusion tube 334$p$.

5.30 Temperature-controlled Gas and Fluid Transport Subsystem for First Exemplary Embodiment of the Invention Accordingly, each exemplary bioreactor chamber embodiment of first set of bioreactor chamber embodiments 500 (FIGS. 20A-20G) communicating with first afferent tube bundle 333 and first efferent tube bundle 334 is supported by a temperature-controlled gas and fluid transport system.

5.31 Second Tubing Set

In a second exemplary embodiment of the invention 102, shown in FIG. 21, in vitro support system interface 220 is configurable to route a second set of tubes 390, shown in FIG. 21 (analogously including a second afferent tube bundle 393 with a second afferent gas tube 393$g$, second afferent temperature tube 393$t$ and second afferent perfusion tube 393$p$; and, a second efferent tube bundle 394 with a second efferent temperature tube 394t and second efferent perfusion tube 394p) from biological in vitro support system 200 to [i] an exemplary cylindrical housing 610 for the containment of a plurality of exemplary bioreactor chamber embodiments forming second set of bioreactor chamber embodiments 1000 (FIG. 31) and to [ii] each such second bioreactor chamber embodiment (FIGS. 32-34), and to return the second set of tubes 390 from the exemplary cylindrical housing 610 (FIG. 31) and each second bioreactor chamber embodiment 1000 (FIGS. 32-34) to biological in vitro support system 200 (FIG. 21) thereby completing a closed tubing circuit between [i] biological in vitro support system 200 (FIG. 21) and exemplary cylindrical housing 610 (FIG. 31) and thereby completing another closed tubing circuit between [ii] biological in vitro support system 200 (FIG. 21) and each bioreactor chamber embodiment 1000 (FIGS. 32-34), as more fully described, infra.

5.32 Cylindrical Water-tight Jacket of Cylindrical Housing for Containment of Second Set of Bioreactor Chamber Embodiments in Second Exemplary Embodiment of the Invention In the second exemplary embodiment of the invention 102 (FIG. 21), the exemplary cylindrical housing 610 (FIG. 31) is enveloped in a cylindrical water-tight jacket 623 (FIG. 31) having an afferent cylindrical temperature port 624 (FIG. 31) for detachably connecting second afferent temperature tube 393t and an efferent cylindrical temperature port 625 (FIG. 31) for detachably connecting second efferent temperature tube 394t.

5.33 General Purpose Ports of Second Set of Bioreactor Chamber Embodiments

In the second exemplary embodiment of the invention 102, each exemplary bioreactor chamber of second set of bioreactor chamber embodiments 1000 also has three general purpose ports 518a, 518b, and 518c (FIGS. 32-34), for venting gas and/or detachably and exchangeably connecting, in appropriate combinations that depend on the desired in vitro environment, second afferent gas tube 393g, second afferent perfusion tube 393p, and second efferent perfusion tube 394p.

5.34 Temperature-controlled Gas and Fluid Transport Subsystem for First Exemplary Embodiment of the Invention Accordingly, in second exemplary embodiment of the invention 102, exemplary cylindrical housing 610 (FIG. 31) and each bioreactor chamber of second set of bioreactor chamber embodiments 1000 (FIGS. 32-34) communicating with second afferent tube bundle 393 (FIG. 21) and second efferent tube bundle 394 (FIG. 21) is also supported by a temperature-controlled gas and fluid transport system.

5.35 Perfusion Control Subsystem of In vitro Support System

Perfusion control subsystem 250, shown in FIG. 1, under the control of computer 201, provides nutrients to and removes biological wastes from exemplary biospecimen 153 in any exemplary bioreactor chamber embodiment of first set of bioreactor chamber embodiments 500 and in any exemplary bioreactor chamber embodiment of second set of bioreactor chamber embodiments 1000. Perfusion control subsystem 250 may also adjustably perfuse exemplary biospecimen 153, thereby subjecting exemplary biospecimen 153 to various states of fluid flow, including a zero-flow state. Non-zero flow states created by perfusion control subsystem 250 may, for example, simulate the physiological or pathophysiological flow of blood, or any of the exemplary fluids listed in Table 1, supra., with respect to a vascular cell monolayer, or any of the exemplary cellular monolayers listed in Table 1, supra.

As shown in FIG. 1, perfusion control subsystem 250 is comprised of a temperature controlled water bath 252 containing a gas humidifier reservoir 253, a medium reservoir 254, and a flow damper reservoir 255, serially connected to each other by perfusate tubing 258.

Dry, sterilized and pressurized gas, such as, for example, a mixture of 95% air and 5% $CO_2$, from a perfusate gas source 259 is filtered and delivered to gas humidifier reservoir 253, where it is warmed and humidified, and thereafter delivered into the space above the surface of a fluid perfusate contained medium reservoir 254.

Medium reservoir 254 contains the fluid perfusate at a controllable pH and composition for providing nutrients to exemplary biospecimen 153 and for exposing exemplary biospecimen 153 to any desired biochemicals, such as, for example, cytokines or pharmacologic agents. The perfusate in medium reservoir 254 may also be used for performing static or dynamic perfusion studies involving exemplary biospecimen 153, such as, for example, simulating the physiological or pathophysiological flow of blood with respect to a vascular cell monolayer, or simulating the physiological or pathophysiological flow of any of the exemplary fluids listed in Table 1, supra, with respect to any of the exemplary cellular monolayers listed in Table 1, supra.

5.36 Perfusion Studies

In connection with such perfusion studies, FIG. 20E, shows a cross-sectional schematic illustration of an exemplary bioreactor chamber in vitro support of a 2-dimensional exemplary biospecimen 153 in a diamagnetic force field with perfusion, represented by a perfusate flow vector $P_F$ [190], directed perpendicularly to a diamagnetic body force $F_B(r)$ [154] induced in biospecimen 153, to be more fully discussed infra; and, FIG. 20F, shows a cross-sectional schematic illustration of an exemplary bioreactor chamber for in vitro support of a 2-dimensional exemplary biospecimen 153 in a diamagnetic force field with perfusion, represented by a perfusate flow vector $P_F$ [190], directed parallel to a diamagnetic body force $F_B(r)$ [154] induced in biospecimen 153, also to be more fully discussed, infra.

Medium reservoir 254 is part of a closed loop flow circuit and has five ports (not shown in FIG. 1): a gas inflow port receives gas from perfusate gas source 259; a filter vent (not shown in FIG. 1) maintains medium reservoir 254 at atmospheric pressure without compromising sterility; an outflow port delivers perfusate to flow damper reservoir 255; a return inflow port receives efferent perfusate from perfusate manifold collecting unit 257; and, a sampling port allows perfusate sample collection without disruption of flow.

Flow damper reservoir 255 is a pressurized chamber having an inflow port (not shown in FIG. 1) for receipt of perfusate from medium reservoir 254 and an outflow port (not shown in FIG. 1) for the output of a perfusate free of pulsations that may be generated by variable speed peristaltic pump 251.

Variable speed peristaltic pump 251 draws perfusate out of medium reservoir 254 into flow damper reservoir 255 and thence, following pressure build-up in flow damper reservoir 255, into a fluid flowmeter regulator multiplier unit 256 for afferent distribution to each exemplary biospecimen 153 within each exemplary bioreactor chamber embodiment of first set of bioreactor chamber embodiments 500 or each exemplary bioreactor chamber embodiment of second set of bioreactor chamber embodiments 1000, via first afferent perfusion tube 333$p$ routed through in vitro support system interface 220.

After perfusing exemplary biospecimen 153, perfusate returns to perfusion control subsystem 250 via first efferent perfusion tube 334$p$, conducted through in vitro support system interface 220, and a manifold collecting unit 257, thereby completing a closed tubing circuit between perfusion control subsystem 250 and each of the plurality of exemplary bioreactor chamber embodiments forming first set of bioreactor chamber embodiments 500 or each of the plurality of exemplary bioreactor chamber embodiments forming second set of bioreactor chamber embodiments 1000.

The volume of perfusate in the closed perfusion circuit, about 200 to 400 ml, is large compared with the volume of metabolic waste generated by one or more exemplary biospecimens sustained in vitro in the space of the diamagnetic force field generated-by the invention. Accordingly, in cases of exposure of biospecimens 153 to the diamagnetic force field for a few hours to a day, the volume of circulating perfusate will dilute metabolic waste to a negligible level. In cases of exposure of biospecimens 153 to the diamagnetic force field for several days, circulating perfusate should be removed and replaced with fresh perfusate about every two to three days.

5.37 Gas Flow Control Subsystem of In vitro Support System

In FIG. 1, gas flow control subsystem 230, comprising gas source 231 and gas flowmeter regulator multiplier unit 232, provides gases, such as, for example, a mixture of 95% air and 5% $CO_2$, to regulate the atmosphere to which exemplary biospecimen 153 is exposed within any exemplary bioreactor chamber embodiment of first set of bioreactor chamber embodiments 500 or any exemplary bioreactor chamber embodiment of second set of bioreactor chamber embodiments 1000. Gas from gas source 231 is distributed, via in vitro support system interface 220 and first afferent gas tube 333$g$, at independently controlled rates of flow, to each exemplary biospecimen 153 in each exemplary bioreactor chamber embodiment of first set of bioreactor chamber embodiments 500 or in each exemplary bioreactor chamber embodiment of second set of bioreactor chamber embodiments 1000 and is thereafter vented to the atmosphere.

5.38 Temperature Control Subsystem of In vitro Support System

Temperature regulation subsystem 240, comprises a circulating temperature control bath unit 241, from which a fluid, such as, for example, water, maintained at a desired temperature, is distributed to a temperature flowmeter regulator multiplier unit 242 and thence through in vitro support system interface 220 either to [i] rectangular water-tight fluid jackets (not shown in FIG. 1, but shown by reference numeral 509 in FIGS. 20A-20G) incorporated into each exemplary bioreactor chamber embodiment of first set of bioreactor chamber embodiments 500, or to [ii] a cylindrical water-tight jacket (not shown in FIG. 1, but shown by reference numeral 623 in FIG. 31) circumscribing an exemplary cylindrical housing (not shown in FIG. 1, but shown by reference numeral 610 in FIG. 31) for the containment of exemplary bioreactor chamber embodiments of second set of bioreactor chamber embodiments 1000, to maintain an ambient temperature about exemplary biospecimen 153.

Thereafter, [i] fluid from the rectangular water-tight fluid jackets 509 of first set of bioreactor chamber embodiments 500 is returned to temperature regulation subsystem. 240 via first efferent temperature tube 334 t and manifold collecting unit 243, thereby completing a closed tubing circuit between temperature regulation subsystem 240 and each of the plurality of exemplary bioreactor chamber embodiments; and, [ii] fluid from the cylindrical water-tight jacket 623 (FIG. 31) circumscribing the exemplary cylindrical housing 610 (FIG. 31) for the containment of second set of bioreactor chamber embodiments 1000 is returned to temperature regulation subsystem 240 via a second efferent temperature tube 394$t$ and manifold collecting unit 243, thereby completing a closed tubing circuit between temperature regulation subsystem 240 and the exemplary cylindrical housing for the containment of second set of bioreactor chamber embodiments 1000.

5.39 Solid Geometry of Transverse Electromagnet

FIG. 2 shows a perspective schematic illustration of transverse electromagnet 400 of first exemplary embodiment of the invention 101 (FIG. 1). In FIG. 2, dashed lines outline vertical mid-plane 432, horizontal mid-plane 433, and axial mid-plane 434 of transverse electromagnet 400. Dashed line 431 defines a vertical z-axis of transverse electromagnet 400, and is formed by the intersection of vertical mid-plane 432 with axial mid-plane 434. Dashed line 437 defines a y-axis of transverse electromagnet 400, and is formed by the intersection of vertical midplane 432 with horizontal midplane 433. Dashed line 459 defines an x-axis of transverse electromagnet 400, and is formed by the intersection of horizontal mid-plane 433 with axial mid-plane 434. Accordingly, z-axis 431, y-axis 437, and x-axis 459 form the axes of a right-handed Cartesian coordinate system within which transverse electromagnet 400 is centered.

FIG. 3 is a cross-sectional view of transverse electromagnet 400 parallel to horizontal midplane 433 of FIG. 2 and taken along line 3-3 of FIG. 1

Figure 4:
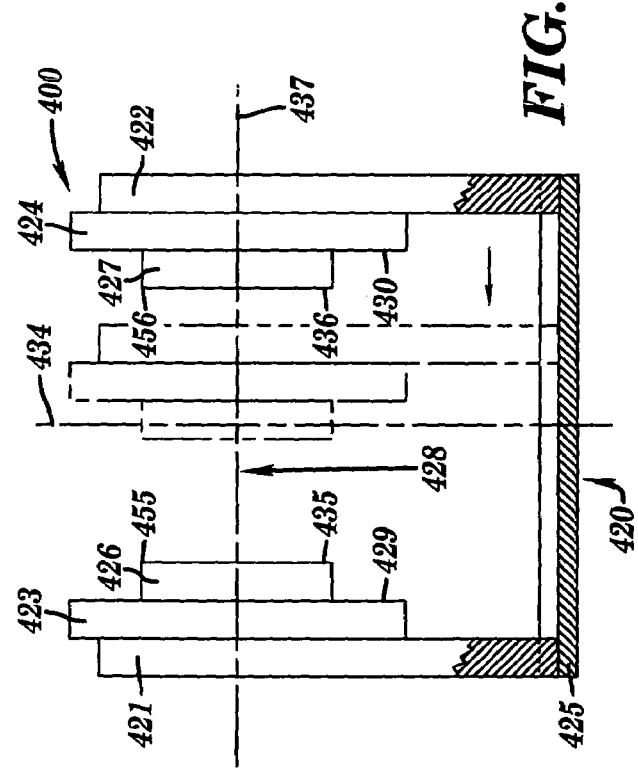
FIG. 4 is a cross-sectional view of transverse electromagnet of a first exemplary embodiment of the invention taken along line 4-4 of FIG. 3.

FIG. 4 is a cross-sectional view of transverse electromagnet 400 parallel to vertical midplane 432 of FIG. 2, and taken along line 4-4 of FIG. 3.

Figure 5:
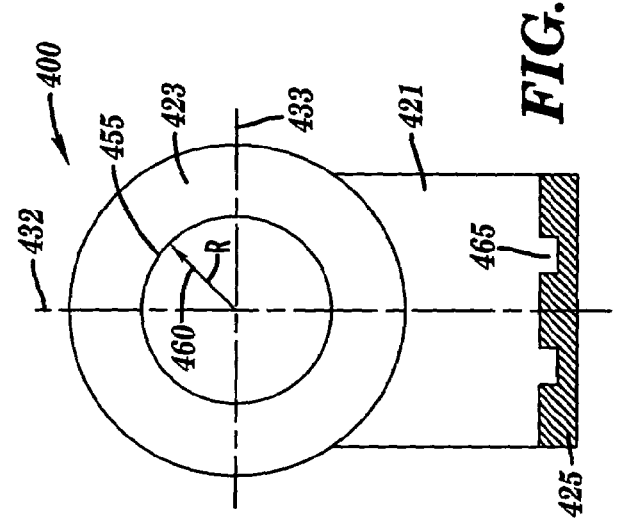
FIG. 5 is a cross-sectional view of view of transverse electromagnet of a, first exemplary embodiment of the invention taken along line 5-5 of FIG. 3.

FIG. 5 is a cross-sectional view of view of transverse electromagnet 400 parallel to axial midplane 434 of FIG. 2 and taken along line 5-5 of FIG. 3.

5.40 Structure of Transverse Electromagnet

In FIGS. 2 through 5, transverse electromagnet 400, comprises a first transverse electromagnet support member 421 and an opposing second transverse electromagnet support member 422. Transverse electromagnet support members 421 and 422 respectively support a first transverse electromagnet housing 423 and an opposing second transverse electromagnet housing 424. Transverse electromagnet support members 421 and 422 are slidably mounted upon a base member 425, having, for example, rails or channels 465 (FIG. 3 and FIG. 5), or other guidance means, adapted to slidably engage the bases of transverse electromagnet support members 421 and 422 such that the distance between them may be precisely and continuously varied along y-axis 437 by manual or electromechanical means, such as, for example, microstepping motors or precision screw drives (not shown in FIGS. 3, 4 and 5), whose operation is well known in the mechanical and electromechanical arts.

Base member 425, together with transverse electromagnet support members 421 and 422, first and second transverse electromagnet housings 423 and 424 form yoke 420 for the support and apposition of a first magnetic pole piece 426 and an opposing second magnetic pole piece 427.

First transverse electromagnet housing 423 has a first inner surface 429 and second opposing transverse electromagnet housing 424 has an opposing second inner surface 430. First inner surface 429 faces opposing second inner surface 430. First magnetic pole piece 426 is disposed upon inner surface 429 of first transverse electromagnet housing 423, and opposing second magnetic pole piece 427 is disposed upon second inner surface 430 of second transverse electromagnet housing 424.

First magnetic pole piece 426 and second opposing magnetic pole piece 427 are both generally shaped as right circular cylinders, respectively having a first circular magnetic pole face 435 and an opposing second circular magnetic pole face 436, each of which have a common pole radius R, (also identified by reference numeral 460), respectively terminating at a first pole face margin 455 (FIG. 2 and FIG. 5) and a second pole face margin 456 (FIG. 2 and FIG. 4). Axial mid-plane 434 (FIG. 1 and FIG. 3) is equidistant from opposing inner surfaces 429 and 430, and is also equidistant from opposing circular magnetic pole faces 435 and 436.

First circular magnetic pole face 435 and opposing second circular magnetic pole face 436 are spaced apart from each other, creating an air gap 428 (FIG. 2, FIG. 3 and FIG. 4.). The width of air gap 428 may be continuously varied by the aforesaid manual or electromechanical means used to vary the distance between transverse electromagnet support members 421 and 422 because the width of the air gap is necessarily determined by the distance between transverse electromagnet support members 421 and 422. Dashed lines in FIG. 4 are used to outline a ghost image of second transverse electromagnet support member 422, whose corresponding second magnetic pole piece 427 is illustrated as having been moved closer to first magnetic pole piece 426 of first transverse electromagnet support member 421, thereby narrowing air gap 428.

Y-axis 437, passes through the geometrical centers of electromagnet pole pieces 426 and 427, and also forms a common central longitudinal axis 437 of transverse electromagnet 400.

The apposition of electromagnet pole pieces 426 and 427 may be accomplished any suitable structure and positioning. Transverse electromagnet support structures 421 and 422 and transverse electromagnet housings 423 and 424 may have any other suitable shape depending, inter alia, on the type and arrangement of electromagnet coils (not shown in FIGS. 1 through 5).

It will be appreciated by those skilled in the art that, the particular mechanical design of the components for holding together and apposing transverse electromagnet support structures 421 and 422 are exemplary only and that many other arrangements for adjusting the positions of the magnetic pole pieces 426 and 427 may be used which are within the scope and spirit of the present invention FIG. 6A shows a perspective schematic illustration of a region of space 438 between two coaxial concentric right circular cylinders 441 and 442 extending between poles faces 435 and 436 in air gap 428. Region of space 438 also appears in FIG. 1 and FIG. 2. FIG. 6A is an enlarged perspective view of region of space 438, in which, for the sake of clarity, all of the other elements of first exemplary embodiment of the invention appearing in FIG. 1 and FIG. 2 have been removed.

FIG. 7 is a cross-sectional view parallel to vertical mid-plane 432 of FIG. 2, and taken along line 4-4 of FIG. 3, of region of space 438 between the two coaxial concentric right circular cylinders 441 and 442 extending between poles faces 435 and 436 in air gap 428, in which, for the sake of clarity, all of the other elements of first exemplary embodiment of the invention appearing in FIG. 1 and FIG. 2 have been removed.

FIG. 6A and FIG. 7 illustrate exemplary biospecimen 153, supported in an exemplary bioreactor chamber embodiment of first set of bioreactor chamber embodiments 500, appearing schematically as a cube disposed in region of space 438. Diamagnetic body force $F_B$ [154] is induced in biospecimen 153 by a diamagnetic field (not shown in FIG. 6A and FIG. 7) generated in space 438 by the invention.

5.41 Space of a Diamagnetic Force Field as an Annular Solid between Concentric Right Circular Cylinders Region of space 438 comprises the space between a first outer right circular cylinder 441 concentric with a second inner right circular cylinder 442, which concentric cylinders have a first coplanar base coincident with the plane of first circular pole face 435 of first magnetic pole piece 426, and a second coplanar base coincident with the plane of second circular pole face 436 of second opposing magnetic pole piece 427. Concentric cylinders 441 and 442 extend between circular pole faces 435 and 436 of magnetic pole pieces 426 and 427, and are centered about common central longitudinal (y-) axis 437 of magnetic pole pieces 426 and 427. First outer right circular cylinder 441 has a first outer radius $R_1$ (also identified by reference numeral 461) greater than the common pole radius R [460] of circular margins 455 and 456 of circular pole faces 435 and 436. Second inner right circular cylinder has a second inner radius $R_2$ (also identified by reference numeral 462), less than the common pole radius R [460] of circular margins 455 and 456 of circular pole faces 435 and 436.

FIG. 8 is an illustrative graph of the radial variation of the magnitude of a magnetic field inductance B(r) (identified by curves 170) in region of space 438, in the vicinity of a circular margin 455 or 456, at pole radius R, of either circular magnetic pole face 435 or 436 of transverse electromagnet 400. In FIG. 8, the ordinate, labeled "B(r) (TESLA)," shows the magnitude of the magnetic field inductance, as a function of the relative radial distance r, in centimeters, along z-axis 431 within axial plane 434 and near pole radius R of either circular magnetic pole face 435 or 436. The solid curve in FIG. 8 illustrates an exemplary radial variation of the magnitude of magnetic field inductance B(r) as measured along the vertical z axis 431 of transverse electromagnet 400. The variably dashed lines in FIG. 8 are respectively illustrative of the radial variation of the magnitude of a magnetic field inductance B(r) measured on the axial mid-plane 434 at 1 cm to each side of the vertical z-axis 431 of transverse electromagnet 400.

In FIG. 8, pole radius R is assigned the value zero on the abscissa, and is identified by the legend appearing along the ordinate "EDGE OF MAGNET." In FIG. 8, points within either circular pole face 435 or 436 are shown to the left as having negative centimeter values along the abscissa, and are identified by the legend "INSIDE MAGNET;" and, points outside either circular pole face 435 or 436 are shown to the right as having positive centimeter values along the abscissa, and are identified by the legend "OUTSIDE MAGNET." By way of example, in FIG. 8, inside either circular pole face 435 or 436, the magnetic field inductance B(r) has a constant value of about 1.2 Tesla for values of r less than about −2 cm. Outside either circular pole face 435 or 436, magnetic field inductance B(r) has a declining value, being less than about 0.2 Tesla for values of r greater than about +2 cm.

A point corresponding to first outer radius $R_1$ of first outer right circular cylinder 441, appearing in FIG. 6A, 6B and FIG. 7, is shown to the right of the ordinate at R=0 in FIG. 8; and, a point corresponding to second inner radius $R_2$ of second inner right circular cylinder 442, appearing in FIG. 6A, 6B and FIG. 7, is shown to the left of the ordinate at R=0 in FIG. 8.

FIG. 9 is an illustrative graph of the radial variation of the magnitude of the magnetic field-field gradient product B(r)∂B/∂r (identified by curves 182) in region of space 438, in the vicinity of circular margin 455 or 456, at pole radius R, of either magnetic pole face 435 or 436 of transverse electromagnet 400. In FIG. 9, the ordinate shows the magnitude of the magnetic field-field gradient product B(r)∂B/∂r in square Tesla per meter ($T^2$/m), as a function of the relative radial distance r, in centimeters, along z-axis 431 within axial plane 434 and near pole radius R of either circular magnetic pole face 435 or 436. The solid line in FIG. 9 illustrates the radial variation of the magnitude of a magnetic field-field gradient product B(r)∂B/∂r as measured along the vertical z axis 431 of transverse electromagnet 400. The variably dashed lines in FIG. 8 are illustrative of the radial variation of the magnitude of a magnetic field-field gradient product B(r)∂B/∂r measured on the axial mid-plane 434 at 1 cm to each side of the vertical z axis 431 of transverse electromagnet 400.

In FIG. 9, fixed radius R [460] is assigned the value zero on the abscissa, and is identified by the legend appearing along the ordinate "EDGE OF MAGNET." In FIG. 9, points within either circular pole face 435 or 436 are shown to the left as having negative centimeter values along the abscissa, and are identified by the legend "INSIDE MAGNET." First outer radius $R_1$ of first outer right circular cylinder 441, appearing in FIG. 6A, 6B and FIG. 7, is shown to the right of the ordinate at r=0 in FIG. 9; and, second inner radius $R_2$ of second inner right circular cylinder 442, appearing in FIG. 6A, 6B and FIG. 7, is shown to the left of the ordinate at r=0 in FIG. 9. In FIG. 9, points outside either circular pole face 435 or 436 are shown to the right as having positive centimeter values along the abscissa, and are identified by the legend "OUTSIDE MAGNET."

By way of example, in FIG. 9, inside either circular pole face 435 or 436, the magnetic field-field gradient product B(r)∂B/∂r has a value that ascends for values of r greater than about −2 cm to a maximum radial value of about 45 $T^2$/m at about r=0; and, outside either of circular pole face 435 or 436, the magnetic field-field gradient product B(r)∂B/∂r has a value that declines from about 45 $T^2$/m, being less than about 4 $T^2$/m for values of r greater than +2 cm.

By comparing FIG. 6A and FIG. 7, with the graph of FIG. 8, it can be seen that within air gap 428, for all radii extending from common central longitudinal central (y-) axis 437 that are less than about $R_2$ [462], transverse electromagnet 400 generates a magnetic field inductance B(r) having a generally constant magnitude.

By comparing in FIG. 6A and FIG. 7, with the graph of FIG. 8, it can be seen that within air gap 428, for all radii extending from common central longitudinal (y-) axis 437 that are greater than about $R_1$ [461], transverse electromagnet 400 generates an increasingly negligible magnetic field inductance B(r) [170].

By comparing FIG. 6A and FIG. 7, with the graph of FIG. 8 and the graph of FIG. 9, it can also be seen that within air gap 428 at pole radius R [460], the magnitude of the magnetic field-field gradient product B(r)∂B/∂r of transverse electromagnet 400 has a radial maximum value, with respect to which a first threshold radial value may be defined at $R_1$ [461], corresponding to 5% of the maximum radial value; and, with respect to which a second threshold radial value may be defined at $R_2$ [462], also corresponding to 5% of the maximum radial value.

By comparing FIG. 6A and FIG. 7, with the graph of FIG. 8 and the graph of FIG. 9, it can be seen that within air gap 428, for all radii extending from common central longitudinal (y-) axis 437 that are greater than about $R_2$ [462], but less than about $R_1$ [461], i.e., in region of space 438, transverse electromagnet 400 has a magnetic field-field gradient product B(r)∂B/∂r productive of a diamagnetic force field, as described supra., that generates a diamagnetic body force $F_B$ [154], also as described supra., internal to exemplary biospecimen 153, supported in an exemplary bioreactor chamber of first set of bioreactor chamber embodiments 500.

5.42 Polygonal Pole Faces

First circular magnetic pole face 435 and opposing second circular magnetic pole face 436 (FIG. 6A) are exemplary limiting cases, as n goes to infinity, of pole faces having any n-sided regular polygonal perimeter. Accordingly, as shown in FIG. 6B, first circular pole face 435 and opposing second circular pole face 436 may be modified to form a first modified pole face 435m and a second modified pole face 436m having perimeters in the form of congruent n-sided regular polygons inscribing a circle of pole radius R [460].

5.43 Space of a Diamagnetic Force Field as a Prismatic Polyhedral Solid between Concentric Prismatic Polyhedrons FIG. 6B is a perspective schematic illustration of region of space 438 between exemplary concentric hexagonal prismatic polyhedrons 441p and 442p respectively inscribed in concentric coaxial right circular cylinders 441 and 442 (FIG. 6A) extending between first and second modified poles faces 435m and 436m and within air gap 438 of transverse electromagnet 400, in which, for the sake of clarity, all of the other elements of first exemplary embodiment of the invention appearing in FIG. 1 and FIG. 3 have been removed.

In FIG. 6B, transverse electromagnet 400 has exemplary first and second hexagonal magnetic pole faces 435m and 436m wherein circular pole faces 435 and 436 (FIG. 6A) have been modified so that their respective perimeters now form congruent n-sided regular polygons inscribed in circles of pole radius radius R [460], where n=6. In FIG. 6B, region of space 438 comprises the space between two concentric hexagonal prismatic polyhedrons as follows: a first outer hexagonal prismatic polyhedron 441p having as its bases two opposing and congruent hexagons respectively inscribing a circle of outer radius $R_1$ [461], and a second inner hexagonal prismatic polyhedron 442p having as its bases two opposing and congruent hexagons respectively inscribing a circle of inner radius $R_2$ [462]. Consequently first outer hexagonal prismatic polyhedron 441p inscribes first outer right circular cylinder 441 and second inner hexagonal prismatic polyhedron 442p inscribes second inner right circular cylinder 442. The concentric hexagonal prismatic polyhedrons 441p and 442p have a first coplanar base coincident with the plane of first modified pole face 435m and a second coplanar base coincident with the plane of second modified pole face 436m. The concentric hexagonal prismatic polyhedrons accordingly extend between modified pole faces 435*m* and 436*m* of magnetic pole pieces 426 and 427, and are centered about common central longitudinal (y-) axis 437 of magnetic pole pieces 426 and 427.

In FIG. 6A, FIG. 6B and FIG. 7, the diamagnetic body force $F_B$ [154] that is caused to arise within exemplary biological specimen 153 by the diamagnetic force field (not shown) generated by transverse electromagnet 400 in region of space 438, has a direction given by the direction of the gradient of the magnetic inductance $\partial B(r)/\partial r$ and is always directed radially outward from common longitudinal central (y-) axis 437. The magnitude of the diamagnetic body force $F_B$ [154], that is caused to arise within biological specimen 153 by the diamagnetic force field (not shown) generated by transverse electromagnet 400, is given by equation (5) supra., $|F_B|=(\chi/\mu_0) B(r)\partial B/\partial r$, wherein the variable z has been replaced by the variable r, with r taking on values between and including $R_1$ [461] and $R_2$ [462].

In the exemplary case of FIG. 9, at about pole radius R, the diamagnetic force field has a maximum diamagnetic field strength corresponding to the maximum radial value of the magnet field-field gradient product $B(R)\partial B/\partial r$ of about 45 $T^2/m$. First outer radius $R_1$ [461] is selected such that at all points comprising first outer right circular cylinder 441 having radius $R_1$, the diamagnetic force field has a first threshold diamagnetic field strength corresponding to the first threshold radial value of the magnetic field-field gradient product $B(R_1) \partial B(R_1)/\partial r$ that is defined as about 5% of the exemplary maximum radial value of the magnet field-field gradient product $B(R) \partial B(R)/\partial r$ of about 45 $T^2/m$, or about 2.25 $T^2/m$. Second inner radius $R_2$ [462] is selected such that at all points comprising second inner right circular cylinder 442 having radius $R_2$, the diamagnetic force field has a second threshold diamagnetic field strength corresponding to a second threshold radial value of the magnetic field-field gradient product $B(R_2) \partial B(R_2)/\partial r$ that is also defined as about 5% of the exemplary maximum radial value of the magnet field-field gradient product $B(R) \partial B(R)/\partial r$ of about 45 $T^2/m$, or about 2.25 $T^2/m$.

Accordingly, bioreactor positioning system 300 of first exemplary embodiment of the invention 101, disposes first set of exemplary bioreactor chamber embodiments 500 housing exemplary biospecimens 153 sustained by biological in vitro support system 200, in a space 438 comprising a region of space between and including first outer right circular cylinder 441, having first outer radius $R_1$ [461] that is greater than pole radius R [460], at which first outer radius $R_1$ [461] the magnetic field-field gradient product $B(r=R_1)B/\partial r$ has a first threshold radial value, which first outer right circular cylinder 441 is concentric with second inner right circular cylinder 442, having second inner radius $R_2$ [462] that is less than pole radius R [460], at which second inner radius $R_2$ [462] the magnetic field-field gradient product $B(r=R_2)B/\partial r$ has a second threshold radial value.

The concentric right circular cylinders 441 and 442 have a first coplanar base coincident with a first plane of first circular face 435 having pole radius R [460], at which pole radius R [460] the magnetic field-field gradient product $B(r=R)B/\partial r$ has a maximum radial value; and the concentric right circular cylinders 441 and 442 have a second coplanar base coincident with a with a second plane of second circular face 436 also having pole radius R [460], at which pole radius R [460] the magnetic field-field gradient product $B(r=R)B/\partial r$ also has the maximum radial value. The concentric right circular cylinders 441 and 442 are centered about central longitudinal (y-) axis 437 and extend between first circular pole face 435 and second circular pole face 436 of transverse electromagnet 400.

For example, when transverse electromagnet 400 produces a uniform magnetic inductance B of about 1.6 Tesla interior to circular margins 455 and 456 of circular poles faces 435 and 436, respectively, and with air gap 428 being about 1 cm in width, there is created a magnetic field-field gradient product $B(r)\partial B/\partial r$ of about 160 $T^2/m$, inductive of a diamagnetic body force $F_B$ [154] that may yield a weight reduction in an exemplary in vitro biospecimen 153 disposed in region of space 438 of about 10% to 12% at the Earth's surface.

This value range of 10% -12% is obtained by evaluating the ratio of the diamagnetic body force $F_B$ induced in the exemplary in vitro biospecimen (given by equation (5), supra.) to the gravitational force $F_G$ acting on the exemplary in vitro biospecimen (given by equation (6), supra.), with values of a magnetic field-field gradient product $B(r)\partial B/\partial r$ of about 160 $T^2/m$, a magnetic field magnitude B of about 1.6 Tesla, a terrestrial acceleration of gravitational of 9.81 $m/s^2$, and using the density $\rho_w$=993 Kg/m3 and magnetic susceptibility $\chi_w=-9.03\times10^{-6}$ of water, since water is the main component of cells and tissues. The ratio $|F_B|/|F_G|=(\chi_w/\mu_0\rho_w g) \partial B/\partial r$ yields about 0.12, demonstrating that a weight reduction in an in vitro biospecimen of about 12% can be achieved with the present invention on the Earth's surface.

By modifying the geometry of circular magnetic pole faces 425 and 436, for example, by using pole caps having a conical shape, or by machining pole pieces 426 and 427 so that they have conically projecting pole faces; and, by reducing the width of air gap 428; and, by increasing the driving current to transverse electromagnet 400 to values within the saturation limits of the material comprising magnetic pole pieces 425 and 426, a magnetic field-field gradient product $B(r)\partial B/\partial r$ of about 300 $T^2/m$ may be attained that is capable of inducing a diamagnetic body force $F_B$ productive of a weight reduction in an exemplary in vitro biospecimen disposed in region of space 438 of about 22% at the Earth's surface, as can be readily obtained by evaluating the ratio $|F_B|/|F_G|$ in equation (12), supra. Larger percentages of weight reduction reflecting larger reductions in gravity may be calculated by extrapolation.

FIG. 10 is another cross-sectional view of transverse electromagnet 400 of first exemplary embodiment of the invention 101 parallel to vertical midplane 432 of FIG. 2, and taken along line 4-4 of FIG. 3, illustrating the interaction of the diamagnetic body force $F_B$ [154 ] with a force of gravity $F_G$ [164 ] at different locations. FIG. 10 shows exemplary biospecimen 153, represented as a small circle, supported in three exemplary bioreactor chamber embodiments of first set of bioreactor chamber embodiments 500, each having the shape of a rectangular parallelepiped with respective long axes 809*ax*, 809*bx*, and 809*cx* oriented horizontally, i.e., perpendicular to z-axis 431. For purposes of illustration, FIG. 10 shows biospecimen 153 in three exemplary locations:

[i] within spatial region 438 and superiorly in air gap 428, at location 468; and,

[ii] within spatial region 438, and inferiorly in air gap 428, at location 469; and,

[iii] outside of spatial region 438, centrally in air gap 428 at location 478, upon common central longitudinal (y-) axis 437.

When, for example, exemplary biospecimen 153 is placed in location 468 of FIG. 10, there is generated within it diamagnetic body force $F_B$ [154] that opposes gravitational force $F_G$ [164], thereby reducing the weight of biospecimen 153.

When, for example, biospecimen 153 is placed in location 469 of FIG. 10, there is generated within it diamagnetic body force $F_B$ [154] that aligns with gravitational force $F_G$ [164], thereby increasing the weight of biospecimen 153.

When, for example, biospecimen 153 is placed in location 478 of FIG. 10, no diamagnetic body force is generated within biospecimen 153, and gravitational force $F_G$ [164] acting on biospecimen 153 is unaltered.

The foregoing examples demonstrate that transverse electromagnet 400 of first embodiment of the invention 101 induces a diamagnetic body force $F_B$ [154] in exemplary biospecimen 153, sustained in region of space 438 by biological in vitro support system 200 and disposed in region of space 438 by bioreactor chamber positioning system 300, having a variable direction with respect to the coordinate system of modified transverse magnet 400 and with respect to a direction of vector of a secondary body force, such as gravitational force $F_G$ [164].

Referring next to FIG. 11, showing a more detailed perspective schematic view of first exemplary embodiment of the invention 101, with computer 201 (FIG. 1) and biological in vitro support system 200 (FIG. 1) omitted, first exemplary embodiment of bioreactor positioning system 300 sustains at least one exemplary biospecimen 153 in vitro in at least one of a plurality of exemplary bioreactor chamber embodiments forming a first set of bioreactor chamber embodiments 500 and disposes exemplary biospecimen 153 within a diamagnetic force field $D_B$ (not shown in FIG. 11) generated by transverse electromagnet 400 in spatial region 438, so that there is induced in biospecimen 153 a diamagnetic body force $F_B$ [154], as described, supra.

5.44 Bioreactor Positioning System

To that end, inferior surface 301 of upright bioreactor positioning system column 302 is slidably mounted upon superior surface 303 of bioreactor positioning system platform 304. Superior surface 303 of bioreactor positioning system platform 304 has, for example, rails, tracks, or grooves 309, arranged parallel to x-axis 459 of transverse electromagnet 400, (hereinafter "x-axis tracks" 309) and adapted to slidably engage inferior surface 301 of upright bioreactor positioning system column 302, such that upright bioreactor positioning system column 302 is caused to move continuously along x-axis tracks 309, including movement in an oscillatory fashion, as directed by manual or computerized electromechanical means, such as, for example a computer-controlled horizontal microstepping motor 350 or precision screw drives (not shown in FIG. 11), well known in the electromechanical arts.

Nonmagnetic positioning arm 305, having anterior terminus 306 and posterior terminus 307, is slidably mounted upon anterior surface 308 of upright bioreactor positioning system column 302. Anterior surface 308 has, for example, rails, tracks, or grooves 310 arranged parallel to z-axis 431 of transverse electromagnet 400 (hereinafter "z-axis tracks" 310) and adapted to slidably engage posterior terminus 307 of positioning arm 305 such that nonmagnetic positioning arm 305 is caused to move continuously along z-axis tracks 310, including movement in an oscillatory fashion, as directed by manual or computerized electromechanical means, such as, for example, computer-controlled vertical microstepping motor 360, or precision screw drives (not shown in FIG. 11), well known in the electromechanical arts.

Anterior terminus 306 of nonmagnetic positioning arm 305 is adapted to make exchangeably detachable connections with either [i] an exemplary rectilinear frame 311, (shown in greater detail in FIG. 12), or [ii] an exemplary circular frame 370, shown in FIG. 13, both being made of a nonmagnetic material, such as, for example, Nylon, Plexiglass® (polymethylmethacrylate), Lexan® polycarbonate resin, or a substantially equivalent material.

Exemplary rectilinear frame 311, shown in FIG. 12, supports either [i] an exemplary radially slotted rectilinear insert 800, (shown in FIG. 14), or [ii] an exemplary tangentially slotted rectilinear insert 825, (FIG. 11 and shown in greater detail in FIG. 16), for securing and orienting in spatial region 438 one or more exemplary bioreactor chamber embodiments, forming first set of bioreactor chamber embodiments 500 (shown in FIG. 15, FIG. 17, FIG., 18, FIG. 19 and FIGS. 20A through 20G), which bioreactor chamber embodiments house and sustain exemplary biospecimens, such as biospecimen 153 (not shown in FIG. 12), in vitro within the diamagnetic force field generated in spatial region 438 by transverse electromagnet 400 of first exemplary embodiment of the invention 101.

Exemplary circular frame 370 (FIG. 13) also supports either [iii] an exemplary radially slotted circular insert 850 (shown in FIG. 18), or [iv] an exemplary tangentially slotted circular insert 875 (shown in FIG. 19), for securing and orienting in spatial region 438 one or more exemplary bioreactor chamber embodiments, forming a first set of bioreactor chamber embodiments 500 (shown in FIG. 15, FIG. 17, FIG. 18, FIG. 19, and FIGS. 20A through 20G), which bioreactor chamber embodiments house and sustain biospecimens 153 (not shown in FIG. 13) in vitro within the diamagnetic field generated in spatial region 438 by transverse electromagnet 400 of first exemplary embodiment of the invention 101.

In FIG. 1, the motion of upright bioreactor positioning system column 302 along x-axis tracks 309 and the motion of nonmagnetic positioning arm 305 along z-axis tracks 310 precisely aligns either:

[i] exemplary radially slotted rectilinear insert 800 (FIG. 14) held in exemplary rectilinear frame 311 (FIG. 12); or,

[ii] exemplary tangentially slotted rectilinear insert 825 (FIG. 16) held in exemplary rectilinear frame 311 (FIG. 12); or

[iii] exemplary radially slotted circular insert 850 (FIG. 18) held in exemplary circular frame 370 (FIG. 13); or,

[iv] exemplary tangentially slotted circular insert 875 (FIG. 19) held in exemplary circular frame 370 (FIG. 13)

within spatial region 438, thereby disposing one or more biospecimens 153 housed and sustained in biological chambers carried by inserts 800, 825, 850 or 875 in spatial region 438—the region corresponding to the effective spatial distribution of the diamagnetic force field generated by transverse electromagnet 400 of first exemplary embodiment of the invention 101, so that there is induced in the biospecimens 153 diamagnetic body force $F_B$ [154].

5.45 Exemplary Rectilinear Frame of Bioreactor Positioning System

As shown in FIG. 12, exemplary rectilinear frame 311, comprises superior member 326, first lateral member 327, and second lateral member 328 to which nonmagnetic positioning arm 305 is detachably connected. Superior member 326 of exemplary rectilinear frame 311 may, for example, be about 34 cm in length, about 3 cm wide (thick) and about 4 cm in height. First lateral member 327, and second lateral member 328 may each, for example, be about 26 cm in length, about 3 cm wide (thick) and about 4 cm in height. Superior member 326, first lateral member 327, and second lateral member 328 may be made of Nylon, Plexiglass® (polymethylmethacrylate), Lexan® polycarbonate resin, or a substantially equivalent nonmagnetic material.

Superior member 326 of exemplary rectilinear frame 311 has inferior surface 342 and superior surface 341, respectively drilled with a plurality of corresponding exemplary inner openings 331 and exemplary outer openings 332, thereby forming a plurality of frame tubing conduits 338f. First lateral member 327 of exemplary rectilinear frame 311 has inner surface 329 and outer surface 340, also respectively drilled with a plurality of corresponding exemplary inner openings 331 and exemplary outer openings 332, also forming a plurality of frame tubing conduits 338f.

Frame tubing conduits 338 f are adapted to receive first tubing sets 330, as described, supra., and shown in FIG. 1, comprising first afferent tube bundle 333 and first efferent tube bundle 334.

For example, FIG. 12 shows six exemplary sets of frame tubing conduits 338f, with one such set designated as receiving exemplary first afferent tube bundle 333, comprising first afferent gas tube 333g, first afferent temperature tube 333t, and first afferent perfusion tube 333p, and exemplary first efferent tube bundle 334, comprising first efferent temperature tube 334t and first efferent perfusion tube 334p.

Frame tubing conduits 338f carry first set of tubes 330 to insert tubing conduits 338i of either a radially slotted rectilinear insert 800 (FIG. 14) or tangentially slotted rectilinear insert 825 (FIG. 16) exchangeably held within nonmagnetic rectilinear frame 311, which insert tubing conduits 338i communicate with at least one outer bioreactor chamber holding slot 807a or 807c of either radially slotted rectilinear insert 800 (FIG. 14) or tangentially slotted rectilinear insert, 825 (FIG. 16); and, insert tubing conduits 338i also communicate with a central bioreactor chamber holding slot 807b of radially slotted rectilinear insert 800 (FIG. 14) or tangentially slotted rectilinear insert 825 (FIG. 16).

Superior member 326 and first lateral member 327 of rectilinear frame 311 are also drilled with a plurality of exemplary frame connecting holes 339f for the passage of exemplary screws 343 or substantially equivalent fastening means, made of a nonmagnetic material, such as, for example, nylon, or a substantially equivalent material, with which to fasten either an exemplary radially slotted rectilinear insert 800 (FIG. 14) or an exemplary tangentially slotted rectilinear insert 825 (FIG. 16) to exemplary rectilinear frame 311.

Exemplary radially slotted rectilinear insert 800 (FIG. 14.) and exemplary tangentially slotted rectilinear insert 825, (FIG. 16) contain a plurality of slots for securing and orienting in spatial region 438 one or more exemplary bioreactor chamber embodiments (shown in FIG. 15, FIG. 17, FIG. 18, FIG. 19 and FIGS. 20A through 20G), forming first set of bioreactor chamber embodiments 500, which bioreactor chamber embodiments sustain biospecimens 153 (not shown in FIG. 13) in vitro within the diamagnetic field generated in spatial region 438 by transverse electromagnet 400 of first exemplary embodiment of the invention 101.

5.46 Exemplary Circular Frame of Bioreactor Positioning System

As shown in FIG. 13, exemplary circular frame 370, comprises a three-sided superior member 371, having the general form of an inverted "U," and a linear inferior member 372. Three-sided superior member 371 may be made out of a nonmagnetic material, such as, for example, Nylon, Plexiglass® (polymethylmethacrylate), Lexan® polycarbonate resin, or a substantially equivalent material, having an exemplary thickness of about 3 cm, an exemplary length of about 34 cm and an exemplary height of about 30 cm. Linear inferior member 372 may also be made out of a nonmagnetic material, such as, for example, Nylon, Plexiglass® (polymethylmethacrylate), Lexan® polycarbonate resin, or a substantially equivalent material, having an exemplary thickness of about 3 cm, an exemplary height of about 4 cm and an exemplary length of about 34 cm.

As shown in FIG. 13, three-sided superior member 371 has a superior aspect 373, a first lateral aspect 381 and a second lateral aspect 382, to which second lateral aspect, 382, anterior terminus 306 of nonmagnetic positioning arm 305 is exchangeably and detachably connected. Superior aspect 373 of three-sided superior member 371 and first lateral aspect 381 of three-sided superior member 371 contain a plurality of frame tubing conduits 338 f adapted to receive first tubing sets 330, as described, supra.

Three-sided superior member 371 is adapted to detachably join linear inferior member 372 -such that an inner border 376 of three-sided superior member 371 and an inner border 377 of linear inferior member 372 form an approximately circular perimeter 374 about an approximately circular opening 378 having a first diameter, which approximately circular opening 378 exchangebly and detachably receives either an exemplary radially slotted circular insert 850 (FIG. 18.) having a smaller second diameter or an exemplary tangentially slotted circular insert 875 (FIG. 19) also having a smaller second diameter. Exemplary radially slotted circular insert 850 (FIG. 18.) and exemplary tangentially slotted circular insert 875 contain a plurality of slots 807a, 808b (FIG. 18. and FIG. 19) for securing and orienting in spatial region 438 one or more exemplary bioreactor chamber embodiments (FIG. 15, FIG. 17, FIG. 18, FIG. 19 and FIGS. 20A through 20G), forming first set of bioreactor chamber embodiments 500, which bioreactor chamber embodiments house and sustain biospecimens 153 (not shown in FIG. 13) in vitro within the diamagnetic field generated in spatial region 438 by transverse electromagnet 400 of first exemplary embodiment of the invention 101.

Inner border 376 of three-sided superior member 371 comprises about 290 degrees of arc of circular perimeter 374, and an arcuate track 375 is sculpted into linear inferior member 372 so as to comprise a complementary arc of about 70 degrees, thereby completing 360 degrees of arc of circular perimeter 374 about circular opening 378. The first diameter of circular perimeter 374 may, for example, be about 28 cm; and, the smaller second diameter of either exemplary radially slotted circular insert 850 (FIG. 18.) or exemplary tangentially slotted circular insert 875 (FIG. 19) may, for example, be about 26 cm.

Exemplary radially slotted circular insert 850 (FIG. 18.) or exemplary tangentially slotted circular insert 875 (FIG. 19) are supported by arcuate track 375 (FIG. 13) to be freely rotatable within approximately circular opening 378, about common longitudinal central (y-) axis 437 of transverse electromagnet 400. Arcuate track 375 may, for example, have a width of about 1 cm and a depth of about 2 cm. A nonmagnetic positioning screw 379, or substantially equivalent locking device, is incorporated in linear inferior member 272 to lock either exemplary radially slotted circular insert 850 (FIG. 18.) or exemplary tangentially slotted circular insert 875 (FIG. 19.) into position, following their rotation to a desired angular orientation that is measured with respect to an exemplary protractor scale 380, shown in FIG. 13 as etched onto linear inferior member 272. Nonmagnetic positioning screw 379 may be made of Nylon, Plexiglass® (polymethylmethacrylate), Lexan® polycarbonate resin, or a substantially equivalent material.

Turning next to the inserts available for insertion into rectilinear frame 311, FIG. 14 is a schematic illustration of an exemplary radially slotted rectilinear insert 800 for use with the exemplary rectilinear frame 311 shown in FIG. 12. In FIG. 14, exemplary radially slotted rectilinear insert 800 is shown without any of the exemplary bioreactor chamber embodiments forming first set of bioreactor chamber embodiments 500. In FIG. 15, exemplary radially slotted rectilinear insert 800 of FIG. 14 is shown together with three identical exemplary bioreactor chambers 809a, 809b, 809c of first set of bioreactor chamber embodiments 500.

5.47 Exemplary Radially Slotted Rectilinear Insert

In FIG. 14, exemplary radially slotted rectilinear insert 800 is seen to have the general form of a thin rectangular parallelepiped, having a superior aspect 801, an inferior aspect 802, a first lateral aspect 803 and a second lateral aspect 804. Exemplary radially slotted rectilinear insert 800 may, for example, be made of a square sheet of nonmagnetic material, such as, for example, Nylon, Plexiglass® (polymethylmethacrylate), Lexan® polycarbonate resin, or a substantially equivalent material, measuring about 26 cm. on a side and having a thickness of about 1 cm. Imaginary circle 805, having a radius equal to pole radius R [460] of either first or second circular pole faces 435, 436 of transverse electromagnet 400 (FIG. 2 and FIG. 5) is centered about a geometric center 806 of radially slotted rectilinear insert 800. A horizontal line extending between a first lateral pole 810fl at 90 degrees in FIG. 14 and a second lateral pole 810sl at 270 degrees in FIG. 14 represents a horizontal meridian 810. A vertical line extending between a superior pole 811s at 180 degrees in FIG. 14 and an inferior pole 811i at zero degrees in FIG. 14 represents a vertical meridian 811.

When exemplary radially slotted rectilinear insert 800 is inserted into rectilinear frame 311 and secured therein, computer-controlled horizontal microstepping motor 350 (FIG. 11) and computer-controlled vertical microstepping motor 360 (FIG. 11) are activated to initially position radially slotted rectilinear insert 800 so that geometric center 806 of imaginary circle 805 is intersected by common longitudinal central (y-) axis 437 of transverse electromagnet 400 and the perimeter of imaginary circle 805 is aligned with first and second circular pole face margins 455 and 456 of first and second circular pole faces 435 and 436 of transverse electromagnet 400 (FIG. 2 and FIG. 5). The direction of the terrestrial force of gravity is shown in FIG. 14 by gravitational force vector $F_G$ [164].

A plurality of insert connecting holes, 339i, along two aspects of exemplary radially slotted rectilinear insert 800 are adapted to receive corresponding nonmagnetic screws 343 (not shown in FIG. 14), or substantially equivalent fastening devices, enabling exemplary radially slotted rectilinear insert 800 to be secured within exemplary rectilinear frame 311 in two alternative orientations—a vertical orientation of holding slots and a horizontal orientation of holding slots.

Superior aspect 801 and first lateral aspect 803 of exemplary radially slotted rectilinear insert 800 are drilled with a plurality of insert tubing conduits 338i, complementary to and interfacing with frame tubing conduits 338f of rectilinear frame 311, which insert tubing conduits 338i receive first tubing sets 330 (FIG. 1). Insert tubing conduits 338i conduct first tubing sets 330 to exemplary ports 808a, 808b, and 808c of exemplary first outer bioreactor chamber holding slot 807a, exemplary central bioreactor chamber holding slot 807b, and exemplary second outer bioreactor chamber holding slot 807c respectively, cut into exemplary radially slotted rectilinear insert 800.

Exemplary first outer bioreactor chamber holding slot 807a, exemplary central bioreactor holding slot 807b, and exemplary second outer bioreactor chamber holding slot 807c are full-thickness cutouts made in exemplary radially slotted rectilinear insert 800, each having a generally rectangular form, with a length of about 5-10 cm and width of about 5 cm. The variable 5-10 cm length is required to allow for tubes carried by insert tubing conduits 338i to remain straight as they extend to the lower bioreactor holding slots 807b and 807c from the superior aspect 801 of the exemplary radially slotted rectilinear insert 800.

Opposing full-thickness notches 812n are respectively cut into opposing sides of exemplary first outer bioreactor chamber holding slot 807a, exemplary central bioreactor holding slot 807b, and exemplary second outer bioreactor chamber holding slot 807c to receive complementary tabs 812t (not shown in FIG. 14) of exemplary bioreactor chamber embodiments forming first set of bioreactor chamber embodiments 500, which tabs are more fully described infra.

In FIG. 15, exemplary radially slotted rectilinear insert 800 of FIG. 14., for use with the exemplary rectilinear frame 311 shown in FIG. 12., is shown with three identical exemplary bioreactor chambers 809a, 809b, and 809c having respective long axes 809ax, 809bx and 809cx. Each bioreactor chamber also has a geometrical center point (not shown). Exemplary bioreactor chambers 809a, 809b, and 809c are removably and exchangeably secured in exemplary first outer bioreactor chamber holding slot 807a, exemplary central bioreactor chamber holding slot 807b, and exemplary second outer bioreactor chamber holding slot 807c respectively, by tabs 812t that insert into corresponding notches 812n. Tabs 812t are fashioned at opposing ends of each exemplary bioreactor chamber 809a, 809b, and 809c and are intersected by their long axes 809ax, 809bx and 809cx.

Tabs 812t are adapted to respectively fit into complementary notches 812n of exemplary first outer bioreactor chamber holding slot 807a, exemplary central bioreactor holding slot 807b, and exemplary second outer bioreactor chamber holding slot 807c of exemplary radially slotted rectilinear insert 800. Notches 812n are cut into sides of exemplary first outer bioreactor chamber holding slot 807a, exemplary central bioreactor holding slot 807b, and exemplary second outer bioreactor chamber holding slot 807c so as to orient long axes 809ax, 809bx, and 809cx, of respective exemplary bioreactor chambers 809a, 809b and 809c, radially with respect to imaginary circle 805 on exemplary radially slotted rectilinear insert 800.

The intersection of the plane of exemplary radially slotted rectilinear insert 800 with spatial region 438 (FIG. 6A and FIG. 7), within which the diamagnetic force field is generated by transverse electromagnet 400 of first exemplary embodiment of the invention 101, is shown in FIG. 15 as annulus 813 about imaginary circle 805 of radius R [460].

First exemplary outer bioreactor chamber holding slot 807a is cut into radially slotted rectilinear insert 800 so as to orient long axis 809ax of exemplary bioreactor chamber 809a, when held therein, coincident with pole radius R [460] and vertical meridian 811, and to dispose bioreactor chamber 809a within region 438 (FIG. 6A and FIG. 7) superiorly between first outer radius $R_1$ [461] (FIG. 6A and FIG. 7) of first outer right circular cylinder 441 (FIG. 6A and FIG. 7) and second inner radius $R_2$ [462] (FIG. 6A and FIG. 7) of second inner right circular cylinder 442 (FIG. 6A and FIG. 7).

Second exemplary outer bioreactor chamber holding slot 807c is cut into radially slotted rectilinear insert 800 so as to orient long axis 809cx of exemplary bioreactor chamber 809c, when held therein, coincident with pole radius R [460]

and vertical meridian 811, and to dispose bioreactor chamber 809c within region 438 (FIG. 6A and FIG. 7) inferiorly between first outer radius R₁ [461] (FIG. 6A and FIG. 7) of first outer right circular cylinder 441 (FIG. 6A and FIG. 7) and second inner radius R₂ (462) (FIG. 6A and FIG. 7) of second inner right circular cylinder 442 (FIG. 6A and FIG. 7).

Exemplary central bioreactor chamber holding slot 807b is cut into radially slotted rectilinear insert 800 so as to orient long axis 809bx of exemplary bioreactor chamber 809b, when held therein, coincident with pole radius R [460] and vertical meridian 811, and to place the geometrical center point (not shown) of exemplary bioreactor chamber 809b on central longitudinal (y-) axis 437 (FIG. 6A and FIG. 7) of transverse electromagnet 400 (FIG. 6A and FIG. 7).

In FIG. 15, an exemplary first tubing set 330 is represented by dashed dark lines, within insert tubing conduits 338i, communicating with ports 808b of exemplary central bioreactor chamber holding slot 807b. The intersection of the plane of exemplary radially slotted rectilinear insert 800 with spatial region 438 (FIG. 6A and FIG. 7), within which the diamagnetic force field is generated by transverse electromagnet 400 of first exemplary embodiment of the invention 101, is shown in FIG. 15 as annulus 813 about imaginary circle 805 of radius R [460].

In FIG. 15, exemplary bioreactor chambers 809a, 809b, and 809c are removably and exchangeably secured in exemplary first outer bioreactor chamber holding slot 807a, exemplary central bioreactor chamber holding slot 807b, and exemplary second outer bioreactor chamber holding slot 807c so that a. When the diamagnetic force field occupying region 438, (FIG. 6. and FIG. 7) is activated, exemplary bioreactor chamber 809a in exemplary first outer bioreactor chamber holding slot 807a is disposed in region 438 proximal to superior pole 811s of vertical meridian 811 such that diamagnetic body force $F_B$ [154] generated by the diamagnetic force field $D_B$ in any exemplary biospecimen 153 housed and sustained in vitro by exemplary bioreactor chamber 809a is directed superiorly, and oriented
[i] parallel to vertical meridian 811,
[ii] parallel to long axis 809ax of exemplary bioreactor chamber 809a, and
[iii] antiparallel to force of gravity vector $F_G$ [164]

b. when the diamagnetic force field occupying region 438 (FIG. 6. and FIG. 7) is activated, exemplary bioreactor chamber 809c in exemplary second outer bioreactor holding slot 807c is disposed within region 438 proximal to inferior pole 811i of vertical meridian 811 such that diamagnetic body force $F_B$ [154] generated by the diamagnetic force field $D_B$ in any exemplary biospecimen 153 housed and sustained in vitro by exemplary bioreactor chamber 809c is directed inferiorly, and oriented
[i] parallel to vertical meridian 811,
[ii] parallel to long axis 809cx of exemplary bioreactor chamber 809c, and
[iii] parallel to force of gravity vector $F_G$ [164]

c. when the diamagnetic force field occupying region 438 (FIG. 6. and FIG. 7) is activated, exemplary bioreactor chamber 809b in exemplary central bioreactor holding slot 807b is disposed outside of region 438 where no diamagnetic body force arises in any exemplary biospecimen 153 housed and sustained in vitro by-exemplary bioreactor chamber 809b. Force of gravity vector $F_G$ [164] is parallel to long axis 809bx of exemplary bioreactor chamber 809b.

In FIG. 15, exemplary radially slotted rectilinear insert 800 is shown with exemplary first outer bioreactor chamber holding slot 807a, exemplary central bioreactor chamber holding slot 807b, and exemplary second outer bioreactor chamber holding slot 807c forming a vertical column.

Exemplary radially slotted rectilinear insert 800 may also be secured within rectilinear frame 311 so as to place exemplary first outer bioreactor chamber holding slot 807a, exemplary central bioreactor chamber holding slot 807b, and exemplary second outer bioreactor chamber holding slot 807c, in a horizontal row, by simultaneously rotating exemplary radially slotted rectilinear insert 800 through an angle of 90 degrees about common longitudinal central (y-) axis 437 (FIG. 1) and through an angle of 180 degrees about x-axis 459 (FIG. 1). The second 180-degree rotation is required for proper apposition of insert connecting holes 339i to corresponding frame connecting holes 339f of rectilinear frame 311, into which apposed holes nonmagnetic screws 343 are driven. Only two of the four edges of exemplary radially slotted rectilinear insert 800 connect to rectilinear frame 311 at any time.

In the horizontal orientation of exemplary radially slotted rectilinear insert 800, wherein exemplary bioreactor chambers 809a, 809b, 809c, form a horizontal row disposed along horizontal meridian 810, force of gravity vector $F_G$ [164] is perpendicular to their respective long axes 809ax, 809bx, 809cx; and, in region 438 within which bioreactor chambers 809a and 809c are disposed, diamagnetic body force $F_B$ [154] is still parallel to their respective long axes 809ax and 809cx.

5.48 Exemplary Tangentially Slotted Rectilinear Insert

FIG. 16 is a schematic illustration of an exemplary tangentially slotted rectilinear insert 825 for use with exemplary rectilinear frame 311 shown in FIG. 12. In FIG. 16, exemplary tangentially slotted rectilinear insert 825 is shown without bioreactor chambers, and is seen to have the general form of a thin rectangular parallelepiped, having a superior aspect 801, an inferior aspect 802, a first lateral aspect 803 and a second lateral aspect 804. Exemplary tangentially slotted rectilinear insert 825 may, for example, be made of a square sheet of nonmagnetic material, such as Nylon, Plexiglass® (polymethylmethacrylate), Lexan® polycarbonate resin, or a substantially equivalent material, measuring about 26 cm on a side and having a thickness of about 1 cm.

Imaginary circle 805, having a radius equal to radius R [460] of either first or second circular pole faces 435, 436 of transverse electromagnet 400 (FIG. 2 and FIG. 5) is centered about the geometric center 806 of tangentially slotted rectilinear insert 825. A horizontal line extending between a first lateral pole 810fl at 90 degrees in FIG. 16 and a second lateral pole 810sl at 270 degrees in FIG. 16 represents horizontal meridian 810. A vertical line extending between a superior pole 811s at 180 degrees in FIG. 16 and an inferior pole 811i at zero degrees in FIG. 16 represents vertical meridian 811. The direction of the terrestrial force of gravity is shown in FIG. 16 by gravitational force vector $F_G$ [164].

When exemplary tangentially slotted rectilinear insert 825 is inserted into Rectilinear frame 311 and secured therein, computer-controlled horizontal microstepping motor 350 (FIG. 11) and computer-controlled vertical microstepping motor 360 (FIG. 11.) are activated to initially position tangentially slotted rectilinear insert 825 so that geometric center 806 of imaginary circle 805 is intersected by common longitudinal central (y-)axis of transverse electromagnet 400 and imaginary circle 805 is aligned with first and second circular pole face margins 455 and 456 of first and second circular pole faces 435 and 436 of transverse electromagnet 400 (FIG. 2 and FIG. 5).

Superior aspect 801 and first lateral aspect 803 of exemplary radially slotted rectilinear insert 800 are drilled with a plurality of insert tubing conduits 338i, complementary to and interfacing with frame tubing conduits 338f of rectilinear frame 311, that receive first tubing sets 330, described supra., and shown in FIG. 1. Insert tubing conduits 338i conduct the first tubing sets 330 to exemplary ports 808a, 808b, and 808c of exemplary first outer bioreactor chamber holding slot 807a, exemplary central bioreactor chamber holding slot 807b, and exemplary second outer bioreactor chamber holding slot 807c respectively, cut into exemplary tangentially slotted rectilinear insert 825. Exemplary first outer bioreactor chamber holding slot 807a, exemplary central bioreactor chamber holding slot 807b, and exemplary second outer bioreactor chamber holding slot 807c are full-thickness cut-outs made in tangentially slotted rectilinear insert 825, each having a generally rectangular in form with a length of about 6 cm and a width of about 5 cm.

Opposing full-thickness notches 812n are cut into opposing sides of exemplary first outer bioreactor chamber holding slot 807a, exemplary central bioreactor chamber holding slot 807b, and exemplary second outer bioreactor chamber holding slot 807c, to receive complementary tabs 812t (not shown in FIG. 16) of exemplary bioreactor chamber embodiments forming first set of bioreactor chamber embodiments 500, which tabs are more fully described infra.

FIG. 17 is a schematic illustration of an exemplary tangentially slotted rectilinear insert 825, with exemplary bioreactor chambers, for use with exemplary rectilinear frame 311 shown in FIG. 12. In FIG. 17, exemplary tangentially slotted rectilinear insert 825 of FIG. 16 is shown with three identical exemplary bioreactor chambers 809a, 809b, and 809c having respective long axes 809ax, 809bx, and 809cx. Exemplary bioreactor chambers 809a, 809b and 809c are removably and exchangeably secured in exemplary first outer bioreactor chamber holding slot 807a, exemplary central bioreactor chamber holding slot 807b, and exemplary second outer bioreactor chamber holding slot 807c respectively, by tabs 812t that insert into corresponding notches 812n. Tabs 812t are fashioned at opposing ends of each exemplary bioreactor chamber 809a, 809b and 809c and are intersected by their respective long axes 809ax, 809bx, and 809cx. Tabs 812t are adapted to fit into complementary notches 812n of exemplary first outer bioreactor chamber holding slot 807a, exemplary central bioreactor chamber holding slot 807b, and exemplary second outer bioreactor chamber holding slot 807c of exemplary tangentially slotted rectilinear insert 825.

Notches 812n are cut into opposing sides of exemplary central bioreactor chamber holding slot 807b to orient long axis 809bx of exemplary bioreactor chamber 809b radially with respect to imaginary circle 805 on exemplary tangentially slotted rectilinear insert 825. Notches 812n are cut into opposing sides of exemplary first outer bioreactor chamber holding slot 807a and exemplary second outer bioreactor chamber holding slot 807c so as to orient long axes 809ax and 809cx of exemplary bioreactor chambers 809a and 809c parallel to long axis 809bx of exemplary bioreactor chamber 809b and parallel to a tangent to imaginary circle 805.

The intersection of the plane of exemplary tangentially slotted rectilinear insert 825 with spatial region 438 (FIG. 6A and FIG. 7), within which the diamagnetic force field is generated by transverse electromagnet 400 of first exemplary embodiment of the invention 101, is shown in FIG. 17 as annulus 813 about imaginary circle 805 of radius R [460].

First exemplary outer bioreactor chamber holding slot 807a is cut into tangentially slotted rectilinear insert 825 so as to orient long axis 809ax of exemplary bioreactor chamber 809a, when held therein, parallel to a tangent of a circle having pole radius R (460) and to dispose bioreactor chamber 809a superiorly within region 438 (FIG. 6A and FIG. 7) between first outer radius $R_1$ [461] (FIG. 6A and FIG. 7) of first outer right circular cylinder 441 (FIG. 6A and FIG. 7) and second inner radius $R_2$ [462] (FIG. 6A and FIG. 7) of second inner right circular cylinder 442 (FIG. 6A and FIG. 7).

Second exemplary outer bioreactor chamber holding slot 807c is cut into tangentially slotted rectilinear insert 825 so as to orient long axis 809cx of exemplary bioreactor chamber 809c, when held therein, parallel to a tangent of a circle having pole radius R [460] and to dispose bioreactor chamber 809c inferiorly within region 438 (FIG. 6A and FIG. 7) between first outer radius $R_1$ [461] (FIG. 6A and FIG. 7) of first outer right circular cylinder 441 (FIG. 6A and FIG. 7) and second inner radius $R_2$ [462] (FIG. 6A and FIG. 7) of second inner right circular cylinder 442 (FIG. 6A and FIG. 7).

Exemplary central bioreactor chamber holding slot 807b is cut into tangentially slotted rectilinear insert 825 so as to orient long axis 809bx of exemplary bioreactor chamber 809b, when held therein, perpendicular to pole radius R [460] and to place the geometrical center point (not shown in FIG. 17) of exemplary bioreactor chamber 809b, on central longitudinal (y-) axis 437 of transverse electromagnet 400 (FIG. 6A and FIG. 7).

In FIG. 17, an exemplary first tubing set 330 is represented by dashed dark lines, within insert tubing conduits 338i, communicating with ports 808a of exemplary first outer bioreactor chamber holding slot 807a.

In FIG. 17, exemplary bioreactor chambers 809a, 809b, and 809c are removably and exchangeably secured in exemplary first outer bioreactor chamber holding slot 807a, exemplary central bioreactor chamber holding slot 807b, and exemplary second outer bioreactor chamber holding slot 807c so that:

a. when the diamagnetic force field occupying region 438 (FIG. 6. and FIG. 7) is activated, exemplary bioreactor chamber 809a in exemplary first outer slot 807a is disposed in region 438 proximal to superior pole 811s of vertical meridian 811 such that diamagnetic body force $F_B$ [154] generated by the diamagnetic force-field in any exemplary biospecimen 153 housed and sustained in vitro by exemplary bioreactor chamber 809a is directed superiorly, and oriented

[i] parallel to vertical meridian 811,

[ii] perpendicular to long axis 809ax of exemplary bioreactor chamber 809a, and

[iii] antiparallel to force of gravity vector $F_G$ [164];

b. when the diamagnetic force field occupying region 438 (FIG. 6. and FIG. 7) is activated, exemplary bioreactor chamber 809c in exemplary second outer bioreactor chamber holding slot 807c is disposed within region 438 proximal to inferior pole 811i of vertical meridian 811 such that diamagnetic body force $F_B$ [154] generated by the diamagnetic force field in any exemplary biospecimen 153 housed and sustained in vitro by exemplary bioreactor chamber 809c is directed inferiorly, and oriented

[i] parallel to vertical meridian 811,

[ii] perpendicular to long axis 809cx of exemplary bioreactor chamber 809c, and

[iii] parallel to force of gravity vector $F_G$ [164];

c. when the diamagnetic force field occupying region 438 (FIG. 6. and FIG. 7) is activated, exemplary bioreactor chamber 809b in exemplary central bioreactor chamber holding slot 807b is disposed outside of region 438 and proximal to geometric center 806 where no diamagnetic body force arises in any exemplary biospecimen 153 housed and sustained in vitro by exemplary bioreactor chamber 809b. Force of gravity vector $F_G$ [164] is perpendicular to long axis 809bx of exemplary bioreactor chamber 809b.

A plurality of insert connecting holes, such as exemplary insert connecting hole 339i along two aspects of exemplary tangentially slotted rectilinear insert 825 are adapted to receive corresponding nonmagnetic screws 343, or substantially equivalent fastening devices, enabling exemplary tangentially slotted rectilinear insert 825 to be secured within exemplary rectilinear frame 311 in two alternative orientations—a vertical orientation of bioreactor chamber holding slots and a horizontal orientation of bioreactor chamber holding slots.

In FIG. 17, exemplary tangentially slotted rectilinear insert 825 is shown with exemplary first outer bioreactor chamber holding slot 807a, exemplary central bioreactor chamber holding slot 807b, and exemplary second outer bioreactor chamber holding slot 807c forming a vertical column.

Exemplary tangentially slotted rectilinear insert 825 may be secured within rectilinear frame 311 so as to place exemplary first outer bioreactor chamber holding slot 807a, exemplary central bioreactor chamber holding slot 807b, and exemplary second outer bioreactor chamber holding slot 807c, in a horizontal orientation wherein they form a horizontal row, by simultaneously rotating exemplary tangentially slotted rectilinear insert 825 through an angle of 90 degrees about common longitudinal central (y-) axis 437 (FIG. 2), and through an angle of 180 degrees about x-axis 459 (FIG. 2). The second 180-degree rotation is required for proper apposition of insert connecting holes 339i to corresponding frame connecting holes 339f of rectilinear frame 311, into which apposed holes nonmagnetic-screws 343 (not shown in FIG. 17) are driven. Only two of the four aspects of exemplary radially slotted rectilinear insert 800 connect to rectilinear frame 311 at any time.

In the horizontal orientation of exemplary tangentially slotted rectilinear insert 825, wherein exemplary bioreactor chambers 809a, 809b, 809c, form a horizontal row disposed along horizontal meridian 810, force of gravity vector $F_G$ [164] is parallel to their respective long axes 809ax, 809bx, 809cx; and, in region 438 within which bioreactor chambers 809a and 809c are disposed, diamagnetic body force $F_B$ (154) is still perpendicular to respective long axes 809ax and 809cx.

As indicated supra., exemplary circular frame 370 supports either an exemplary radially slotted circular insert 850 or an exemplary tangentially slotted circular insert 875.

5.49 Exemplary Radially Slotted Circular Insert

FIG. 18 shows an exemplary radially slotted circular insert 850 with two exemplary bioreactor chambers 809a and 809b respectively secured in exemplary first outer bioreactor chamber holding slot 807a and exemplary central bioreactor holding slot 807b. Exemplary radially slotted circular insert 850 is in the shape of a circle and is made of a nonmagnetic material, such as, for example, Nylon, Plexiglass® (polymethylmethacrylate), Lexan® polycarbonate resin, or a substantially equivalent material, measuring about 26 cm in diameter and having a thickness of about 1 cm.

Exemplary radially slotted circular insert 850 is rotatably disposable in circular opening 378 of nonmagnetic circular frame 370 (FIG. 13), resting inferiorly in annular track 375 of linear inferior member 372 of nonmagnetic circular frame 370 (FIG. 13), and secured in an angular orientation with respect to exemplary protractor scale 380 (FIG. 13) by positioning screw 379 (FIG. 13.) or substantially equivalent means for rotatably fastening exemplary radially slotted circular insert 850 in annular track 375 (FIG. 13) of linear inferior member 372 (FIG. 13).

In FIG. 18 imaginary circle 805, having a radius equal to radius R [460] of either first or second circular pole faces 435, 436 of transverse electromagnet 400 (FIG. 2 and FIG. 5), is centered about the geometric center 806 of exemplary radially slotted circular insert 850. A horizontal line extending between a first lateral pole 810fl at 90 degrees in FIG. 18 and a second lateral pole 810sl at 270 degrees in FIG. 18 represents horizontal meridian 810. A vertical line extending between a superior pole 811s at 180 degrees in FIG. 18 and an inferior pole 811i at zero degrees in FIG. 18 represents vertical meridian 811.

When exemplary radially slotted circular insert 850 is inserted into nonmagnetic circular frame 370 (FIG. 13) and secured therein, computer-controlled horizontal microstepping motor 350 (FIG. 11) and computer-controlled vertical stepping motor 360 (FIG. 11) are activated to initially position exemplary radially slotted circular insert 850 so that the geometric center 806 of imaginary circle 805 is intersected by common longitudinal central (y-)axis 437 (FIG. 6A and FIG. 7) of transverse electromagnet 400 and the perimeter of imaginary circle 805 is aligned with first and second circular pole face margins 455 and 456 of first and second circular pole faces 435 and 436 of transverse electromagnet 400 (FIG. 2 and FIG. 5). The direction of the terrestrial force of gravity is shown in FIG. 18 by gravitational force vector $F_G$ [164].

Circular edge 826 of exemplary radially slotted circular insert 850 is drilled with a plurality of insert tubing conduits 338i, complementary to and interfacing with frame tubing conduits 338f of nonmagnetic circular frame 370, which receive first tubing sets 330, described supra. Insert tubing conduits 338i conduct the first tubing sets 330 to exemplary ports 808a and 808b of exemplary first outer bioreactor chamber holding slot 807a and exemplary central bioreactor chamber holding slot 807b respectively, cut into exemplary radially slotted circular insert 850.

Exemplary first outer bioreactor chamber holding slot 807a and exemplary central bioreactor holding slot 807b are full-thickness cutouts made in exemplary radially slotted circular insert 850, each having a generally rectangular form with a {length of about 5-7 cm and a width of about 5 cm. A longer length is required for central bioreactor holding slot 807b to allow for tubes carried by insert tubing conduits 338i to remain straight as they extend inward from circular edge 826.

In FIG. 18, exemplary radially slotted circular insert 850 is shown with two identical exemplary bioreactor chambers 809a and 809b having respective long axes 809ax and 809bx. Exemplary bioreactor chambers 809a and 809b are removably and exchangeably secured in exemplary first outer bioreactor chamber holding slot 807a and exemplary central bioreactor chamber holding slot 807b respectively by tabs 812t that insert into corresponding notches 812n. Tabs 812t are fashioned at opposing ends of each exemplary bioreactor chamber 809a and 809b and are intersected by their respective long axes 809ax and 809bx. Tabs 812t are adapted to fit into complementary notches 812n of exemplary first outer bioreactor chamber holding slot 807a and exemplary central bioreactor chamber holding slot 807b of exemplary radially slotted circular insert 850.

Notches 812n are cut into sides of exemplary first outer bioreactor chamber holding slot 807a and exemplary central bioreactor chamber holding slot 807b so as to orient long axes 809ax and 809bx of exemplary bioreactor chambers 809a and 809b radially aligned with pole radius R [460] of imaginary circle 805 on exemplary radially slotted circular insert 850.

First exemplary outer bioreactor chamber holding slot 807a is cut into radially slotted circular insert 850 so as to orient long axis 809ax of exemplary bioreactor chamber 809a, when held therein, radially aligned with pole radius R [460] and to dispose bioreactor chamber 809a within region 438 (FIG. 6A and FIG. 7) between first outer radius $R_1$ (461) (FIG. 6A and FIG. 7) of first outer right circular cylinder 441 (FIG. 6A and FIG. 7) and second inner radius $R_2$ (462) (FIG. 6A and FIG. 7) of second inner right circular cylinder 442 (FIG. 6A and FIG. 7). Exemplary central bioreactor chamber holding slot 807b is cut into radially slotted circular insert 850 so as to orient long axis 809bx of exemplary bioreactor chamber 809b, when held therein, radially aligned with pole radius R [460] and to place the geometrical center point (not shown in FIG. 18) of exemplary bioreactor chamber 809b on central longitudinal (y-) axis 437 (FIG. 6A and FIG. 7) of transverse electromagnet 400.

An exemplary first tubing set 330 is represented by dashed dark lines, within tubing conduits 338i, communicating with port 808b of exemplary bioreactor chamber holding slot 807b.

The intersection of the plane of exemplary radially slotted circular insert 850 with spatial region 438 (FIG. 6A and FIG. 7), within which the diamagnetic force field is generated-by transverse electromagnet 400 of first exemplary embodiment of the invention 101, is shown in FIG. 18 as annulus 813 about imaginary circle 805 of pole radius R [460].

In FIG. 18, exemplary bioreactor chambers 809a and 809b are removably and exchangeably secured in exemplary first outer bioreactor chamber holding slot 807a and exemplary central bioreactor chamber holding slot 807b respectively so that:

a. when the diamagnetic force field occupying region 438 (FIG. 6 and FIG. 7) is activated, exemplary bioreactor chamber 809a in exemplary first outer bioreactor chamber holding slot 807a may be disposed along meridians other than the horizontal (90-270 degree) meridian 810 or the vertical (zero-180 degree) meridian 811, such as, for example, meridians at about 45 degrees or at about 135 degrees. At these exemplary orientations, exemplary bioreactor chamber 809a in exemplary first outer bioreactor chamber holding slot 807a will be disposed in region 438 (FIG. 6 and FIG. 7) such that diamagnetic body force $F_B$ [154] generated by the diamagnetic force field in any exemplary biospecimen 153 housed and sustained in vitro by exemplary bioreactor chamber 809a is directed radially outward from geometric center 806, and oriented parallel to long axis 809ax of exemplary bioreactor chamber 809a. Moreover when oriented along meridians other than the horizontal (90-270 degree) meridian 810 or the vertical (zero-180 degree) meridian 811, only the vertical component of diamagnetic body force $F_B$ [154] generated by the diamagnetic force field in any exemplary biospecimen 153 interacts with gravitational force vector $F_G$ [164].

b. When the diamagnetic force field occupying region 438 (FIG. 6. and FIG. 7) is activated, exemplary bioreactor chamber 809b in exemplary central bioreactor chamber holding slot 807b is disposed outside of region 438 and proximal to geometric center 806 where no diamagnetic body force arises in any exemplary biospecimen 153 housed and sustained in vitro by exemplary bioreactor chamber 809b.

5.50 Exemplary Tangentially Slotted Circular Insert

FIG. 19 shows an exemplary tangentially slotted circular insert 875 with two exemplary bioreactor chambers 809a and 809b respectively secured in exemplary first outer bioreactor chamber holding slot 807a and exemplary central bioreactor chamber holding slot 807b. Exemplary tangentially slotted circular insert 875 is in the shape of a circle and is made of a nonmagnetic material, such as, for example, Nylon, Plexiglass® (polymethylmethacrylate), Lexan® polycarbonate resin or a substantially equivalent material, measuring about 26 cm in diameter and having a thickness of about 1 cm.

Exemplary tangentially slotted circular insert 875 is rotatably disposed in circular opening 378 of nonmagnetic circular frame 370 (FIG. 13) resting inferiorly in annular track 375 (FIG. 13) of linear inferior member 372 (FIG. 13) of nonmagnetic circular frame 370 (FIG. 13), and secured in an angular orientation with respect to exemplary protractor scale 380 (FIG. 13) by positioning screw 379 (FIG. 13).

In FIG. 19, imaginary circle 805, having a radius equal to radius R [460] of either first or second circular pole faces 435, 436 of transverse electromagnet 400 (FIG. 2 and FIG. 5) is centered about the geometric center 806 of exemplary tangentially slotted circular insert 875. A horizontal line extending between a first lateral pole 810fl at 90 degrees in FIG. 19 and a second lateral pole 810sl at 270 degrees in FIG. 19 represents horizontal meridian 810. A vertical line extending between a superior pole 811s at 180 degrees in FIG. 19 and an inferior pole 811i at zero degrees in FIG. 19 represents vertical meridian 811.

When exemplary tangentially slotted circular insert 875 is inserted into nonmagnetic circular frame 370 (FIG. 13) and secured therein, computer-controlled horizontal microstepping motor 350 (FIG. 11) and computer-controlled vertical microstepping motor 360 (FIG. 11) are activated to initially position exemplary tangentially slotted circular insert 875 so that the geometric center 806 of imaginary circle 805 is intersected by common longitudinal central (y-) axis 437 (FIG. 6A and FIG. 7) of transverse electromagnet 400 and the perimeter of imaginary circle 805 is aligned with first and second circular pole face margins 455 and 456 of first and second circular pole faces 435 and 436 of transverse electromagnet 400 (FIG. 2 and FIG. 5). The direction of the terrestrial force of gravity is shown in FIG. 19 by gravitational force vector $F_G$ [164].

Circular edge 826 of exemplary tangentially slotted circular insert 875 is drilled with a plurality of insert tubing conduits 338i, complementary to and interfacing with frame tubing conduits 338f of nonmagnetic circular frame 370 (FIG. 13), that receive first tubing sets 330, described supra. Insert tubing conduits 338i conduct first tubing sets 330 to exemplary ports 808a and 808b of exemplary first outer bioreactor chamber holding slot 807a and exemplary central bioreactor chamber holding slot 807b respectively, cut into exemplary tangentially slotted circular insert 875. Exemplary first outer bioreactor chamber holding slot 807a and exemplary central bioreactor chamber holding slot 807b are full-thickness cut-outs made in exemplary tangentially slotted circular insert 875, each having a generally rectangular form with a width of about 5 cm and a length of about 5 cm.

In FIG. 19, exemplary tangentially slotted circular insert 875 is shown with two identical exemplary bioreactor chambers 809a and 809b having respective long axes 809ax and 809bx. Exemplary bioreactor chambers 809a and 809b are removably and exchangeably secured in exemplary first outer bioreactor chamber holding slot 807a and exemplary central bioreactor holding slot 807b respectively by tabs 812t that insert into corresponding notches 812n. Tabs 812t are fashioned at opposing ends of exemplary first outer bioreactor chamber holding slot 807a and exemplary central bioreactor chamber holding slot 807b, and are intersected by their respective long axes 809ax and 809bx. Tabs 812t are adapted to fit into complementary notches 812n of exemplary first outer bioreactor chamber holding slot 807a and exemplary central bioreactor chamber holding slot 807b of exemplary tangentially slotted circular insert 875.

Notches 812n are cut into sides of exemplary first outer bioreactor chamber holding slot 807a so as to orient long axis 809ax of exemplary first outer bioreactor chambers 809a perpendicular to pole radius R [460] and parallel to a tangent of imaginary circle 805 on exemplary tangentially slotted circular insert 875. Notches 812n are cut into sides of exemplary central bioreactor chamber holding slot 807b so as to orient long axis 809bx of exemplary central bioreactor chamber 809b parallel to long axis 809ax.

First exemplary outer bioreactor chamber holding slot 807a is cut into tangentially slotted circular insert 875 so as to orient long axis 809ax of exemplary bioreactor chamber 809a, when held therein, perpendicular to pole radius R [460] and parallel to a tangent to a circle having pole radius R [460], and to dispose bioreactor chamber 809a within region of space 438 (FIG. 6A and FIG. 7) between first outer radius $R_1$ [461] (FIG. 6A and FIG. 7) of first outer right circular cylinder 441 (FIG. 6A and FIG. 7) and second inner radius $R_2$ [462] (FIG. 6A and FIG. 7) of second inner right circular cylinder 442 (FIG. 6A and FIG. 7).

Exemplary central bioreactor chamber holding slot 807b is cut into tangentially slotted circular insert 875 so as to orient long axis 809bx of exemplary bioreactor chamber 809b, when held therein, perpendicular to pole radius R [460] and parallel to long axis 809ax, and to place the geometrical center point (not shown) of exemplary bioreactor chamber 809b on central longitudinal (y-) axis . 437 (FIG. 6A and FIG. 7) of transverse electromagnet 400.

An exemplary first tubing set 330 is represented by dashed dark lines, within insert tubing conduits 338i, communicating with ports 808a of exemplary first outer bioreactor chamber holding slot 807a.

The intersection of the plane of exemplary tangentially slotted circular insert 875 with spatial region 438 (FIG. 6A and FIG. 7), within which the diamagnetic force field is generated by transverse electromagnet 400 of first exemplary embodiment of the invention 100, is shown in FIG. 19 as annulus 813 about imaginary circle 805 of radius R [460].

In FIG. 19, exemplary bioreactor chambers 809a and 809b are removably and exchangeably secured in exemplary first outer bioreactor chamber holding slot 807a and exemplary central bioreactor chamber holding slot 807b respectively so that:

a. when the diamagnetic force field occupying region 438 (FIG. 6 and FIG. 7) is activated, exemplary bioreactor chamber 809a in exemplary first outer bioreactor chamber holding slot 807a may be disposed along meridians other than the horizontal (90-270 degree) meridian 810 or the vertical (zero-180 degree) meridian 811, such as, for example, meridians at about 45 degrees or at about 135 degrees. At these exemplary orientations, exemplary bioreactor chamber 809a in exemplary first outer slot 807a will be disposed in region 438 (FIG. 6 and FIG. 7) such that diamagnetic body force $F_B$ [154] generated by the diamagnetic force field in any exemplary biospecimen 153 housed and sustained in vitro by exemplary bioreactor chamber 809a is directed radially outward from geometric center 806, and oriented perpendicularly to long axis 809ax of exemplary bioreactor chamber 809a. Moreover, when oriented along meridians other than the horizontal (90-270 degree) meridian 810 or the vertical (zero-180 degree) meridian 811, only the vertical component of diamagnetic body force $F_B$ [154] generated by the diamagnetic force field $D_B$ in any exemplary biospecimen 153 interacts with gravitational force vector $F_G$ [164].

b when the diamagnetic force field occupying region of space 438 (FIG. 6 and FIG. 7) is activated, exemplary bioreactor chamber 809b in exemplary central bioreactor chamber holding slot 807b is disposed outside of region 438 and proximal to geometric center 806 where no diamagnetic body force arises in any exemplary biospecimen 153 housed and sustained in vitro by exemplary bioreactor chamber 809b.

The foregoing discussion in connection with FIG. 18 and FIG. 19 demonstrates that a vector corresponding to a direction of diamagnetic body force $F_B$ [154] may form an angle having any value between about zero degrees and about one-hundred and eighty degrees with respect to a vector corresponding to a direction of a secondary body force acting upon or arising within biospecimen 153, such as, for example, gravitational force $F_G$ [164].

5.51 Common Body of First Set of Bioreactor Embodiments

Exemplary common body 511 is made of a nonmagnetic, water-impermeable material, such as, for example, Nylon, Plexiglass® (polymethylmethacrylate), Lexan® polycarbonate resin, or a substantially equivalent material, and is secured by tabs 812t that removably insert into opposing full-thickness notches 812n (not shown in FIG. 20A) in exemplary first outer bioreactor chamber holding slot 807a, exemplary central bioreactor chamber holding slot 807b, and exemplary second outer bioreactor chamber holding slot 807c, cut into either:

[i] radially slotted rectilinear insert 800 (FIG. 14); or,
[ii] tangentially slotted rectilinear insert 825 (FIG. 16) for rectilinear frame 311 (FIG. 12); or,
[iii] radially slotted circular insert 850 (FIG. 18); or,
[iv] tangentially slotted circular insert 875 (FIG. 19) for nonmagnetic circular frame 370 (FIG. 13), all described supra.

As shown in FIG. 20A, the cross section of exemplary common body 511 is in the general form of a rectangle with walls having a thickness of about 5 mm. Exemplary common body 511 has a length of about 60 mm, a height of about 30 mm and a depth of about 20 mm. Exemplary common body 511 has parallel opposing first and second short walls of equal height and thickness 502S1 and 502S2, and two pairs of parallel opposing long double-layered walls of equal length and thickness, of which one set, 503L1 and 503L2, is shown in FIG. 20A in cross section. Each long wall, 503L1 and 503L2 (and the two remaining long walls not shown in FIG. 20A) is double-layered, having an inner wall 504i and an outer wall 504o, whose ends have apposing thickened steps 508 that create a slot-like space 507 between inner wall 504i and outer wall 504i.

The two pairs of parallel opposing long double-layered walls of exemplary common body 511 (of which one set, 503L1 and 503L2, is shown in FIG. 20A), are joined to one another and to short wall 502S2 in a water-tight fashion by suitable adhesives, well known in the arts. Alternatively, the two pairs of parallel opposing long double-layered walls of exemplary common body 511 (of which one set, 503L1 and 503L2, is shown in FIG. 20A) may be fabricated as one piece. Opposing short wall 502S1 also comprises a removable water-tight cap 505.

Cap 505 closes exemplary common body 511 to form a rectangular parallelepiped about interior volume 501 with slot-like space 507 within each long wall forming a contiguous four-sided rectangular water-tight jacket 509 enveloping water-tight interior volume 501 of exemplary common body 511.

The water-tight interior volume 501 of exemplary common body 511 is accessed by cap 505. Removable water-tight cap 505 may be secured to exemplary common body 511 by nonmagnetic cap screws 506, or substantially equivalent devices, that secure removable water-tight cap 505 to the apposing edges of the long walls of exemplary common body 511. Nonmagnetic cap screws 506 may be made of a non-magnetic water-impermeable material, such as, for example, Nylon, Plexiglass® (polymethylmethacrylate), Lexan® polycarbonate resin, or a substantially equivalent material. Accordingly, removable water-tight cap 505 forms a water-tight door for access to water-tight interior volume 501 of exemplary common body 511.

Short walls 502S1 and 502S2 bear opposing parallel tabs 812t for insertion into corresponding opposing parallel notches 812n (not shown in FIG. 20A) fashioned into holding slots 807 of inserts 800, 825, 850 and 875, described supra.

Exemplary common body 511 receives exemplary first afferent tube bundle 333 and exemplary first efferent tube bundle 334, carried to it by either exemplary first outer bioreactor chamber holding slot 807a, exemplary central bioreactor chamber holding slot 807b, and exemplary second outer bioreactor chamber holding slot 807c, cut into either:
[i] radially slotted rectilinear insert 800 (FIG. 14); or,
[ii] tangentially slotted rectilinear insert 825 (FIG. 16) of rectilinear frame 311 (FIG. 12); or,
[iii] radially slotted circular insert 850 (FIG. 18); or,
[iv] tangentially slotted circular insert 875 (FIG. 19) of nonmagnetic circular frame 370 (FIG. 13), by near-contiguously communicating frame tubing conduits 338 f and insert conduits 338i, (FIG. 14 through FIG. 19) described supra.

In FIG. 20A, water-tight jacket 509 enveloping water-tight interior 501 of exemplary common body 511 is seen to have afferent temperature port 516t and efferent temperature port 517t. Afferent temperature port 516t receives first afferent temperature tube 333t of first afferent tube bundle 333 of first set of tubes 330 (FIG. 1) and efferent temperature port 517t receives first efferent temperature tube 334t of first efferent tube bundle 334 of first set of tubes 330 (FIG. 1). Afferent temperature port 516t and efferent temperature port 517t, thereby complete a fluid circulation loop between water-tight jacket 509 and temperature control subsystem 240 of biological in vitro support system 200 (FIG. 1)

Water-tight interior 501 of exemplary common body 511 has three general purpose ports 518a, 518b, and 518c for venting gas and/or detachably and exchangeably connecting, in appropriate combinations that depend on the desired in vitro environment, first afferent gas tube 333g, first afferent perfusion tube 333p, and first efferent perfusion tube 334p. Any general purpose port may also be used for sampling fluid provided to water tight interior 501 by biological in vitro support system 200 (FIG. 1).

FIG. 20A1 is a less detailed schematic cross-sectional view of exemplary common body 511, in which opposing interior surfaces of inner wall 504i of parallel opposing long double-layered walls 503L1 and 503L2 of common body 511 have been formed into a plurality of parallel and opposing inwardly projecting ledges 513 for the carriage of biospecimens 153 mounted on a plurality of slides (not shown in FIG. 20A1).

FIG. 20A2 is also a less detailed schematic cross-sectional view of exemplary common body 511, along line 20-20 of FIG. 20A1, showing inwardly projecting ledges 513 on end.

5.52 Tangential Two-dimensional Static Bioreactor Chamber

FIG. 20B is a schematic cross-sectional view of the exemplary common body of FIG. 20A1 and FIG. 20A2 adapted to form an exemplary tangential 2-D static bioreactor chamber 520, wherein an exemplary three parallel inwardly projecting ledges 513 carry three exemplary slides 512a, 512b, and 512c, or substantially equivalent surfaces, each bearing an exemplary biospecimens 153. Biospecimens 153 may vary from slide to slide.

Exemplary tangential 2-D static bioreactor chamber 520 orients the planes of exemplary biospecimens 153 on exemplary slides 512a, 512b, and 512c borne by ledges 513 so that they perpendicular to pole radius R [460] and parallel to tangent lines to concentric circles of radius $R_1$ [461] and $R_2$ [462] shown in FIG. 6A, and FIG. 7, when exemplary tangential 2-D static bioreactor chamber 520 is held in slots of exemplary tangentially slotted rectilinear insert 825 (FIG. 16) or exemplary tangentially slotted circular insert 875 (FIG. 19)

5.53 Radial Two-dimensional Static Bioreactor Chamber

FIG. 20C is a schematic cross-sectional view of the exemplary common body 511 of FIG. 20A1 and FIG. 20A2 adapted to form an exemplary radial 2-D static bioreactor chamber 530, wherein exemplary three parallel inwardly projecting ledges 513 carry three exemplary slides 512a, 512b, and 512c, or substantially equivalent surfaces, each bearing an exemplary biospecimens 153. Biospecimens 153 may vary from slide to slide.

Exemplary radial 2-D static bioreactor chamber 530 orients the planes of exemplary biospecimens 153 on exemplary slides 512a, 512b, and 512c borne by ledges 513 so that they are radially aligned with pole radius R [460] and perpendicularly intersect tangent lines to concentric circles of radius $R_1$ [461] and $R_2$ [462] shown in FIG. 6A, and FIG. 7, when exemplary radial 2-D static bioreactor chamber 530 is held in slots of exemplary radially slotted rectilinear insert 800 (FIG. 14) or exemplary radially slotted circular insert 850 (FIG. 18).

Accordingly exemplary tangential 2-D static bioreactor chamber 520 and exemplary radial 2-D static bioreactor chamber 530 are variants of one another that differ only in the manner in which they orient the planes of the biospecimens they house with respect to the concentric circles of radius R [460], $R_1$ [461] and $R_2$ [462] shown in FIG. FIG. 6A and FIG. 7.

5.54 Vector Orientations of $F_G$, $F_B$, $P_F$ for Tangential 2-D Static Bioreactor Chamber Held in either Tangentially Slotted Rectilinear Insert or Tangentially Slotted Circular Insert as a Vertical Column Ledges 513 in are spaced apart from one another such that when exemplary tangential 2-D static bioreactor chamber 520 (FIG. 20B) is lodged within [i] exemplary first outer bioreactor chamber holding slot 807*a* or [ii] exemplary second outer bioreactor chamber holding slot 807*c* of exemplary tangentially slotted rectilinear insert 825 (FIG. 17) so as to form a vertical column of bioreactor chambers (FIGS. 16, 17); or, [iii] exemplary outer bioreactor chamber holding slot 807*a* of exemplary tangentially slotted circular insert 875 (FIG. 19), biospecimens 153 will be borne on slides 512*a*, 512*b*, 512*c* carried by ledges 513 in planes that will be perpendicular to pole radius R [460] (FIG. 6A) of transverse electromagnet 400 and will be disposed within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be perpendicular to the planes of exemplary slides 512*a*, 512*b*, 512*c*, and diamagnetic body force $F_B$ [154] (FIG. 17) will also be perpendicular to the planes of exemplary slides 512*a*, 512*b*, 512*c*.

When exemplary tangential 2-D static bioreactor chamber 520 is slotted in tangentially slotted rectilinear insert 825 to form a vertical column of bioreactor chambers, described supra. general port 518*b* receives first afferent gas tube 333*g* (not shown in FIG. 20B), general port 518*c* vents gas to the environment, and general port 518*a* is closed.

5.55 Vector Orientations of $F_G$, $F_B$, $P_F$ for Tangential 2-D Static Bioreactor Chamber Held in either Tangentially Slotted Rectilinear Insert or Tangentially Slotted Circular Insert as a Horizontal Row When exemplary tangential 2-D static bioreactor chamber 520 (FIG. 20B) is lodged within [i] exemplary first outer bioreactor chamber holding slot 807*a* or [ii] exemplary second outer bioreactor chamber holding slot 807*c* of exemplary tangentially slotted rectilinear insert 825 (FIG. 17) so as to form a horizontal row, described, supra., biospecimens 153 will be borne on slides 512*a*, 512*b*, 512*c* carried by ledges 513 in planes that will be perpendicular to pole radius R [460] (FIG. 6A) of transverse electromagnet 400 and will still be disposed within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, however, force of gravity vector $F_G$ [164] (FIG. 17) will be parallel to the planes of exemplary slides 512*a*, 512*b*, 512*c*, while diamagnetic body force $F_B$ [154] (FIG. 17) will remain perpendicular to the planes of exemplary slides 512*a*, 512*b*, 512*c*.

When exemplary tangential 2-D static bioreactor chamber 520 is slotted in tangentially slotted rectilinear insert 825 to form a horizontal row, general port 518*b* receives first afferent gas tube 333*g* (not shown in FIG. 20B), general port 518*a* vents gas to the environment, and general port 518*c* is closed.

Biospecimens 153 are sustained in vitro in a static culture medium with no perfusate flowing through exemplary 2-D static flow bioreactor chamber 520.

5.56 Vector Orientations of $F_G$, $F_B$, $P_F$ for Radial 2-D Static Bioreactor Chamber Held in either Radially Slotted Rectilinear Insert or Radially Slotted Circular Insert as a Vertical Column Ledges 513 are spaced apart from one another such that when exemplary radial 2-D static bioreactor chamber 530 (FIG. 20C) is lodged within [i] exemplary first outer bioreactor chamber holding slot 807*a* or [ii] exemplary second outer bioreactor chamber holding slot 807*c* of exemplary radially slotted rectilinear insert 800 (FIGS. 14, 15) so as to form a vertical column of bioreactor chambers; or, [iii] exemplary outer bioreactor chamber holding slot 807*a* of exemplary radially slotted circular insert 850 (FIG. 18), biospecimens 153 will be borne on slides 512*a*, 512*b*, 512*c* carried by ledges 513 in planes that will be aligned with pole radius R [460] of transverse electromagnet 400 (FIG. 6A) and will perpendicularly intersect a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be parallel to the planes of slides 512*a*, 512*b*, 512*c*, and diamagnetic body force $F_B$ [154] (FIG. 17) will also be parallel to the planes of exemplary slides 512*a*, 512*b*, 512*c*.

When exemplary radial 2-D static bioreactor chamber 530 (FIG. 20C) is slotted in radially slotted rectilinear insert 800 to form a vertical column of bioreactor chambers, described supra., general port 518*b* receives first afferent gas tube 333*g* (not shown in FIG. 20C), general port 518*c* vents gas to the environment, and general port 518*a* is closed.

5.57 Vector Orientations of $F_G$, $F_B$, $P_F$ for Radial 2-D Static Bioreactor Chamber Held in either Radially Slotted Rectilinear Insert or Radially Slotted Circular Insert as a Horizontal Row When exemplary radial 2-D static bioreactor chamber 530 is lodged within [i] exemplary first outer bioreactor chamber holding slot 807*a* or [ii] exemplary second outer bioreactor chamber holding slot 807*c* of exemplary radially slotted rectilinear insert 800 (FIGS. 14, 15) so as to form a horizontal row of bioreactor chambers; or, [iii] exemplary outer bioreactor chamber holding slot 807*a* of exemplary radially slotted circular insert 850 (FIG. 18), biospecimens 153 will be borne on slides 512*a*, 512*b*, 512*c* carried by ledges 513 in planes that will be aligned with pole radius R [460] (FIG. 6A) of transverse electromagnet 400 and will be disposed within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, however, force of gravity vector $F_G$ [164] (FIG. 17) will be perpendicular to the planes of slides 512*a*, 512*b*, 512*c*, while diamagnetic body force $F_B$ [154] (FIG. 17) will remain parallel to the planes of exemplary slides 512*a*, 512*b*, and 512*c*.

When exemplary radial 2-D static bioreactor chamber 530 is slotted in radially slotted rectilinear insert 800 to form a horizontal row, general port 518*b* receives first afferent gas tube 333*g* (not shown in FIG. 20C), general port 518*a* vents gas to the environment, and general port 518*c* is closed.

Biospecimens 153 are sustained in vitro in a static culture medium with no perfusate flowing through exemplary radial 2-D static flow bioreactor chamber 530.

FIG. 20D, FIG. 20D1 and FIG. 20D2 are views of a flow insert 551 used to modify the internal volume 501 of common body 511 shown in FIG. 20A.

FIG. 20D is a perspective schematic view of flow insert 551. Flow insert 551 is a tiered structure made of a nonmagnetic, water-impermeable material, such as, for example, Nylon, Plexiglass® (polymethylmethacrylate), Lexan® polycarbonate resin, or a substantially equivalent material.

Flow insert 551 is comprised of an L-shaped frame 551F having a base member 551B perpendicular to a supporting wall 551W, from which supporting wall 551W a first flow divider 551A and a second flow divider 551C, both in the general form of rectangular parallelepipeds, project in planes that are parallel to the plane of base member 551B.

Base member 551B and flow dividers 551A and 551C may be joined to supporting wall 551W by suitable adhesives, well known in the arts, or flow insert 551 by may fabricated into the same solid geometry as a single component by injection molding or a substantially equivalent method.

Base member 551B has a recess 551BR for receiving an exemplary biospecimen (not shown in FIG. 20D) with or without a slide (not shown FIG. 20D). First flow divider 551A also has a recess 551AR for receiving another exemplary biospecimen (not shown in FIG. 20D) with or without a slide (not shown in FIG. 20D).

When flow insert 551 is placed within internal volume 501 of common body 511 (FIG. 20A), supporting wall 551W of flow insert 551 is fitted against an interior surface of an inner wall of a long double-layered wall of common body 511. First flow divider 551A and a second flow divider 551C are both shorter in length than base member 551B, and are joined to or extruded from supporting wall 551W so as to leave symmetrically opposing columns of space 501a and 501b for the ingress and egress of a perfusate, such as, for example, serum, plasma, physiological saline or another solution of electrolytes, into interior volume 501 of common body 511 (FIG. 20A) to occupy the spaces not occupied by flow insert 551.

In FIG. 20E, and FIG. 20F, symmetrically opposing columns of space 501a and 501b are shown as respectively underlying general port 518a and general port 518b of common body 511 of the bioreactor chambers respectively illustrated in these figures. FIG. 20F has a bidirectional arrow immediately beneath general port 518a and general port 518b indicative of alternative flow directions of a perfusate.

Accordingly, an exemplary 2-D flow bioreactor chamber is created when flow insert 551 is placed in interior volume 501 of common body 511 (FIG. 20A).

FIG. 20E shows a cross-sectional view of an exemplary 2-D normal-flow bioreactor chamber 540 and FIG. 20F shows a cross-sectional view of an exemplary 2-D parallel-flow bioreactor chamber 550.

In FIG. 20E and FIG. 20F, supporting wall 551W of flow insert 551 is fitted against an interior surface of inner wall 504i of a long wall of common body 511, that is perpendicular to long wall 503L1 or long wall 503L2 (and hence not shown in FIG. 20E and FIG. 20F). In FIG. 20E and FIG. 20F, base member 551B of flow insert 551 carries an exemplary biospecimen 153b within recess 551BR and first flow divider 551A of flow insert 551 carries another exemplary biospecimen 153a within recess 551AR.

Second flow divider 551C of flow insert 551, together with first flow divider 551A and base member 551B define symmetrically opposing columns of space 501a and 501b, respectively underlying general port 518a and general port 518b.

5.58 Two-dimensional Normal-flow Bioreactor Chamber

In FIG. 20E, general port 518a of exemplary 2-D normal-flow bioreactor chamber 540 receives first afferent perfusion tube 333p (not shown in FIG. 20E). First flow divider 551A and base member 551B direct the perfusate to flow over exemplary biospecimen 153b. Second flow divider 551C and first flow divider 551A direct the perfusate to flow over exemplary biospecimen 153a. The perfusate leaves exemplary 2-D normal-flow bioreactor chamber 540 through general purpose port 518b connected to first afferent perfusion tube 334p (not shown in FIG. 20E), thereby forming a closed perfusion circuit with perfusion control subsystem 250 of biological in vitro support system 200 (FIG. 1). General port 518c is closed.

5.59 Vector Orientations of $F_G$, $F_B$, $P_F$ for 2-D Normal-flow Bioreactor Chamber Held in either Tangentially Slotted Rectilinear Insert or Tangentially Slotted Circular Insert as a Vertical Column Exemplary 2-D normal-flow bioreactor chamber 540 (FIG. 20E) is the flow analogue of exemplary tangential 2-D static bioreactor chamber 520 (FIG. 20B). In FIG. 20E, biospecimens 153a and 153b are spaced apart from one another such that when exemplary 2-D normal-flow bioreactor chamber 540 is lodged within [i] exemplary first outer bioreactor chamber holding slot 807a or [ii] exemplary second outer bioreactor chamber holding slot 807c of exemplary tangentially slotted rectilinear insert 825 (FIG. 17) so as to form a vertical column (FIG. 17); or, [iii] exemplary outer bioreactor chamber holding slot 807a of exemplary tangentially slotted circular insert 875 (FIG. 19), biospecimens 153a and 153b will be respectively carried by first flow divider 551A and base member 551B in planes that are perpendicular to pole radius R [460] (FIG. 6A) of transverse electromagnet 400 and will be disposed within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 20E) will be perpendicular to the planes of biospecimens 153a and 153b, diamagnetic body force $F_B$ [154] (FIG. 20E) will also be perpendicular to the planes of biospecimens 153a and 153b.

Flow insert 551 will cause the perfusate to flow tangentially across the surfaces of biospecimens 153a and 153b in a manner that maintains the direction of a flow vector $P_F$ [190] (FIG. 20E) of the perfusate normal (perpendicular) to the direction of the diamagnetic body force $F_B$ [154] induced in biospecimens 153a and 153b.

5.60 Vector Orientations of $F_G$, $F_B$, $P_F$ for 2-D Normal-flow Bioreactor Chamber Held in either Tangentially Slotted Rectilinear Insert or Tangentially Slotted Circular Insert as a Horizontal Row When exemplary 2-D normal-flow bioreactor chamber 540 is lodged within [i] exemplary first outer bioreactor chamber holding slot 807a or [ii] exemplary second outer bioreactor chamber holding slot 807c of exemplary tangentially slotted rectilinear insert 825 (FIG. 17) so as to form a horizontal row, described, supra., biospecimens 153a and 153b will be respectively carried by first flow divider 551A and base member 551B in planes that still be perpendicular to pole radius R [460] (FIG. 6A) of transverse electromagnet 400 (FIG. 6A) and will still be disposed within an annular space within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, however, force of gravity vector $F_G$ [164] (FIG. 17) will be parallel to the planes of biospecimens 153a and 153b, diamagnetic body force $F_B$ [154] (FIG. 17) will remain perpendicular to the planes of biospecimens 153a and 153b, and flow insert 551 will causes the perfusate to flow tangentially across the surfaces of biospecimens 153a and 153b in a manner that maintains the direction of a flow vector $P_F$ [190] of the perfusate normal (perpendicular) to the direction of the diamagnetic body force $F_B$ [154] induced in biospecimens 153a and 153b.

5.61 Two-dimensional Parallel-flow Bioreactor Chamber

FIG. 20F shows a cross-sectional view of an exemplary 2-D parallel-flow bioreactor chamber 550. In FIG. 20F, general port 518a of exemplary 2-D parallel-flow bioreactor chamber 550 receives first afferent perfusion tube 333p (not shown in FIG. 20F). First flow divider 551A, and base member 551B direct the perfusate to flow over exemplary biospecimen 153b. Second flow divider 551C and first flow divider 551A direct the perfusate to flow over exemplary biospecimen 153a. The perfusate leaves exemplary 2-D parallel-flow bioreactor chamber 550 through general purpose port 518b connected to first afferent perfusion tube 334p (not shown in FIG. 20F), thereby forming a closed perfusion circuit with perfusion control subsystem 250 of biological in vitro support system 200 (FIG. 1). General port 518c is closed.

Exemplary 2-D parallel-flow bioreactor chamber 550, differs from exemplary 2-D normal-flow bioreactor chamber 530, only in the manner that it orients the planes of the biospecimens it houses and sustains with respect to tangents of concentric circles having radii $R_1$ [461] and $R_2$ [462], when exemplary 2-D parallel-flow bioreactor chamber 550 is lodged within holding slots of radially slotted rectilinear insert 800 (FIG. 14, FIG. 15) or radially slotted circular insert 850 (FIG. 18, FIG. 19).

As indicated, supra., when exemplary 2-D normal-flow bioreactor chamber 540 is lodged in outer slots of tangentially slotted rectilinear insert 825 (FIG. 17) or tangentially slotted circular insert 875 (FIG. 19), it orients biospecimens 153a and 153b on planes that are parallel to tangents of concentric circles having radii $R_1$ [461] and $R_2$ [462]. However, when 2-D parallel-flow bioreactor chamber 550 is lodged within holding slots of radially slotted rectilinear insert 800 (FIG. 14, FIG. 15) or radially slotted circular insert 850 (FIG. 18, FIG. 19), it orients biospecimens 153a and 153b on planes that are perpendicular to tangents of concentric circles having radii $R_1$ [461] and $R_2$ [462].

5.62 Vector Orientations of $F_G$, $F_B$, $P_F$ for 2-D Parallel-flow Bioreactor Chamber Held in either Radially Slotted Rectilinear Insert or Radially Slotted Circular Insert as a Vertical Column Exemplary 2-D parallel-flow bioreactor chamber 550 (FIG. 20F) is the flow analogue of exemplary radial 2-D static bioreactor chamber 530 (FIG. 20C). In FIG. 20F, biospecimens 153a and 153b are spaced apart from one another such that when exemplary 2-D parallel-flow bioreactor chamber 550 is lodged within [i] exemplary first outer bioreactor chamber holding slot 807a or [ii] exemplary second outer bioreactor chamber holding slot 807c of exemplary radially slotted rectilinear insert 800 (FIG. 15) so as to form a vertical column (FIG. 15); or, [iii] exemplary outer bioreactor chamber holding slot 807a of exemplary radially slotted circular insert 850 (FIG. 18), biospecimens 153a and 153b will respectively be carried by first flow divider 551A and base member 551B in planes that align with pole radius R [460] (FIG. 6A) of transverse electromagnet 400 (FIG. 6A) and will perpendicularly intersect a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be parallel to the planes of biospecimens 153a and 153b, diamagnetic body force $F_B$ [154] (FIG. 17) will also be parallel to the planes of biospecimens 153a and 153b.

Flow insert 551 will causes the perfusate to flow tangentially across the surfaces of biospecimens 153a and 153b in a manner that maintains the direction of a flow vector $P_F$ (190) of the perfusate parallel to the direction of the diamagnetic body force $F_B$ [154] induced in biospecimens 153a and 153b.

5.63 Vector Orientations of $F_G$, $F_B$, $P_F$ for 2-D Parallel-flow Bioreactor Chamber Held in either Radially Slotted Rectilinear Insert or Radially Slotted Circular Insert as a Horizontal Row In FIG. 20F, biospecimens 153a and 153b are spaced apart from one another such that when exemplary 2-D parallel-flow bioreactor chamber 550 is lodged within [i] exemplary first outer bioreactor chamber holding slot 807a or [ii] exemplary second outer bioreactor chamber holding slot 807c of exemplary radially slotted rectilinear insert 800 (FIG. 15) so as to form a horizontal row; or, [iii] exemplary outer bioreactor chamber holding slot 807a of exemplary radially slotted circular insert 850 (FIG. 18), biospecimens 153a and 153b will respectively be carried by first flow divider 551A and base member 551B in planes that align with pole radius R [460] (FIG. 6A) of transverse electromagnet 400 (FIG. 6A) and will perpendicularly intersect a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be perpendicular to the planes of biospecimens 153a and 153b, diamagnetic body force $F_B$ [154] (FIG. 17) will be parallel to the planes of biospecimens 153a and 153b.

Flow insert 551 will causes the perfusate to flow tangentially across the surfaces of biospecimens 153a and 153b in a manner that maintains the direction of a flow vector $P_F$ (190) of the perfusate parallel to the direction of the diamagnetic body force $F_B$ [154] induced in biospecimens 153a and 153b.

Summarizing the foregoing, when flow insert 551 (FIG. 20D) is placed in interior volume 501 of common body 511 (FIG. 20A), an exemplary 2-D flow bioreactor chamber is created, which, [i] when loaded into outer holding slots of tangentially-slotted rectilinear 825 (FIG. 17), or tangentially-slotted circular insert 875 (FIG. 19), functions as exemplary 2-D normal-flow bioreactor chamber 540 (FIG. 20E); and, [ii] when loaded into outer holding slots of radially-slotted rectilinear insert 800 (FIG. 15) or radially-slotted circular insert 850 (FIG. 18), functions as exemplary 2-D parallel-flow bioreactor chamber 550 (FIG. 20F).

FIG. 20G shows a schematic cross-sectional view of common body 511 adapted to form an exemplary 3-D bioreactor chamber 560 that functions with and without perfusion. In FIG. 20G, first long double-layered wall 503L1 and second long double-layered wall 503L2 of common body 511 (FIG. 20A) are fitted with at least one pair of parallel opposing retaining clips 561, or substantially equivalent retaining devices. Three pairs of retaining clips 561 are shown for purposes of illustration in FIG. 20G.

Each pair of retaining clips 561 secures a tissue microcassette 562a, 562b, 562c, in the form of a liquid-permeable fenestrated rectangular parallelepiped that opens and closes along a hinged side (not shown in FIG. 20G) for placement of a 3-dimensional exemplary biospecimen 153 internal it walls. Biospecimens 153 may vary from tissue microcassette to tissue microcassette, and may comprise, for example, tissue scaffolds pre-seeded with osteoblasts, chondroblasts, myocytes or other cells.

In keeping with the above-described distinctions based on the orientation of planes of biospecimens relative to pole radius R [460] and tangents to concentric circles of radius $R_1$ [461] and $R_2$ [462], exemplary 3-D bioreactor chamber 560 may be used to orient the planes of tissue microcassettes 562a, 562b, 562c tangentially, so that they are perpendicular to pole radius R [460] and parallel to tangents to concentric circles of radius $R_1$ [461] and $R_2$ [462]; or, exemplary 3-D bioreactor chamber 560 may be used to orient the planes of tissue microcassettes 562a, 562b, 562c radially, so that they are aligned with pole radius R [460] and perpendicularly intersect tangents to concentric circles of radius $R_1$ [461] and $R_2$ [462].

Retaining clips 561 are spaced apart from one another such that when exemplary 3-D bioreactor chamber 560 is lodged within exemplary first outer bioreactor chamber holding slot 807a or exemplary second outer bioreactor chamber holding slot 807c of exemplary radially slotted rectilinear insert 800 (FIG. 15) or exemplary first outer bioreactor chamber holding slot 807a of exemplary radially slotted circular insert 850 (FIG. 18), the planes of tissue microcassettes 562a, 562b, 562c are perpendicular to pole radius R [460] (FIG. 6A) of transverse electromagnet 400 and will be disposed within an annular space between a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be perpendicular to the planes of tissue microcassettes 562a, 562b, 562c, and diamagnetic body force $F_B$ [154] (FIG. 17) will also be perpendicular to the planes of tissue microcassettes 562a, 562b, 562c.

Retaining clips 561 are spaced apart from one another such that when exemplary 3-D bioreactor chamber 560 is lodged within exemplary first outer bioreactor chamber holding slot 807a or exemplary second outer bioreactor chamber holding slot 807c of exemplary tangentially slotted rectilinear insert 825 (FIG. 16 ) or exemplary first outer bioreactor chamber holding slot 807a of exemplary tangentially slotted circular insert 875 (FIG. 19) the planes of tissue microcassettes 562a, 562b, 562c are aligned with pole radius R [460] of transverse electromagnet 400 (FIG. 6A) and will perpendicularly intersect a tangent to a circle of first outer radius $R_1$ [461] in region of space 438 (FIG. 6A) and a tangent to a circle of second inner radius $R_2$ [462] in region of space 438 (FIG. 6A).

In this case, force of gravity vector $F_G$ [164] (FIG. 17) will be parallel to the planes of tissue microcassettes 562a, 562b, 562c, and diamagnetic body force $F_B$ [154] (FIG. 17) will also be parallel to the planes of tissue microcassettes 562a, 562b, 562c.

If exemplary 3-D bioreactor chamber 560 disposes 3-dimensional biospecimens in region 438 and the biospecimens are not perfused, general port 518b receives first afferent gas tube 333g (not shown in FIG. 20G), general port 518c vents gas to the environment, and general port 518a is closed.

If exemplary 3-D bioreactor chamber 560 disposes 3-dimensional biospecimens in region 438 and the biospecimens are perfused, general port 518b receives first afferent perfusion tube 333p (not shown in FIG. 20G), general port 518a receives first efferent perfusion tube 334p (not shown in FIG. 20G), and general port 518c is closed.

5.64 Introduction to Second Exemplary Embodiment

FIG. 21 shows a second exemplary embodiment of the invention 102, comprising computer 201, described supra., biological in vitro support system 200, described supra, a second exemplary embodiment of a bioreactor chamber positioning system 600, a second set of exemplary bioreactor chamber embodiments 1000, and a superconducting solenoid magnet 700. As indicated in equation (4) supra., the magnitude of the diamagnetic body force $F_B$ induced in an exemplary biospecimen 153 disposed in a diamagnetic force field is proportional to the magnetic field-field gradient product B ο ∇∇B. First exemplary embodiment of the invention 101 (FIG. 1) relies primarily on the magnitude of the magnetic field gradient ∇B to generate a magnetic field-field gradient product of sufficient magnitude to be inductive of a diamagnetic body force $F_B$ in an exemplary biospecimen 153. Second exemplary embodiment of the invention relies primarily on the magnitude of the magnetic field B to generate a magnetic field-field gradient product of sufficient magnitude to be inductive of a diamagnetic body force $F_B$ in an exemplary biospecimen 153.

In second exemplary embodiment of the invention 102, a superconducting solenoid magnet 700 is adapted to generate a diamagnetic force field in the manner described supra., that is effectively confined to region of space with a solid geometry that differs from region of space 438 (FIG. 6A and FIG. 7) in which diamagnetic force field is effectively present in first exemplary embodiment of the invention 101. It is within the bounds of this second region of space, described infra., that second exemplary embodiment of a bioreactor chamber positioning system 600 disposes at least one biospecimen 153 in at least one of a plurality of exemplary bioreactor chamber embodiments forming the second set of bioreactor chamber embodiments 1000, so that there is again induced in at least one biospecimen 153 a diamagnetic force.

5.65 Superconducting Solenoid Magnet

FIG. 22A shows a schematic perspective illustration of a vertically oriented superconducting solenoid magnet 700 in a cylindrical coordinate system in whose bore there is a core cylinder 760 of space. FIG. 22B shows a schematic cross sectional view of a superconducting solenoid magnet 700 taken along line 22B-22B of FIG. 22A.

FIG. 23A shows a schematic perspective illustration of a vertically oriented superconducting solenoid magnet 700 in a cylindrical coordinate system in whose bore there is a core cylinder 760 of space containing cylindrical segments 785 and 786. FIG. 23B shows a schematic cross sectional view of a superconducting solenoid magnet 700 taken along line 23B-23B of FIG. 23A.

In FIGS. 22A, 22B and FIGS. 23A and 23B, walls of superconducting solenoid magnet 700 comprise a superconducting coil 772 in the form of a right cylindrical superconducting solenoid 773 ("main field superconducting solenoid") having a central longitudinal (z-) axis 775, along which there is measured a variable z. Main field superconducting solenoid 773 has a height H [793] and a bore radius R [791]. Dashed line 776 is a radial axis normal to central longitudinal (z-) axis 775, along which there is measured a radial variable r. Dashed line 776 intersects central longitudinal (z-) axis 775 at a longitudinal midpoint 777 of main field superconducting solenoid 773, where z=0. At points along central longitudinal (z-) axis 775 above z=0, z assumes positive values. At points along central longitudinal (z-) axis 775 below z=0, z assumes negative values. First pole 795 of main field superconducting solenoid 773 is at a distance z=+H/2 above longitudinal midpoint position 777 and second pole 796 of main field superconducting solenoid 773 is at a distance z=−H/2 below longitudinal midpoint position 777.

Superconducting coil 772 may be wound of wires made of materials, such as, for example, copper (Cu), niobium (Nb), tin (Sn), titanium (Ti), and various ceramic oxides. Superconducting coil 772 allows the flow of an electric current without the presence of significant electrical resistance at or below a critical transition temperature that depends on the material composition of its wires.

Within the region of its bore 774 near longitudinal midpoint position 777, main field superconducting solenoid 773 produces an approximately constant magnetic field inductance B(z) [171] having lines of magnetic induction parallel to central longitudinal (z-) axis 775 of solenoid superconducting magnet 700, represented by dotted lines 782.

FIG. 24A is a schematic cross-sectional illustration of the vertically oriented superconducting solenoid magnet of FIG. 22B with the addition of an exemplary first gradient coil 763 and with the addition of an exemplary second gradient coil 764.

FIG. 24B is a schematic cross-sectional illustration of the vertically oriented superconducting solenoid magnet of FIG. 23B with the addition of an exemplary first gradient coil 763 and with the addition of an exemplary second gradient coil 764.

5.66 Variation of the Magnetic Field Inductance in a Bore of a Superconducting Solenoid Magnet FIG. 25, labeled "Exemplary Axial Profile of Magnetic Field Inductance in Right Circular Cylindrical Superconducting Solenoid," is a graph of an exemplary variation of the magnitude of the magnetic field inductance B(z) [171] within bore 774 of superconducting solenoid 773 (FIGS. 22A, 22B, 23A, 23B) having a fixed radius R, as a function of linear displacement z from the longitudinal midpoint 777 of main field superconducting solenoid 773. The magnitude of the magnetic field inductance B(z) [171] is shown as a function of linear displacement z in opposing directions from longitudinal midpoint 777, at which z=0, of main field superconducting solenoid 773.

The ordinate in FIG. 25, labeled "Magnetic Field Inductance (Tesla)," is scaled in relative Tesla, and the abscissa in FIG. 25, labeled "Axial Distance (mm)," is scaled in relative millimeters from midpoint 777, with z taking on negative values in the direction of second pole 796 (z=−H/2) of main field superconducting solenoid 773; and, with z taking on positive values in the direction of first pole 795 (z=+H/2) of main field superconducting solenoid 773. H is the height of main field superconducting solenoid 773. In the direction of first pole 795, there is shown first "shoulder" region 761. In the direction of second pole 796, there is shown as second "shoulder" region 762.

For purposes of illustrating the effect of exemplary gradient-enhancing coils 763 and 764 on the magnitude of the magnetic inductance B(z) [171] within bore 774 of superconducting solenoid 773, shown in FIGS. 22A, 22B, 23A, 23B, the graph shown in FIG. 25 exaggerates the extent of the region about z=0 in which the magnitude of the magnetic inductance B(z) [171] is relatively constant.

FIG. 26, labeled "Exemplary Gradient Coil-Enhanced Axial Profile of Magnetic Field Inductance in Right Circular Cylindrical Superconducting Solenoid," is a graph of an exemplary variation of the magnitude of the magnetic field inductance B(z) [171] within bore 774 of superconducting solenoid 773 of a fixed radius R, which magnetic field inductance has been altered by exemplary gradient coils 763 and 764 as shown in FIG. 24A and FIG. 24B. As in the graph of FIG. 25, the magnitude of the magnetic field inductance B(z) [171] is shown as a function of linear displacement z from the longitudinal midpoint 777 of main field superconducting solenoid 773, at which z=0.

As in the graph of FIG. 25, the ordinate in FIG. 26, labeled "Magnetic Field Inductance (Tesla)," is scaled in relative Tesla, and the abscissa, labeled "Axial Distance (mm)," is scaled relative millimeters from midpoint 777, with z taking on negative values in the direction of second pole 796 (z=−H/2) of main field superconducting solenoid 773; and, with z taking on positive values in the direction of first pole 795 (z=+H/2) of main field superconducting solenoid 773, where H is the height of main field superconducting solenoid 773. In the direction of first pole 795, there is shown first "shoulder" region 761a. In the direction of second pole 796, there is shown as second "shoulder" region 762a.

5.67 Variation of the Magnetic Field Gradient in a Bore of a Superconducting Solenoid Magnet FIG. 27, labeled "Exemplary Magnetic Field Gradient in Right Circular Cylindrical Superconducting Solenoid," is a graph of an exemplary variation of the magnitude of magnetic field gradient $\partial B(z)/\partial z$ [181] as a function of linear displacement z from the longitudinal midpoint 777 of main field superconducting solenoid 773, shown in FIGS. 22A, 22B, 23A, 23B. In FIG. 27, the ordinate, labeled "Magnetic Field Gradient $\partial B(z)\partial z$ (Tesla/m)," is scaled in relative Tesla/meter and the abscissa, labeled "Axial Position (mm)," is scaled relative millimeters from midpoint 777, with z taking on negative values in the direction of second pole 796 (z=−H/2) of main field superconducting solenoid 773; and, with z taking on positive values in the direction of first pole 795 (z=+H/2) of main field superconducting solenoid 773, where H is the height of main field superconducting solenoid 773. The magnitude of the magnetic field gradient $\partial B(z)/\partial z$ [181] has a superior (+) direction for all z>0 and has an inferior (−) direction for all z<0. The magnitude of the magnetic field gradient $\partial B(z)/\partial z$ [181] is equal to zero only at z=0.

5.68 Variation of the Magnetic Field Gradient Product in a Bore of a Superconducting Solenoid Magnet FIG. 28, labeled "Exemplary Magnetic Field-Field Gradient Product in Right Circular Cylindrical Superconducting Solenoid," is a graph of an exemplary variation of the magnitude of the magnetic field-field gradient product B(z)$\partial B/\partial z$ [183] within bore 774 of superconducting solenoid 773, shown in FIGS. 22A, 22B, 23A, 23B, of a fixed radius R, as a function of linear displacement z from the longitudinal midpoint 777 of main field superconducting solenoid 773, at which z=0. In FIG. 28, the ordinate, labeled "Field-Gradient Product B(z)$\partial B/\partial z$ (Tesla$^2$/m)," is scaled in relative square Tesla per meter and the abscissa, labeled "Axial Position," is scaled relative, millimeters from midpoint 777, with z taking on negative values in the direction of second pole 796 (z=−H/2) of main field superconducting solenoid 773; and, with z taking on positive values in the direction of first pole 795 (z=+H/2) of main field superconducting solenoid 773, where H is the height of main field superconducting solenoid 773.

As shown in FIG. 25, within bore 774 of main field superconducting solenoid 773, the magnitude of the magnetic field inductance B(z) [181] is relatively constant, until z approaches either of two opposing "shoulders," 761 and 762. At z=0, the magnitude of the magnetic field inductance B(z) [171] is constant (FIG. 25); and, as shown in FIG. 27, the magnitude of the magnetic field gradient $\partial B(z)/\partial z$ [181] =0.

At points other than z=0, the magnitudes of B(z) [171] (FIG. 25) and ∂B(z)/∂z [181] (FIG. 27), within a right cylindrical superconducting solenoid are functions of several design variables, such as, for example, the presence and location of gradient-enhancing coils, or the presence and location of magnetic field stabilization coils added to main field superconducting solenoid 773.

For purposes of illustration, and in the absence of any gradient-enhancing coils, the graph of FIG. 25 shows that within the region inclusive of z=0 and bounded by first "shoulder" region 761 and second "shoulder" region 762, the magnitude of the magnetic field inductance B(z) [171] is relatively constant, having some variation owing to the presence of a magnetic field gradient ∂B(z)/∂z [181] of moderate magnitude (FIG. 27).

Outside of the region bounded by first "shoulder" region 761 and second "shoulder" region 762 the magnitude of the magnetic field inductance B(z) [171] declines sharply under the influence of an increasingly strong magnetic field gradient ∂B(z)/∂z [181] (FIG. 27). In the graph shown in FIG. 26, the symmetric "shoulders" 761 and 762 of the graph of B(z) [171] in FIG. 25 have been steepened by the gradient coils 762 and 764 (FIG. 24A and FIG. 24B) to produce the correspondingly steepened symmetric "shoulders" 761a and 762a of the graph of B(z) [171] shown in FIG. 26.

5.69 Axial Maxima of the Magnetic Field Gradient in a Bore of a Superconducting Solenoid Magnet As shown in FIG. 27, within bore 774 of any right cylindrical superconducting solenoid, such as main field superconducting solenoid 773 (FIGS. 22A, 22B, 23A, 23B), the magnitude of the magnetic field gradient ∂B(z)/∂z [181] will always exhibit bipolar relatively symmetric maxima ∂B($z_{maxA1}$)/∂z and ∂B($z_{maxA1}$)/∂z at relatively symmetrically opposing points:

z=$z_{maxA1}$, in the vicinity of first pole 795 (FIGS. 22A, 22B, 23A, 23B); and at, z=$z_{maxA2}$, in the vicinity of second pole 796 (FIGS. 22A, 22B, 23A, 23B).

5.70 First and Second Axial Maxima of the Magnetic Field-Field Gradient Product in a Bore of a Superconducting Solenoid Magnet As shown in FIG. 28, within bore 774 of any right cylindrical superconducting solenoid, such as main field superconducting solenoid 773 (FIGS. 22A, 22B, 23A, 23B), the magnitude of the magnetic field-field gradient product B(z)∂B/∂z [183] will also exhibit bipolar relatively symmetric maxima:

[B($z_{maxB1}$)]∂B($z_{maxB1}$)/∂z at a first axial maximum point where z=$z_{maxB1}$, in the vicinity of first pole 795; and

[B($z_{maxB2}$)]∂B($z_{maxB2}$)/∂z at a symmetrically opposing second axial maximum point, where z=$z_{maxB2}$, in the vicinity of second pole 796.

The first axial maximum point at z=$z_{max\,B1}$ and opposing second axial maximum point at z=$z_{max\,B2}$ correspond to the points at which the graph of B(z) [171] v. z shown in FIG. 25, and the graph of ∂B(z)/∂z [181] v. z, shown in FIG. 27 intersect. FIG. 29 is a dual-ordinate plot of B(z) [171] (in Tesla) v. z and ∂B(z)/∂z [181] (in Tesla/m) v. z against a common abscissa, labeled "Axial Position (mm)," scaled in relative millimeters, and shows one such point of intersection at first axial maximum point at z=$z_{max\,B1}$ in the vicinity of first pole 795 of main field superconducting solenoid 773, where z≧0.

Accordingly, within bore 774 of any right cylindrical superconducting solenoid, however configured by the addition of axially symmetric stabilizing coils or axially symmetric gradient coils, the magnitude of the magnetic field-field gradient product B(z)∂B/∂z [183]—that is, the vector dot product of the magnetic field inductance B(z) [171] with the magnetic gradient ∂B(z)/∂z [181]—will always have two substantially symmetrical and opposing maxima at the two substantially symmetrical and opposing points z=$z_{max\,B1}$ and z=$z_{maxB2}$ where the graphs of B(z) [171] v. z and ∂B(z)/∂z [181] v. z intersect. And, when activated, superconducting coil 772 of second embodiment of the invention 102 (FIG. 21), however configured by the addition of stabilizing coils or gradient coils, generates a diamagnetic force field as described supra., generative of a diamagnetic body force, also as described supra.

5.71 Diamagnetic Force Field Spatial Geometry in a Core Cylinder of the Bore of a Superconducting Solenoid Magnet Referring again to FIG. 22A and FIG. 22B, in bore 774 of main field superconducting solenoid 773, the diamagnetic force field will occupy a spatial region comprising the walls and volume of a core cylinder 760 coincident with bore 714 of superconducting solenoid magnet 700.

5.72 Core Cylinder has a First Outer Base and a Second Outer Base

In FIG. 22A and FIG. 22B, core cylinder 760 has a first outer base 789 and an opposing second outer base 794. First outer base 789 and an opposing second outer base 794 are each [i] respectively perpendicular to central longitudinal z-axis 775 of superconducting solenoid magnet 700, [ii] respectively proximal to opposing first and second poles 795 and 796 of superconducting solenoid magnet 700, and [iii] respectively equidistant from longitudinal midpoint 777 of bore 774 of superconducting solenoid magnet 700.

5.73 First Outer Base and a Second Outer Base of Core Cylinder Respectively Contain the Points at which B(z)∂B/∂z has a First and Second Outer Threshold Value First outer base 789 of core cylinder contains a first outer threshold point (not shown in FIG. 22A or FIG. 22B) on central longitudinal z-axis 775 of solenoid superconducting magnet 700 at which the magnetic field-field gradient product B(z)∂B/∂z [183] of superconducting solenoid magnet 700 has a first outer threshold value that is about 20 percent of the first maximum axial value [B($z_{maxB1}$)]∂B($z_{maxB1}$)/∂z. Second outer base 794 contains a second outer threshold point (not shown in FIG. 22A or FIG. 22B) on central longitudinal z-axis 775 of solenoid superconducting magnet embodiment 700 at which the magnetic field-field gradient product B(z) ∂B/∂z [183] of superconducting solenoid magnet 700 has a second outer threshold value that is about 20 percent of the second maximum axial value [B($z_{maxB2}$)]∂B($z_{maxB2}$)/∂z.

5.74 Core Cylinder Contains the Points at which B(z)∂B/∂z has First and Second Maximum Values Core cylinder 760 contains the aforesaid first axial maximum point coincident with the point, on central longitudinal z-axis 775 of solenoid superconducting magnet embodiment 700, z=$z_{maxB1}$, at which the magnetic field-field gradient product B(z)∂B/∂z [183] has a first maximum axial value of magnitude [B($z_{maxB1}$)]∂B($z_{maxB1}$)/∂z. Core cylinder 760 also contains the aforesaid second axial maximum point coincident with the symmetrically opposed point on central longitudinal z-axis 775 of solenoid superconducting magnet embodiment 700, z=$z_{maxB2}$, at which the magnetic field-field gradient product B(z)∂B/∂z [183] also has a symmetrically opposed second maximum axial value of magnitude [B($z_{maxB2}$)]∂B($z_{maxB2}$)/∂z.

5.75 Core Cylinder Containing Cylindrical Segments with Midplanes that Respectively Contain Points at which B(z)∂B/∂z has First and Second Maximum Value As shown in FIG. 23A and FIG. 23B, core cylinder 760 may conveniently be subdivided to include a first right cylindrical segment of space 785, coincident with bore 774, and having a first segmental midplane 766 that contains the aforesaid first axial maximum point $z=z_{maxB1}$, (not shown in FIG. 23A and FIG. 23B) at which the magnetic field-field gradient product B(z)∂B/∂z [183] has the aforesaid first maximum axial value of magnitude $[B(z_{maxB1})]\partial B(z_{maxB1})/\partial z$.

Core cylinder 760 may further be conveniently be subdivided to include a symmetrically opposed second right cylindrical segment of space 786, coincident with bore 774, having a second segmental midplane 767 that contains the aforesaid second axial maximum point $z=z_{maxB2}$, (not shown in FIG. 23A and FIG. 23B) at which the magnetic field-field gradient product B(z)∂B/∂z [183] has the aforesaid second maximum axial value of magnitude $[B(z_{maxB2})]\partial B(z_{maxB2})/\partial z$.

5.76 Core Cylinder Containing Cylindrical Segments with Inner Bases that Respectively Contain Points at which B(z)∂B/∂z has First and Second Inner Threshold Values As shown in FIG. 23A and FIG. 23B, first cylindrical segment of space 785 has a first inner base 787 and second cylindrical segment of space 786 has an opposing second inner base 788, each inner base 786, 787 being approximately equidistant from longitudinal midpoint 777 at z=0 of main field superconducting solenoid 773.

First inner base 786 contains a first inner threshold point (not shown in FIG. 23A or FIG. 23B) at which the magnetic field-field gradient product B(z)∂B/∂z [183] of superconducting solenoid magnet 700 has a first inner threshold value that is about 80 percent of the first maximum axial value $[B(z_{maxB1})]\partial B(z_{maxB1})/\partial z$.

Second inner base 787 contains a second inner threshold point (not shown in FIG. 23A or FIG. 23B) at which the magnetic field-field gradient product B(z)∂B/∂z [183] of superconducting solenoid magnet 700 has a second inner threshold value that is that is about 80 percent of the second maximum axial value $[B(z_{maxB2})]\partial B(z_{maxB2})/\partial z$.

First cylindrical segment of space 785 also has first outer base 789, and second cylindrical segment of space 786 also has opposing second outer base 794, described supra.

Summarizing, the diamagnetic force field of superconducting solenoid magnet 700 that is generative of diamagnetic body force $F_B(z)$ [154] occupies a spatial region comprising the walls and volume of a core cylinder 760 containing:

[i] a first axial maximum point coincident with point $z=z_{maxB1}$, at which the magnetic field-field gradient product B(z)∂B/∂z [183] has a first maximum axial value of magnitude $[B(z_{maxB1})]\partial B(z_{maxB1})/\partial z$ and,

[ii] a second axial maximum point coincident with symmetrically opposed point $z=z_{maxB2}$, at which the magnetic field-field gradient product B(z)∂B/∂z [183] has a symmetrically opposed second maximum axial value of magnitude $[B(z_{maxB2})]\partial B(z_{maxB2})/\partial z$. Core cylinder 760 also has:

[i] first outer base 789 containing first outer threshold point at which the magnetic field-field gradient product B(z)∂B/∂z [183] has a first outer threshold value that is about 20 percent of the first maximum axial value (i.e., 0.20 $B(z_{maxB1})\partial B(z_{maxB1})/\partial z$); and,

[ii] second outer base 794 containing second outer threshold point at which the magnetic field-field gradient product B(z)∂B/∂z [183] has a second outer threshold value that is about 20 percent of the second maximum axial value (i.e., 0.20 $B(z_{maxB2})\partial B(z_{maxB2})/\partial z$).

5.77 Diamagnetic Force Field in Spatial Distribution of Cylindrical Segments Diamagnetic force field of superconducting solenoid magnet 700 generative of diamagnetic, body force $F_B(z)$ [154] also occupies a spatial region comprising the walls and volume of a. first right cylindrical segment of space 785, having

[i] a first inner base 787 containing a first inner threshold point at which the magnetic field-field gradient product B(z)∂B/∂z [183] has a first inner threshold value that is about 80 percent of the first maximum axial value (i.e., ≅0.80 $B(z_{maxB1})\partial B(z_{maxB1})/\partial z$), and

[ii] a first outer base 789 containing a first outer threshold point at which the magnetic field-field gradient product B(z)∂B/∂z [183] has a first outer threshold value that is about 20 percent of the first maximum axial value (i.e., ≅ 0.20 $B(z_{maxB1})\partial B(z_{maxB1})/\partial z$),

[iii] between which first inner base 787 and first outer base 789 there is first segmental midplane 766 containing the first axial maximum point $z=z_{maxB1}$, at which the magnetic field-field gradient product B(z)∂B/∂z [183] has the first maximum axial value of magnitude $[B(z_{maxB1})]\partial B(z_{maxB1})/\partial z$; and, b. a second right cylindrical segment of space 786, having

[i] second inner base 788 containing second inner threshold point at which the magnetic field-field gradient product B(z)∂B/∂z [183] has a second inner threshold value that is about 80 percent of the second maximum axial value (i.e., ≅ 0.80 $B(z_{maxB1})\partial B(z_{maxB1})/\partial z$); and,

[ii] a second outer base 794 containing a second outer threshold point at which the magnetic field-field gradient product B(z)∂B/∂z has a second outer threshold value that is about 20 percent of the second maximum axial value (i.e., ≅0.20 $B(z_{maxB2})\partial B(z_{maxB2})/\partial z$,

[iii] between which second inner base 788 and second outer base 794, there is second segmental midplane 767 containing second axial maximum point $z=z_{maxB2}$], at which the magnetic field-field gradient product B(z)∂B/∂z [183] also has a maximum axial value of magnitude $[B(z_{maxB2})]\partial B(z_{maxB2})/\partial z$.

5.78 Exemplary Superconducting Magnet

FIG. 30 is a schematic cross-sectional illustration of a vertically oriented solenoid superconducting magnet, showing main field superconducting solenoid 773 and several exemplary of locations within bore 774 for disposing biospecimens in diamagnetic force field.

The solenoid superconducting magnet shown schematically in FIG. 30 and adapted for use in the second exemplary embodiment of the invention 102 may, for example, be a superconducting magnet manufactured by Oxford Instruments, Concord, Mass., generally having the technical specifications appearing in Table 2, productive of a magnetic field inductance B of about 16 T at about 4 degrees Kelvin, at points within bore 774 on the horizontal midplane containing longitudinal midpoint 777; and, further productive of a maximum magnetic field-field gradient product B(z)∂B/∂z [183] of about 1620 $T^2$/m at a point $z_{maxB1}$ about 56 mm above longitudinal midpoint 777 and at a point $z_{maxB2}$ about 56 mm below longitudinal midpoint 777.

TABLE 2

SPECIFICATIONS AND TEST RESULTS FOR SUPERCONDUCTING MAGNET

| Measurement | Result |
| --- | --- |
| Measured central fluid/current ratio | 0.1878 T/A |
| Maximum central field activated at 4.2° K during testing | >15.0 T |
| Quench current achieved at 4.2° K | 109.5 A |
| Maximum central field activated at 2.2° K during testing | >16.3 T |
| Quench current achieved at 2.2° K | 118.7 A |
| Guaranteed field gradient product at 2.2° K | 22 T$^2$/m |
| Central field for guaranteed field gradient product | 15.98 T |
| Maximum field gradient product achieved during testing | >22.5 T$^2$/m |
| Computed homogeneity | 0.1% |
| Current decay in persistent mode | <1 × 10$^{-4}$/hr |
| Clear bore diameter | 32 mm |
| Magnetic field center from base of magnet | 86.4 mm |
| Overall magnet height | 275 mm |
| Switch heater current for open state (nominal) | 80 mA |
| Maximum energization voltage | 4 v |
| Resistance values at 300° K Magnetic resistance start-finish | 48.8 ohm |
| Resistance values at 300° K Magnetic Superconductor switch resistance (nominal) | 50 ohm |
| Resistance values at 300° K Switch heater resistance | 99.5 ohm |
| Resistance values at 300° K Spare switch heater resistance | 100.5 ohm |

In FIG. 30, at position $A_0$ corresponding to longitudinal midpoint 777 (FIG. 22→22A, FIG. 23=22B. FIG. 23A and FIG. 23B), the magnitude of magnetic field $B(A_0)$ is at a maximum of about 16 T and both $B(A_0)\partial B(A_0)/\partial z$ and corresponding diamagnetic body force $F_B(A_0)$ is zero.

In FIG. 30, at position $A_1$, the magnetic field-field gradient product $B(A_1)\partial B(A_1)/\partial z$ is at earlier-defined position $z_{maxB1}$ (FIG. 28), with a maximum value of about 1620 T$^2$/m, and corresponding diamagnetic body force $F_B(A_1)$, induced in an exemplary biospecimen 153 disposed in position $A_1$ by second exemplary embodiment of bioreactor chamber positioning system 600 (FIG. 21) and housed and sustained in vitro in position $A_1$ by biological in vitro support system 200 (FIG. 21), is directed superiorly and opposes any downwardly directed body force, such as, for example, force of gravity $F_G$ [164].

In FIG. 30, at position $A_4$, the magnetic field-field gradient product $B(A_4)\partial B(A_4)/\partial z$ is at earlier-defined position $z_{maxB2}$ (FIG. 28), also having a maximum value of about 1620 T$^2$/m, and corresponding diamagnetic body force $F_B(A_4)$, induced in an exemplary biospecimen 153, disposed in position $A_4$ by second exemplary embodiment of bioreactor chamber positioning system 600 (FIG. 21) and housed and sustained in vitro in position $A_4$ by biological in vitro support system 200 (FIG. 21), is directed inferiorly and augments any other downwardly directed body force, such as, for example, force of gravity $F_G$ [164].

In FIG. 30, at intermediate position $A_2$, diamagnetic body force $F_B(A_2)$ (not shown in FIG. 30) has a value between zero and its maximum value, is directed superiorly, and partially opposes any downwardly directed body force, such as, for example, force of gravity $F_G$ [164]; and, at intermediate positions $A_3$, diamagnetic body force $F_B(A_3)$ (not shown in FIG. 30) also has a value between zero and its maximum value, is directed inferiorly, and partially augments any other downwardly directed body force, such as, for example, force of gravity $F_G$ [164].

5.79 Biological in vitro Support System of Second Exemplary Embodiment

As shown in FIG. 21, by analogy with the first exemplary embodiment of the invention 101 (FIG. 1), in the second exemplary embodiment of the invention 102, biological in vitro support system 200, under the operational control of computer 201, is configured to independently route a second set of tubes 390 from biological in vitro support system 200 to an exemplary cylindrical housing 610 (FIG. 21) and to each of a plurality of exemplary bioreactor chamber embodiments forming a second set of bioreactor chamber embodiments 1000 (FIG. 21), and to return the second set of tubes 390 from exemplary cylindrical housing 610 and each of these exemplary bioreactor chambers to biological in vitro support system 200, thereby completing a closed circuit for each second set of tubing 390.

5.80 Second Set of Tubes of Second Exemplary Embodiment

As shown in FIG. 21, each second set of tubes 390 is comprised of a second afferent tube bundle 393 and a second efferent tube bundle 394. Each second afferent tube bundle 393 is a triplet of tubes comprised of a second afferent gas tube 393g, a second afferent temperature tube 393t, and a second afferent perfusion tube 393p, respectively elaborated from gas flow control subsystem 230, temperature control subsystem 240, and perfusion control subsystem 250 of biological in vitro support system 200. Each second efferent tube bundle 394 is a doublet of tubes comprised of a second efferent temperature tube 394t, and a second efferent perfusion tube 394p, respectively returning to temperature control subsystem 240, and perfusion control subsystem 250 of biological in vitro support system 200.

By analogy with first embodiment of the invention, in second embodiment of the invention 102, second afferent gas tube 393g, second afferent perfusion tube 393p and second efferent perfusion tube 394p communicate with each of a plurality of exemplary bioreactor chamber embodiments forming a second set of bioreactor chamber embodiments 1000.

By analogy with first embodiment of the invention, in second embodiment of the invention 102, there is no tubing for the return of gas provided to bioreactor chamber embodiments 1000 because gas from these bioreactor chamber embodiments is vented to the environment directly from an efferent gas port built into each bioreactor chamber embodiment, as more fully described infra.

However, unlike first embodiment of the invention, in second embodiment of the invention 102, second afferent temperature tube 393t and second efferent temperature tube 394t form a closed tubing circuit for the control of temperature with a water-tight jacket circumscribing cylindrical housing 610 (FIG. 31), rather than forming a closed tubing circuit for the control of temperature with each of the plurality of exemplary bioreactor chamber embodiments forming a second set of bioreactor chamber embodiments 1000.

5.81 Bioreactor Positioning System of Second Exemplary Embodiment

By further analogy with first exemplary embodiment of the invention 101, in the second exemplary embodiment of the invention 102, biological in vitro support system 200 sustains at least one biospecimen 153 in vitro in at least one of a plurality of exemplary bioreactor chamber embodiments forming a second set of bioreactor chamber embodiments 1000 and second exemplary embodiment of bioreactor chamber positioning system 600 disposes these biospecimen 153 within a diamagnetic force field generated by superconducting magnet 700, for example, in exemplary spatial regions $A_0$, $A_1$, $A_2$, $A_3$, $A_4$, and $A_5$ shown in FIG. 30, so that there is induced in biospecimen 153 a diamagnetic body force $F_B$.

As shown schematically in FIG. 21, in second exemplary embodiment of the invention, superconducting magnet 700 replaces transverse electromagnet 400 (FIG. 1) of first exemplary embodiment of the invention 101, and anterior terminus 306 of nonmagnetic positioning arm 305 is adapted to support an exemplary cylindrical housing 610 (FIG. 31), in lieu of exemplary rectilinear frame 311 (FIG. 12) or exemplary circular frame 370 (FIG. 13), and to precisely position exemplary cylindrical housing 610 within bore 774 of main field superconducting solenoid 773 so as to dispose one or more bioreactor chamber embodiments of second set of bioreactor chamber embodiments 1000 into exemplary spatial regions $A_0, A_1, A_2, A_3$, and $A_4$ (FIG. 30), thereby exposing biospecimens 153 sustained in bioreactor chamber embodiments 1000 and disposed in exemplary regions $A_1, A_2, A_3$, and $A_4$ to a diamagnetic force field inductive in these biospecimens of a diamagnetic body force, as described supra.

5.82 Exemplary Cylindrical Housing 610 of Second Exemplary Embodiment

FIG. 31 is a perspective schematic illustration of an exemplary cylindrical housing 610 of a second exemplary embodiment of the invention 102 (FIG. 21). As shown in FIG. 31, exemplary cylindrical housing 610 comprises a right circular cylinder, whose circumscribing wall 61 1 and opposing superior base 612 and inferior base 613 are made of a nonmagnetic material such as, for example, Nylon, Plexiglass® (polymethylmethacrylate), Lexan® polycarbonate resin, or a substantially equivalent material. Exemplary cylindrical housing 610 has a height of about 170 mm and a radius of about 25 mm.

Circumscribing wall 611 is double-layered, having an inner wall 611*i* and an outer wall 611*o* that define an intervening space forming a cylindrical water-tight jacket 623. Circumscribing wall 611 is about 5 mm thick, with inner wall 611*i* and outer wall 611*o* each being about 1.5 mm thick, and intervening space forming cylindrical water-tight jacket 623 being about 2 mm wide. Afferent cylindrical temperature port 624 is fashioned into water-tight jacket 625 and efferent cylindrical temperature port 624 is also fashioned into water-tight jacket 623. Afferent cylindrical temperature port 624 receives second afferent temperature tube 393*t* of second afferent tube bundle 393 of second set of tubes 390 (FIG. 21) and efferent cylindrical temperature port 625 receives second efferent temperature tube 394*t* of second efferent tube bundle 394 of second set of tubes 390 (FIG. 21). Afferent cylindrical temperature port 624 and efferent cylindrical temperature port 624 thereby complete a fluid circulation loop between cylindrical water-tight jacket 623 and temperature control subsystem 240 of biological in vitro support system 200 (FIG. 21).

Circumscribing wall 611 has a first vertical water-tight discontinuity 615 about which circumscribing wall 611 is hinged to open and close against a second opposing vertical water-tight discontinuity 616. Opposing superior base 612 and inferior base 613 respectively have horizontal water-tight discontinuities 617 and 618 along their respective diameters that are contiguous with vertical discontinuities 615 and 616 in circumscribing wall 611, thereby dividing exemplary cylindrical housing 610 longitudinally and forming paired water-tight hemi-cylindrical doors 619*a* and 619*b* to interior volume 609 of exemplary cylindrical housing 610. Closure of paired water-tight hemi-cylindrical doors 619*a* and 619*b* is maintained by clasps (not shown in FIG. 31) along second opposing vertical water-tight discontinuity 616 and horizontal water-tight discontinuities 617 and 618.

The surfaces of first vertical water-tight discontinuity 615, second opposing vertical water-tight discontinuity 616, and horizontal water-tight discontinuities 617 and 618 are coated with a nonmagnetic water-tight sealant such as, for example, rubber or silicone, or a substantially equivalent material, thereby enabling cylindrical water-tight jacket 623 to circumscribe interior volume 609 when exemplary cylindrical housing 610 is closed.

Exemplary cylindrical housing 610 has a central longitudinal axis 614, that is coincident with central longitudinal (z-) axis 775 of main field superconducting solenoid 773, (FIG. 22A and FIG. 23A) when exemplary cylindrical housing 610 is disposed within bore 774 (FIG. 22A and FIG. 23A) of main field superconducting solenoid 773 (FIG. 22A and FIG. 23A) by second exemplary embodiment of bioreactor chamber positioning system 600 (FIG. 21).

Inner aspect 620 of inner wall 611*i* is fabricated to form a plurality of ring-like ledges 621 for the support of bioreactor chamber embodiments of second set of exemplary bioreactor chamber embodiments 1000 (not shown in FIG. 31). Ledges 621 may, for example, be arrayed vertically about 30 mm apart to place bioreactor chamber embodiments of second set of exemplary bioreactor chamber embodiments 1000 at the vertical midpoints of regions $A_0, A_1, A_2, A_3, A_4$, and $A_5$ shown in FIG. 30. Opposing superior base 612 and inferior base 613 are fabricated with a plurality of housing conduits 622 adapted to conduct second afferent gas tube 393*g* and second afferent perfusion tube 393*p* of second afferent tube bundle 393 from biological in vitro support system 200 to bioreactor chamber embodiments of second set of exemplary bioreactor chamber embodiments 1000 lodged on ring-like ledges 621 and to conduct second efferent perfusion tube 394*p* of second efferent tube bundle 394 from these bioreactor chambers 1000 back to biological in vitro support system 200 (FIG. 21), thereby forming as closed circuit, as described supra.

5.83 Common Body of Exemplary Bioreactor Chambers of Second Exemplary Embodiment Bioreactor chamber embodiments of second set of exemplary bioreactor chamber embodiments 1000 are cylindrical analogues of first set of exemplary bioreactor chamber embodiments 500 adapted to the cylindrical geometry of superconducting magnet 700.

FIG. 32 shows a schematic cross-sectional view of an exemplary water-tight nonmagnetic cylindrical body 1011 common to the plurality of exemplary bioreactor chamber embodiments forming second set of bioreactor chamber embodiments 1000. Exemplary water-tight nonmagnetic common cylindrical body 1011 is made of a nonmagnetic, water-impermeable material, such as, for example, Nylon, Plexiglass® (polymethylmethacrylate), Lexan® polycarbonate resin, or a substantially equivalent material.

Exemplary water-tight nonmagnetic common cylindrical body 1011 has a cylindrical chamber wall 1012, circumscribing an interior volume 1013, and has paired opposing superior and inferior cylindrical bases 1014 and 1015, respectively above and below interior volume 1013. Cylindrical chamber wall 1012 is joined to inferior opposing cylindrical base 1014 in a water tight fashion by suitable adhesives to form a right circular cylinder about interior volume 1013. Superior cylindrical base 1014, also serving as a water-tight cap by which the water-tight interior volume 1013 of exemplary water-tight nonmagnetic common cylindrical body 1011 is accessed, is detachably removable from exemplary water-tight nonmagnetic common cylindrical body 1011, and is made of nonmagnetic rubber, or a substantially equivalent sealing material.

Exemplary water-tight nonmagnetic common cylindrical body 1011 has an outer diameter of about 20 mm, an inner diameter of about 16 mm, and a height of about 30 mm. Cylindrical chamber wall 1012 is about 2 mm thick, having an inner wall surface 1012i and an outer wall surface 1012o. Superior and inferior opposing cylindrical bases 1014 and 1015 are each about 4 mm thick.

Exemplary water-tight nonmagnetic common cylindrical body 1011 has three general ports 518a, 518b, and 518c, for venting gas and/or detachably and exchangeably connecting, in appropriate combinations that depend on the desired in vitro environment, second afferent gas tube 393g (FIG. 21), second afferent perfusion tube 393p (FIG. 21), and second efferent perfusion tube 394p (FIG. 21). Any general purpose port 518a, 518b, and 518c, may also be used for sampling fluid provided to water tight interior 1013 by biological in vitro support system 200 (FIG. 21).

5.84 Axial Exemplary Bioreactor Chamber

FIG. 33 shows a schematic perspective view of exemplary water-tight nonmagnetic common cylindrical body 1011 in which an inner surface of cylindrical chamber wall 1012 has been formed with longitudinal channels (not shown in FIG. 33) adapted to secure an axial spacer 1009a that axially divides interior volume 1013 and to secure axial plates 1008a that are parallel to housing longitudinal axis 614 of cylindrical housing 610 (FIG. 31). Axial spacer 1009a is made of a nonmagnetic, water-impermeable material, such as, for example, Nylon, Plexiglass® (polymethylmethacrylate), Lexan® polycarbonate resin, or a substantially equivalent material, fashioned into a rectangular insert having a width of about 16 mm, a height of about 20 mm and a thickness of about 0.4 mm. Axial plates 1008a may comprise slides or substantially equivalent planar surfaces having a width of about 12 mm, a height of about 12 mm and a thickness of about 0.2 mm.

5.85 Trans-Axial Exemplary Bioreactor Chamber

FIG. 34 shows a schematic cross-sectional view of exemplary water-tight nonmagnetic common cylindrical body 1011 with interior volume 1013 stackable annular trans-axial spacers 1009 adapted to support biospecimens 153 trans-axially in planes that are perpendicular to housing longitudinal axis 614 of cylindrical housing 610 (FIG. 31).

Trans-axial spacers 1009 may be made of a nonmagnetic, water-impermeable material, such as, for example, Nylon, Plexiglass® (polymethylmethacrylate), Lexan® polycarbonate resin, or a substantially equivalent material, fashioned into annular segments that are adapted to fit within volume 1013 of exemplary water-tight nonmagnetic common cylindrical body 1011 against the inner surface 1012i of longitudinal wall 1012. Trans-axial spacers 1009 may, for example, have an inner diameter of about 12 mm, and outer diameter of about 16 mm and a height of about 5 mm As shown in FIG. 34, trans-axial spacers 1009 support trans-axial disks 1008. Each trans-axial disk 1008 may be a slide, or substantially equivalent planar surface having a diameter of about 15 mm and thickness of about 0.2 mm. A columnar array of trans-axial spacers 1009 alternating with trans-axial disks 1008 may be stacked axially within interior volume 1013 of exemplary water-tight nonmagnetic common cylindrical body 1011. Each slide may support a different biospecimen (not shown in FIG. 34).

By analogy with first set of exemplary bioreactor chamber embodiments 500, exemplary water-tight nonmagnetic common cylindrical body 1011 may be adapted as a bioreactor chamber to provide:

[i] perfused or non-perfused in vitro support for two-dimensional growth of biospecimens upon surfaces or substrates parallel to central longitudinal z-axis 775 of solenoid superconducting magnet embodiment 700 (FIG. 22A. FIG. 23A); or

[ii] perfused or non-perfused in vitro support for two-dimensional growth of biospecimens upon surfaces or substrates perpendicular to central longitudinal z-axis 775 of solenoid superconducting magnet embodiment 700 (FIG. 22A. FIG. 23A); or,

[iii] perfused or non-perfused in vitro support for three-dimensional growth of biospecimens within tissue microcassettes with or without scaffolding.

It will be appreciated by those skilled in the art that, the structural and functional integration of the inventive elements of the foregoing embodiments of the present invention are exemplary only and that other arrangements for integrating the inventive elements may be used which are within the scope and spirit of the present invention.

We claim:

1. An apparatus comprising a transverse electromagnet 400, at least one region of region of space, a bioreactor positioning system and at least one bioreactor chamber adapted to house at least one biospecimen in said at least one region of space; said biospecimen comprising at least one cell, or at least one fluid and at least one cellular monolayer having a basal surface and a luminal surface, which basal surface may be grown on a substrate; said transverse electromagnet inducing a diamagnetic body force in said at least one biospecimen; said at least one bioreactor chamber being further adapted to sustain said at least one biospecimen in vitro in said at least one region of space by means of biological in vitro support system 200; said bioreactor chamber being disposed in said at least one region of space by said bioreactor positioning system and being operationally connected to said biological in vitro support system 200; wherein, said at least one region of space contains all points at which a magnetic field-field gradient product of said transverse electromagnet equals or exceeds a threshold value; and, wherein said at least one region of space comprises a region of space between and including a first outer right circular cylinder 441 concentric with a second inner right circular cylinder 442, said first 441 and second 442 concentric right circular cylinders having a first coplanar base coincident with a first plane of a first circular pole face 435 of a first magnetic pole piece 426 of said transverse electromagnet 400, said first circular pole face 435 having a pole radius R [460] at which said magnetic field-field gradient product of said transverse electromagnet 400 has a maximum radial value; and, a second coplanar base coincident with a with a second plane of a second circular pole face 436 of an opposing second magnetic pole piece 427 of said transverse electromagnet 400, said second circular pole face 436 also having said pole radius R [460] at which said magnetic field-field gradient product of said transverse electromagnet 400 also has said maximum radial value, said first outer 441 and second inner 442 concentric right cylinders extending between said first circular pole face 435 and said second circular pole face 436 of said transverse electromagnet 400 and centering about a central longitudinal (y-)axis 437 of said transverse electromagnet 400, said first outer right circular cylinder 441 having a first outer radius $R_1$ [461], being greater than said pole radius R [460], at which first outer radius $R_1$ [461] said magnetic field-field gradient product of said transverse electromagnet 400 has a first threshold radial value, and said second inner right circular cylinder 442 having a second inner radius $R_2$ [462], being less than said pole radius R [460], at which second inner radius $R_2$ [462] said, of said transverse electromagnet 400 has a second threshold radial value.

2. The apparatus of claim 1, wherein said first and second magnetic circular pole faces 435, 436 of said first and second magnetic pole pieces 426, 427 are each modified to form a first modified pole face 435*m* and a second modified pole face 436*m*, each having a perimeter in the form of an n-sided regular polygon inscribed in a circle having said pole radius R [460] at which said magnetic field-field gradient product has said maximum radial value, and said at least one region of space comprises a region of space between and including a first outer prismatic polyhedron 441*p* having as its bases two opposing congruent n-sided polygons each inscribing a circle of said first outer radius $R_1$ [461] at which said magnetic field-field gradient product has said first threshold radial value, and a second inner prismatic polyhedron 442*p* having as its bases two opposing congruent n-sided polygons each inscribing a circle of said second inner radius $R_2$ [462] at which said magnetic field-field gradient product has said second threshold radial value, said first outer prismatic polyhedron 441*p* also inscribing said first outer right circular cylinder 441 and said second inner prismatic polyhedron 442*p* also inscribing said second inner right circular cylinder 442, said first outer prismatic polyhedron 441*p* and said second inner prismatic polyhedron 442*p* further having a first coplanar base coincident with the plane of said first modified pole face 435*m* and a second coplanar base coincident with a plane of said second modified pole face 436*m*, and extending between said modified pole faces 435*m*, 436*m* centered about said common central longitudinal (y-) axis 437.

3. The apparatus of claim 2, wherein N is an integer greater than or equal to 3.

4. The apparatus of claim 2, wherein said maximum radial value of said magnetic field-field gradient product of said transverse electromagnet 400 is at least about 5 $T^2$/m.

5. The apparatus of claim 2, wherein said first threshold radial value is about five (5) percent of said maximum radial value and said second threshold radial value is about five per of said maximum radial value.

6. The apparatus of claim 1, wherein said transverse electromagnet 400 is operationally controlled by a computer 201, and said bioreactor chamber positioning system and said biological in vitro support system 200 are operationally controlled by said computer 201.

7. The apparatus of claim 6, wherein said biological in vitro support system 200 comprises a gas flow control subsystem 230, a temperature control subsystem 240, a perfusion control subsystem 250, and a support system interface 220 that is configurable to independently route at least one first set of tubes 330 elaborated from said biological in vitro support system 200 to said at least one bioreactor chamber housing said at least one biospecimen in which there is induced said diamagnetic body force in said at least one region of space, and to return said at least one first set of tubes 330 from said at least one bioreactor chamber to said biological in vitro support system 200, thereby completing at least one closed tubing circuit between said biological in vitro support system 200 and said at least one bioreactor chamber disposed in said at least one region of space by said bioreactor positioning system.

8. The apparatus of claim 7, wherein said at least one first set of tubes 330 comprises a first afferent tube bundle 333 and a first efferent tube bundle 334, said first afferent tube bundle 333 comprising a triplet of tubes including a first afferent gas tube 333*g*, a first afferent temperature tube 333*t*, and a first afferent perfusion tube 333*p*, respectively elaborated from said gas flow control subsystem 230, said temperature control subsystem 240, and said perfusion control subsystem 250 of said biological in vitro support system 200; and, said first efferent tube bundle 334 comprising a doublet of tubes including a first efferent temperature tube 334*t*, and a first efferent perfusion tube 334*p*, respectively returning to said temperature control subsystem 240 and said perfusion control subsystem 250 of said biological in vitro support system 200.

9. The apparatus of claim 8, wherein said perfusion control subsystem 250 adjustably circulates a perfusate through said first afferent perfusion tube 333*p* to said at least one bioreactor chamber housing said at least one biospecimen in which there is induced said diamagnetic body force in said at least one region of space, and from said at least one bioreactor chamber through said first efferent perfusion tube 334*p* to said perfusion control subsystem 250, thereby forming a closed perfusion tubing circuit between said perfusion control subsystem 250 and said at least one bioreactor chamber disposed in said at least one region of space by said bioreactor positioning system.

10. The apparatus of claim 9, wherein said perfusion control subsystem 250 comprises a temperature controlled bath 241 containing a gas humidifier reservoir 253, a medium reservoir 254 containing said perfusate at a controllable pH, and a flow damper reservoir 255, that are serially connected to one another by perfusate tubing 258, in which perfusion control subsystem 250 gas from a perfusate gas source 259 is filtered and delivered to said gas humidifier reservoir 253 and thereafter delivered to said medium reservoir 254 for admixing with said perfusate, which perfusate is then pumped by a variable speed pump 251 to a flowmeter regulator multiplier unit 256 for afferent distribution therefrom by said first afferent perfusion tube 333*p* routed through said support system interface 220 to said at least one bioreactor chamber housing said at least one biospecimen in which there is induced said diamagnetic body force in said at least one region of space, and thereafter returned to said perfusion control subsystem 250 by said first efferent perfusion tube 334*p*, conducted thereto through said support system interface 220 and a manifold collecting unit 243, thereby forming a closed perfusion tubing circuit between said perfusion control subsystem 250 and said at least one bioreactor chamber disposed in said at least one region of space by said bioreactor positioning system.

11. The apparatus of claim 8, wherein said gas flow control subsystem 230 comprises a gas source 231 from which gas is delivered to a gas flowmeter regulator multiplier unit 232 and thence is delivered to said in vitro support system interface 220 by said first afferent gas tube 333*g* for afferent distribution to said at least one bioreactor chamber housing said at least one biospecimen in which there is induced said diamagnetic body force in said at least one region of space, and is thereafter vented to the atmosphere from said at least one bioreactor chamber.

12. The apparatus of claim 8, wherein said temperature control subsystem 240 comprises a temperature control bath unit 241 from which a fluid, maintained at a desired temperature, is pumped to a temperature flowmeter regulator multiplier unit 242 and thence, by said first afferent temperature tube 333*t* to said support system interface 220 for afferent distribution to a water-tight jacket 509 enveloping said at least one bioreactor chamber housing said at least one biospecimen in which there is induced said diamagnetic body force in said at least one region of space, and is thereafter returned from said water-tight jacket 509 to said support system interface 220 and thence to said temperature control subsystem 240 by said first efferent temperature tube 334t, thereby forming a closed temperature tubing circuit between said temperature control subsystem 240 and said water-tight jacket 509 of said at least one bioreactor chamber disposed in said at least one region of space by said bioreactor positioning system.

13. The apparatus of claim 8, wherein said bioreactor positioning system is disposed adjacent said transverse electromagnet 400, and comprises a nonmagnetic positioning arm 305, having an anterior terminus 306 and a posterior terminus 307, which posterior terminus 307 is exchangeably and slideably attached to an upright bioreactor positioning system column 302, for controllable linear translation and oscillation of said nonmagnetic positioning arm 305 by said computer 201 in the directions of a z-axis of said transverse electromagnet 400, said upright positioning system column 302 also being slideably mounted upon a bioreactor positioning system platform, 304 for controllable linear translation and oscillation of said upright bioreactor positioning system column 302 by said computer 201 in the directions of an x-axis of said transverse electromagnet 400, such that when said nonmagnetic positioning arm 305 is properly translated in said directions of said z-axis and said x-axis, said at least one bioreactor chamber housing said at least one biospecimen in which there is induced said diamagnetic body force is positioned in said at least one region of space.

14. The apparatus of claim 13, wherein said anterior terminus 306 makes exchangeably detachable connections with a nonmagnetic rectilinear frame 311, comprising a superior member 326, a first lateral member 327, and a second lateral member 328, said superior member 326 and said first lateral member 327 having a plurality of frame tubing conduits 338f for the carriage of at least one of said first set of tubes 330 to insert tubing conduits 338i of either a radially slotted rectilinear insert 800 or a tangentially slotted rectilinear insert 825, exchangeably held within said nonmagnetic rectilinear frame 311, said insert tubing conduits 338i communicating with at least one outer bioreactor chamber holding slot 807a or 807c of either said radially slotted rectilinear insert 800 or said tangentially slotted rectilinear insert, 825; and, said insert tubing conduits 338i also communicating with a central bioreactor chamber holding slot 807b of said radially slotted rectilinear insert 800 or said tangentially slotted rectilinear insert 825.

15. The apparatus of claim 14, wherein said superior member 326 and said first lateral member 327 have means for fastening either said radially slotted rectilinear insert 800 or said tangentially slotted rectilinear insert 825 within said nonmagnetic rectilinear frame 311 so that, when said nonmagnetic positioning arm 305 is properly translated by said computer 201 in directions of said x-axis and said z-axis, said at least one outer bioreactor chamber holding slot 807a or 807c is positioned within said at least one region of space, and said central bioreactor chamber holding slot 807b is positioned to be centered about said central longitudinal (y-) axis 437 of said transverse electromagnet 400, without said at least one region of space.

16. The apparatus of claim 13, wherein said anterior terminus 306 makes exchangeably detachable connections with a nonmagnetic circular frame 370, comprising a three-sided superior member 371 adapted to detachably join a linear inferior member 372 such that, when joined, an inner border 376 of said three-sided superior member 371 and an inner border 377 of said linear inferior member 372 form an approximately circular perimeter 374 about an approximately circular opening 378 having a first diameter, which approximately circular opening 378 exchangeably and detachably receives either a radially slotted circular insert 850 having a second diameter smaller than said first diameter or a tangentially slotted circular insert 875 having a second diameter smaller than said first diameter; said three-sided superior member 371 having a superior aspect, 373 a first lateral aspect, 381 and a second lateral aspect, 382 to which second lateral aspect 382 said anterior terminus 306 is exchangeably and detachably connected; said superior aspect 373 and said first lateral aspect 381 also having a plurality of frame tubing conduits 338f receiving at least one of said first set of tubes 330 for carriage thereof to insert tubing conduits 338i of either said radially slotted circular insert 850 or said tangentially slotted circular insert 875, which insert tubing conduits 338i communicate with at least one outer bioreactor chamber holding slot 807a of either said radially slotted circular insert 850 or said tangentially slotted circular insert 875, and also communicate with a central bioreactor chamber holding slot 807b of said radially slotted circular insert 850 or said tangentially slotted circular insert 875.

17. The apparatus of claim 16, wherein said linear inferior member 372 of said nonmagnetic circular frame 370 has means for rotatably fastening either said radially slotted circular insert 850 or said tangentially slotted circular insert 875 within said nonmagnetic circular frame 370 so that, when said nonmagnetic positioning arm 305 is properly translated by said computer 201 in directions of said x-axis and said z-axis, said at least one outer bioreactor chamber holding slot 807a is positioned within said at least one region of space, and said central slot 807b is positioned to be centered about said central longitudinal (y-) axis 437 of said transverse electromagnet 400, without said at least one region of space.

18. The apparatus of claim 15, wherein said radially slotted rectilinear insert 800 comprises a nonmagnetic thin rectangular parallelepiped, having a superior aspect 801, an inferior aspect 802, a first lateral aspect 803 and a second lateral aspect 804, said superior aspect 801 and said first lateral aspect 803 having a plurality of said insert tubing conduits 338i interfacing with said frame tubing conduits 338f of said rectilinear frame 311, which insert tubing conduits 338i deliver at least one of said first set of tubes 330 to said at least one outer bioreactor chamber holding slot 807a and 807c, cut into said radially slotted rectilinear insert 800 so as to orient a long axis 809ax, 809cx of said at least one bioreactor chamber 809a, 809c when held therein, radially aligned with said pole radius R [460] and to dispose said at least one bioreactor chamber 809a, 809c within said at least one region of space between a first circle having said first outer radius $R_1$ [461] and a second circle having said second inner radius; $R_2$ [462]; and, which insert tubing conduits 338i also deliver at least one of said first set of tubes 330 to said central bioreactor chamber holding slot 807b, said central bioreactor chamber holding slot 807b being cut into said radially slotted rectilinear insert 800 so as to orient a long axis 809bx of said at least one bioreactor chamber 809b, when held therein, radially aligned with said pole radius R [460] and to orient a geometrical center point of said at least one bioreactor chamber 809b coincident with said central longitudinal (y-) axis 437 of said transverse electromagnet 400, thereby disposing said at least one bioreactor chamber 809b without said at least one region of space.

19. The apparatus of claim 15, wherein said tangentially slotted rectilinear insert 825 comprises a nonmagnetic thin rectangular parallelepiped, having a superior aspect 801, an inferior aspect 802, a first lateral aspect 803 and a second lateral aspect 804, said superior aspect 801 and said first lateral aspect 803 having a plurality of said insert tubing conduits 338*i* interfacing with said frame tubing conduits 338*f* of said rectilinear frame 311, which insert tubing conduits 338*i* deliver at least one of said first set of tubes 330 to said at least one outer bioreactor chamber holding slot 807*a* and 807*c*, cut into said tangentially slotted rectilinear insert 825 so as to orient a long axis 809*ax*, 809*cx* of said at least one bioreactor chamber 809*a*, 809*c* when held therein, perpendicular to said pole radius R [460] and to dispose said at least one bioreactor chamber 809*a*, 809*c* within said at least one region of space between a first circle having said first outer radius $R_1$ [461] and a second circle having said second inner radius; $R_2$ [462]; and, which insert tubing conduits 338*i* also deliver at least one of said first set of tubes 330 to said central bioreactor chamber holding slot 807*b*, said central bioreactor chamber holding slot 807*b* being cut into said tangentially slotted rectilinear insert 825 so as to orient a long axis 809*bx* of said at least one bioreactor chamber 809*b*, when held therein, perpendicular to said pole radius R [460] and to orient a geometrical center point of said at least one bioreactor chamber 809*b* coincident with said central longitudinal (y-) axis 437 of said transverse electromagnet 400, thereby disposing said at least one bioreactor chamber 809*b* without said at least one region of space.

20. The apparatus of claim 17, wherein said radially slotted circular insert 850 comprises a nonmagnetic thin circular solid with a perimeter having openings into a plurality of said insert tubing conduits 338*i* interfacing with said frame tubing conduits 338*f* of said circular frame 370, which insert tubing conduits 338*i* deliver at least one of said first set of tubes 330 to said at least one outer bioreactor chamber holding slot 807*a*, 807*c* cut into said radially slotted circular insert 850 so as to orient a long axis 809*ax* 809*cx* of said at least one bioreactor chamber 809*a* 809*c*, when held therein, radially aligned with said pole radius R [460] and to dispose said at least one bioreactor chamber 809*a*, 809*c* within said at least one region of space, between a first circle having said first outer radius $R_1$ [461] and a second circle having said second inner radius $R_2$ [462]; and, which insert tubing conduits 338*i* further deliver at least one of said first set of tubes 330 to said central bioreactor chamber holding slot 807*b* cut into said radially slotted circular insert 850 so as to orient a long axis 809*bx* of said at least one bioreactor chamber 809*b*, when held therein, radially aligned with said pole radius R [460] and to orient a geometrical center point of said at least one bioreactor chamber 809*b* coincident with said central longitudinal (y-) axis 437 of said transverse electromagnet 400, thereby disposing said at least one bioreactor chamber 809*b* without said at least one region of space.

21. The apparatus of claim 17, wherein said tangentially slotted circular insert 875 comprises a nonmagnetic thin circular solid with a perimeter having openings into a plurality of said insert tubing conduits 338*i* interfacing with said frame tubing conduits 338*f* of said circular frame 370, which insert tubing conduits 338*i* deliver at least one of said first set of tubes 330 to said at least one outer bioreactor chamber holding slot 807*a*, 807*c* cut into said tangentially slotted circular insert 875 so as to orient a long axis 809*ax* 809*cx* of said at least one bioreactor chamber 809*a*809*c*, when held therein, perpendicular to said pole radius R [460] and to dispose said at least one bioreactor chamber 809*a*, 809*c* within said at least one region of space, between a first circle having said first outer radius $R_1$ [461] and a second circle having said second inner radius $R_2$ [462]; and, which insert tubing conduits 338*i* further deliver at least one of said first set of tubes 330 to said central bioreactor chamber holding slot 807*b* cut into said tangentially slotted circular insert 875 so as to orient a long axis 809*bx* of said at least one bioreactor chamber 809*b*, when held therein, perpendicular to said pole radius R [460] and to orient a geometrical center point of said at least one bioreactor chamber 809*b* coincident with said central longitudinal (y-) axis 437 of said transverse electromagnet 400, thereby disposing said at least one bioreactor chamber 809*b* without said at least one region of space.

22. The apparatus of claim 12, wherein said at least one bioreactor chamber includes a nonmagnetic water-impermeable common body 511 comprising a water-tight inner volume 501 in the general form of a rectangular parallelepiped confined on four sides by two pairs of parallel opposing long double-layered walls 503L1 and 503L2 separated by an intervening region of space 507 that forms said rectangular water-tight jacket 509 enveloping said at least one bioreactor chamber, and confined on two remaining sides by one pair of opposing short walls 502S1 and 502S2, each bearing a tab 812*t* for insertion into a corresponding notch 812*n* fashioned into at least one outer bioreactor chamber holding slot 807*a* or 807*c* or a central bioreactor chamber holding slot 807*b* of either a radially slotted rectilinear insert 800, a tangentially slotted rectilinear insert 825, a radially slotted circular insert 850 or a tangentially slotted circular insert 875.

23. The apparatus of claim 22, wherein said nonmagnetic water-impermeable common body 511 receives said first afferent tube bundle 333 and said first efferent tube bundle 334, carried to it from insert tubing conduits 338*i*, of either said radially slotted rectilinear insert 800, said tangentially slotted rectilinear insert, 825, said radially slotted circular insert 850 or said tangentially slotted circular insert 875, communicating with said at least one outer bioreactor chamber holding slot 807*a* or 807*c* or said central bioreactor chamber holding slot 807*b* of either said radially slotted rectilinear insert 800, said tangentially slotted rectilinear insert, 825, said radially slotted circular insert 850 or said tangentially slotted circular insert 875.

24. The apparatus of claim 23, wherein one of said short walls 502S1 and 502S2 comprises a removable water-tight cap 505 by which said water-tight inner volume 501 is accessed for the housing and sustenance in vitro therein of said at least one biospecimen.

25. The apparatus of claim 24, wherein said rectangular water-tight jacket 509 has an afferent temperature port 516*t* for detachably connecting said first afferent temperature tube 333*t* and an efferent temperature port 517*t* for detachably connecting said first efferent temperature tube 334*t*, thereby forming said closed temperature tubing circuit between said temperature control subsystem 240 and said rectangular water-tight jacket 509 of said at least one bioreactor chamber disposed in said at least one region of space by said bioreactor positioning system.

26. The apparatus of claim 25, wherein said inner volume 501 of said common body 511 has a plurality of general purpose ports 518*a*, 518*b*, and 518*c* for venting gas or detachably and exchangeably connecting said first afferent gas tube 333*g*, said first afferent perfusion tube 333*p*, and said first efferent perfusion tube 334*p*.

27. The apparatus of claim 26, wherein opposing interior surfaces of one pair of said two pairs of parallel opposing long double-layered walls 503L1 and 503L2 of said common body 511 are formed into a plurality of parallel and opposing inwardly projecting ledges 513 for the carriage thereon of said biospecimens mounted on a plurality of slides 512*a*, 512*b*, 512*c*.

28. The apparatus of claim 27, wherein said plurality of parallel and opposing inwardly projecting ledges 513 for the carriage thereon of said biospecimens mounted on said plurality of slides 512*a*, 512*b*, and 512*c*, are spaced apart from one another such that when said at least one bioreactor chamber is lodged within said at least one outer bioreactor chamber holding slot 807a or 807c or said central bioreactor chamber holding slot 807b of said tangentially slotted rectilinear insert 825 or said tangentially slotted circular insert 875, said ledges 513 dispose said biospecimens mounted on said plurality of slides 512a, 512b, 512c on parallel planes within said at least one region of space that are perpendicular to said pole radius R [460] and parallel to a tangent line of a first circle having said first outer radius $R_1$ [461] and a second circle having said second inner radius $R_2$ [462].

29. The apparatus of claim 27, wherein said plurality of parallel and opposing inwardly projecting ledges 513 for the carriage thereon of said biospecimens mounted on said plurality of slides 512a, 512b, 512c, are spaced apart from one another such that when said at least one bioreactor chamber is lodged within said at least one outer bioreactor chamber holding slot 807a or 807c or said central bioreactor chamber holding slot 807b of said radially slotted rectilinear insert 800 or said radially slotted circular insert 850, said ledges 513 dispose said biospecimens mounted on said plurality of slides 512a, 512b, 512c on parallel planes within said at least one region of space that are radially aligned with said pole radius R [460] and perpendicularly intersect a tangent line to a first circle having said first outer radius $R_1$ [461] and a second circle having said second inner radius $R_2$ [462].

30. The apparatus of claim 26, wherein said inner volume 501 removably receives a nonmagnetic, water-impermeable flow insert 551 comprising an L-shaped frame 551F having a base member 551B, of a base member length, with a base recess 551BR for receiving said biospecimen, said base member 551B being perpendicular to a supporting wall 551W, from which supporting wall 551W there project, in planes parallel to the plane of said base member 551B, a first flow divider 551A of a flow divider length, in general form of rectangular parallelepiped, having a first divider recess 551BR for receiving another of said biospecimen and a second flow divider 551C, of said flow divider length, also having the general form of rectangular parallelepiped, wherein said flow divider length is less than said base length, and said first flow divider 551A and said second flow divider 551C project from said supporting wall 551W so as to leave symmetrically opposing columns of space 501a, 501b within said inner volume 501 for the ingress and egress of a perfusate.

31. The apparatus of claim 30, wherein said inner volume 501 contains said flow insert 551, thereby creating a 2-D flow bioreactor chamber.

32. The apparatus of claim 31, wherein, said general purpose port 518c is closed, said 2-D flow bioreactor chamber receives said perfusate from said general purpose port 518a connected to said first afferent perfusion tube 333p, said flow divider 551 directs said perfusate tangentially across said base recess 551BR of said base member 551B, and tangentially across said first divider recess 551BR of said first flow divider 551A, and said flow divider 551 further directs said perfusate out of said 2-D flow bioreactor chamber through said general purpose port 518b connected to said first efferent perfusion tube 334p, thereby forming a closed perfusion circuit with said perfusion control subsystem 250 of said biological in vitro support system 200.

33. The apparatus of claim 32, wherein said base recess 551BR of said base member 551B and said first-divider recess 551BR of said first flow divider 551A are spaced apart from one another such that when said 2-D flow bioreactor chamber is lodged within said first outer bioreactor chamber holding slot 807a or said second outer bioreactor chamber holding slot 807c of said radially slotted rectilinear insert 800 or said radially slotted circular insert 850, said biospecimens will respectively be carried by said first-divider recess 551AR and said base recess 551BR in planes that are radially aligned with said pole radius R [460] and perpendicularly intersect a tangent to a circle of said first outer radius $R_1$ [461] in said region of space and a tangent to a circle of said second inner radius $R_2$ [462] in said region of space; and, said flow insert 551 causes said perfusate to flow tangentially across said base recess 551BR and said first-divider recess 551AR in a manner that maintains the direction of a flow vector $P_F$ [190] of said perfusate parallel to the direction of said diamagnetic body force induced in said biospecimens.

34. The apparatus of claim 32, wherein said base recess 551BR of said base member 551B and said first-divider recess 551AR of said first flow divider 551A are spaced apart from one another such that when said 2-D flow bioreactor chamber is lodged within said first outer bioreactor chamber holding slot 807a or said second outer bioreactor chamber holding slot 807c of said tangentially slotted rectilinear insert 825 or said tangentially slotted circular insert 875, said biospecimens will be respectively carried by said first-divider recess 551AR and said base recess 551BR in planes that are perpendicular to said pole radius R [460] and parallel to a tangent to a circle of said first outer radius $R_1$ [461] in said region of space and a tangent to a circle of said second inner radius $R_2$ [462] in said region of space; and, said flow insert 551 causes said perfusate to flow tangentially across said base recess 551BR and said first-divider recess 551AR in a manner that maintains the direction of a flow vector $P_F$ [190] of said perfusate perpendicular to the direction of said diamagnetic body force induced in said biospecimens.

35. The apparatus of claim 26, wherein one pair of said two pairs of parallel opposing double-layered long walls 503L1, 503L2 of said common body 511 are fitted with a plurality paired parallel and opposing retaining clips 561, respectively securing a plurality of tissue microcassettes 562a, 562b, 562c in an orientation parallel to said short walls 502S1 and 502S2 of said common body 511, each of which tissue microcassettes 562a, 562b, 562c may house said at least one biospecimen, said paired parallel and opposing retaining clips 561 being spaced apart from one another such that when said bioreactor chamber is lodged within said at least one outer bioreactor chamber holding slot 807a, 807c or said central bioreactor chamber holding slot 807b of said tangentially slotted rectilinear insert 825 or said tangentially slotted insert 875, said paired parallel and opposing retaining clips 562 dispose said tissue microcassettes 562a, 562b, 562c on parallel planes within said at least one region of space that are perpendicular to said pole radius R [460] and parallel to a tangent line of a first circle having said first outer radius $R_1$ [461] and a second circle having said second inner radius $R_2$ [462].

36. The apparatus of claim 35, wherein said paired parallel and opposing retaining clips 561 are spaced apart from one another such that when said bioreactor chamber is lodged within said at least one outer bioreactor chamber holding slot 807a, 807c or said central bioreactor chamber holding slot 807b of said radially slotted rectilinear insert 800 or said radially slotted circular insert 850, said paired parallel and opposing retaining clips 561 dispose said tissue microcassettes 562a, 562b, 562c on parallel planes within said at least one region of space that are radially aligned with said pole radius R [460] and perpendicularly intersect a tangent line to a first circle having said first outer radius $R_1$ [461] and a second circle having said second inner radius $R_2$ [462].

* * * * *